United States Patent
Majumdar et al.

(10) Patent No.: US 11,613,547 B2
(45) Date of Patent: Mar. 28, 2023

(54) G-PROTEIN BIASED OPIOID RECEPTOR AGONIST/ANALGESICS WITH REDUCED ARRESTIN RECRUITMENT

(71) Applicants: University of Health Sciences & Pharmacy in St. Louis, St. Louis, MO (US); University of Southern California, Los Angeles, CA (US); The University of North Carolina at Chapel Hill, Chapel Hill, NC (US); Memorial Sloan Kettering Cancer Center, New York, NY (US); University of Florida Research Foundation, Incorporated, Gainesville, FL (US); Memorial Sloan Kettering Cancer Center, New York, NY (US)

(72) Inventors: Susruta Majumdar, St. Louis, MO (US); Vsevolod Katritch, Los Angeles, CA (US); Bryan Roth, Chapel Hill, NC (US); Jay McLaughlin, Gainesville, FL (US); Saheem Zaidi, Los Angeles, CA (US); Gavril W. Pasternak; Rajendra Uprety, Cary, NC (US)

(73) Assignees: University of Health Sciences & Pharmacy in St. Louis, St. Louis, MO (US); University of Southern California, Los Angeles, CA (US); The University of North Carolina at Chapel Hill, Chapel Hill, NC (US); Memorial Sloan Kettering Cancer Center, New York, NY (US); University of Florida Research Foundation, Incorporated, Gainesville, FL (US)

(*) Notice: Subject to any disclaimer, the term of this patent is extended or adjusted under 35 U.S.C. 154(b) by 0 days.

(21) Appl. No.: 16/924,037

(22) Filed: Jul. 8, 2020

(65) Prior Publication Data

US 2021/0061814 A1 Mar. 4, 2021

Related U.S. Application Data

(60) Provisional application No. 62/871,578, filed on Jul. 8, 2019.

(51) Int. Cl.
*C07D 489/00* (2006.01)
*C07D 221/28* (2006.01)

(52) U.S. Cl.
CPC .......... *C07D 489/00* (2013.01); *C07D 221/28* (2013.01)

(58) Field of Classification Search
CPC .................................................. C07D 489/00
See application file for complete search history.

(56) References Cited

U.S. PATENT DOCUMENTS

| 4,446,140 A | 5/1984 | Nelson |
| 5,321,012 A | 6/1994 | Mayer et al. |
| 5,523,323 A | 6/1996 | Maccecchini |
| 5,654,281 A | 8/1997 | Mayer et al. |
| 5,948,788 A | 9/1999 | Huang et al. |

(Continued)

FOREIGN PATENT DOCUMENTS

| WO | WO 1998/014427 | 4/1998 |
| WO | WO 2012/166891 | 12/2012 |

OTHER PUBLICATIONS

Ghirmai "Synthesis and Biological Evaluation of α- and β-6-Amido Derivatives of 17-Cyclopropylmethyl-3,14β-dihydroxy-4,5α-epoxymorphinan: Potential Alcohol-Cessation Agents." Journal of Medicinal Chemistry, 2008, 51(6), 1913-1924.*

(Continued)

*Primary Examiner* — David K O'Dell
(74) *Attorney, Agent, or Firm* — Parker Highlander PLLC

(57) ABSTRACT

In some aspects, the present disclosure provides compounds of the formula:

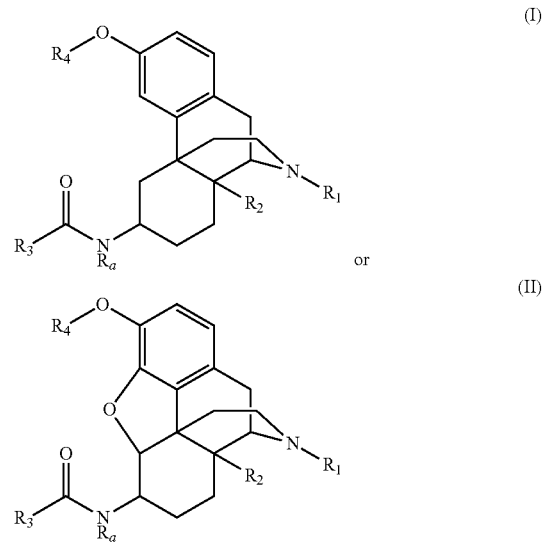

wherein the variables are as defined herein. In some embodiments, these compounds may be used to reduce the pain of a patient. These compounds may be used in pain relief and show an improved pharmaceutical profile relative to other commonly used opiates and opioid derivatives.

19 Claims, 13 Drawing Sheets

(56) References Cited

U.S. PATENT DOCUMENTS

| | | | |
|---|---|---|---|
| 6,277,859 B1* | 8/2001 | Nagase | A61P 9/00 514/282 |
| 2016/0318872 A1 | 11/2016 | Lockman et al. | |
| 2019/0152982 A1 | 5/2019 | Zhang et al. | |

OTHER PUBLICATIONS

Kobylecki "Common Anionic Receptor Site Hypothesis: Its Relevance to the Antagonist Action of Naloxone." Journal of Medicinal Chemistry, 1982, pp. 116-120.*

Wislicenus, J. "Adolph Strecker's Short Textbook of Organic Chemistry" 1881, Spottiswoode: London, pp. 38-39.*

"ICD-9-CM Tabular List of Diseases (FY03)" on the Washington University School of Medicine in St. Louis website Online "http://gamma.wustl.edu/division/icd9tbp.pdf" accessed Sep. 10, 2015.*

Mark Connor and MacDonald J Christie "Opioid Receptor Signaling Mechanisms" Clinical and Experimental Pharmacology and Physiology 1999 26, 493-499.*

Al-Hasani, "Molecular Mechanisms of Opioid Receptor-dependent Signaling and Behavior"Anesthesiology 2011; 115:1363-81.*

Quock et. al., "The d-Opioid Receptor: Molecular Pharmacology, Signal Transduction, and the Determination of Drug Efficacy" Pharmacological Reviews 1999, 51(3), 503-532.*

Freye "Opioids in Medicine: A Comprehensive Review on the Mode of Action and the Use of Analgesics in Different Clinical Pain States", Springer: Dordrecht, 2008.*

Lee "Comparison of complex regional pain syndrome and fibromyalgia" Medicine (2019) 98:7.*

Painter JT, Crofford LJ. "Chronic opioid use in fibromyalgia syndrome: a clinical review." J Clin Rheumatol. 2013;19(2): 72-77.*

Ngian "The use of opioids in fibromyalgia" International Journal of Rheumatic Diseases 2011; 14: 6-11.*

Kia "Update on Treatment Guideline in Fibromyalgia Syndrome with Focus on Pharmacology" Biomedicines 2017, 5, 20.*

Bohn et al., "Enhanced morphine analgesia in mice lacking beta-arrestin 2," Science, 286(5449):2495-2498, 1999.

Bu et al., "Enhancement of morphine analgesia and prevention of morphine tolerance by downregulation of β-arrestin 2 with antigene RNAs in mice," Int J Neurosci, 125:56-65, 2015.

Che et al., "Structure of the Nanobody-Stabilized Active State of the Kappa Opioid Receptor," Cell, 172:55-67.e15, 2018.

Chen et al., "Molecular cloning and functional expression of a mu-opioid receptor from rat brain," Mol. Pharmacol., 44(1):8-12, 1993.

Chun et al., "Structure-Activity Investigation of a G Protein-Biased Agonist Reveals Molecular Determinants for Biased Signaling of the D 2 Dopamine Receptor," Frontiers in Synaptic Neuroscience, 10:2, 2018.

Cirino et al., "Characterization of Sigma 1 Receptor Antagonist CM-304 and Its Analog, AZ-66: Novel Therapeutics Against Allodynia and Induced Pain," Front. Pharmacol., 10:678, 2019.

Crooks et al., "Opiate receptor binding properties of morphine-, dihydromorphine-, and codeine 6-O-sulfate ester congeners," Bioorganic and Medicinal Chemistry Letters, 16:4291-4295, 2006.

Crowley et al., "Synthetic Studies of Neoclerodane Diterpenes from Salvia divinorum: Identification of a Potent and Centrally Acting μ Opioid Analgesic with Reduced Abuse Liability," Journal of Medicinal Chemistry, 59:11027-11038, 2016.

DeWire et al., "A G protein-biased ligand at the μ-opioid receptor is potently analgesic with reduced gastrointestinal and respiratory dysfunction compared with morphine," J. Pharmacol. Exp. Ther., 344:708-717, 2013.

Dosaka-Akita et al., "The kappa opioid agonist U-50,488H antagonizes respiratory effects of mu opioid receptor agonists in conscious rats," J. Pharmacol. Exp. Ther., 264:631-637, 1993.

Elliott et al. "The NMDA receptor antagonists, LY274614 and MK-801, and the nitric oxide synthase inhibitor, NG-nitro-L-arginine, attenuate analgesic tolerance to the mu-opioid morphine but not to kappa opioids," Pain, 56(1):69-75, 1994.

Fenalti et al., "Molecular control of δ-opioid receptor signalling," Nature, 506:191-196, 2014.

Grinnell et al., "Mediation of buprenorphine analgesia by a combination of traditional and truncated mu opioid receptor splice variants," Synapse, 70:395-407, 2016.

Gundry et al., "A Practical Guide to Approaching Biased Agonism at G Protein Coupled Receptors," Front. Neurosci., 11:17, 2017.

Harding et al., "Neoclerodane diterpenes as a novel scaffold for mu opioid receptor ligands," J.Med.Chem, 48:4765-4771, 2005.

Hupp & Neumeyer, "Rapid access to morphinones: removal of 4,5-ether bridge with Pd-catalyzed triflate reduction," Tetrahedron Lett., 51:2359-2361, 2010.

Jiang et al., "Stereochemical studies on medicinal agents. 23. Synthesis and biological evaluation of 6-amino derivatives of naloxone and naltrexone," Journal of Medicinal Chemistry, 20:1100-1102, 1977.

Kenakin et al., "A simple method for quantifying functional selectivity and agonist bias," ACS Chem. Neuroscience, 3:193-203, 2012.

Kobylecki et al., "Common anionic receptor site hypothesis: its relevance to the antagonist action of naloxone," Journal of Medicinal Chemistry, 25:116-120, 1982.

Kolesnikov et al. "1-Aminocyclopropane carboxylic acid (ACPC) prevents mu and delta opioid tolerance," Life Sci., 55:1393-1398, 1994.

Kolesnikov et al., "Blockade of tolerance to morphine but not to kappa opioids by a nitric oxide synthase inhibitor," Proc. Natl. Acad. Sci. USA, 90:5162-5166, 1993.

Kruegel et al., "Synthetic and Receptor Signaling Explorations of the Mitragyna Alkaloids: Mitragynine as an Atypical Molecular Framework for Opioid Receptor Modulators," Journal of the American Chemical Society, 138:6754-6764, 2016.

Li et al., "Improvement of morphine-mediated analgesia by inhibition of β-arrestin2 expression in mice periaqueductal gray matter," Int J Mol Sci., 10:954-963. 2009.

Luttrell et al., "Fulfilling the Promise of "Biased" G Protein-Coupled Receptor Agonism," Mol. Pharmacol., 88:579-588, 2015.

Lutz and Pfister, "Opioid receptors and their pharmacological profiles," J. Receptor Res., 12:267-286, 1992.

Majumdar et al., "Generation of novel radiolabeled opiates through site-selective iodination," Bioorg Med Chem Lett, 21:4001-4004, 2011.

Majumdar et al., "Truncated G protein-coupled mu opioid receptor MOR-1 splice variants are targets for highly potent opioid analgesics lacking side effects," Proc. Natl. Acad. Sci. USA, 108:19778-19783, 2011.

Manglik et al., "Structure-based discovery of opioid analgesics with reduced side effects," Nature, 537:185-190, 2016.

Matthes et al., "Activity of the delta-opioid receptor is partially reduced, whereas activity of the kappa-receptor is maintained in mice lacking the mu-receptor," J. Neuroscience, 18:7285-7295, 1998.

Olson et al., "Endogenous opiates: 1988," Peptides, 10(6):1253-1280, 1989.

Osa et al., A New Useful Conversion Method of Naltrexone to 14-Deoxynaltrexone, Heterocycles, 69(1):271-282, 2006.

Pasternak, "Pharmacological mechanisms of opioid analgesics," Clin. Neuropharmacol., 16:1:1-18, 1993.

PCT International Search Report and Written Opinion issued in International Application No. PCT/US2020/041274, dated Nov. 24, 2020.

Pickett et al., "Mild, Pd-catalyzed stannylation of radioiodination targets," Bioorg. Med. Chem. Lett., 25:1761-1764, 2015.

Portoghese et al., "A highly selective delta 1-opioid receptor antagonist: 7-benzylidenenaltrexone," Eur. J. Pharmacol., 218:195-196, 1992.

Pubchem CID 24822297, created Jun. 30, 2008, Accessed Dec. 2020.

Raehal et al., "Morphine side effects in beta-arrestin 2 knockout mice," J.Pharmacol.Exp.Ther., 314:1195-1201, 2005.

(56) References Cited

OTHER PUBLICATIONS

Rankovic et al., "Biased agonism: An emerging paradigm in GPCR drug discovery," *Bioorganic & Medicinal Chemistry Letters*, 26:241-250, 2016.
Reilley et al., "Identification of two novel, potent, low-liability antinociceptive compounds from the direct in vivo screening of a large mixture-based combinatorial library," *AAPS J.*, 12:318-329, 2010.
Rives et al., "6'-Guanidinonaltrindole (6'-GNTI) is a G protein-biased κ-opioid receptor agonist that inhibits arrestin recruitment," *J. Biol. Chem.*, 287:27050-27054, 2012.
Robinson & Roskamp, "Solid phase synthesis of guanidines," *Tetrahedron*, 53:6697-6705, 1997.
Schmid et al., "Bias Factor and Therapeutic Window Correlate to Predict Safer Opioid Analgesics," *Cell*, 171:1165-1175.e13, 2017.
Schmid et al., "Functional selectivity of 6'-guanidinonaltrindole (6'-GNTI) at κ-opioid receptors in striatal neurons," *J. Biol. Chem.*, 288:22387-22398, 2013.
Simon et al., "Application of the Mitsunobu Reaction for Morphine Compounds. Preparation of 6β-Aminomorphine and Codeine Derivatives," *Synthetic Communications*, 22:913-921, 1992.
Simon et al., "Stereoselective synthesis of β-naltrexol, β-naloxol β-naloxamine, β-naltrexamine and related compounds by the application of the mitsunobu reac," *Tetrahedron*, 50:9757-9768, 1994.
Simon, "Opioid receptors and endogenous opioid peptides," *Medicinal Res. Rev.*, 11:357-374, 1991.
Sofuoglu et al., "Differential antagonism of delta opioid agonists by naltrindole and its benzofuran analog (NTB) in mice: evidence for delta opioid receptor subtypes," *J. Pharmacol. Ther.*, 257:676-680, 1991.
Standifer and Pasternak, "G proteins and opioid receptor-mediated signalling," *Cell Signal*, 9:237-248, 1997.
Standifer et al., "Differential blockade of opioid analgesia by antisense oligodeoxynucleotides directed against various G protein alpha subunits," *Mol. Pharmacol.*, 50:293-298, 1996.
Tius & Kerr, "A novel approach to the synthesis of morphine alkaloids: the synthesis of (d,l)-thebainone-A," *Journal of the American Chemical Society*, 114:5959-5966, 1992.
Townsend et al., "Effects of nalfurafine on the reinforcing, thermal antinociceptive, and respiratory-depressant effects of oxycodone: modeling an abuse-deterrent opioid analgesic in rats," *Psychopharmacology*, 234:2597-2605, 2017.
Trujillo and Akil, "Inhibition of morphine tolerance and dependence by the NMDA receptor antagonist MK-801," *Science*, 251:85-87, 1991.
Váradi et al., "Mitragynine/Corynantheidine Pseudoindoxyls as Opioid Analgesics with Mu Agonism and Delta Antagonism, Which Do Not Recruit β-Arrestin-2," *J Med Chem*, 59:8381-8397, 2016.
Váradi et al., "Novel 6β-acylaminomorphinans with analgesic activity," *European J. Med. Chem.*, 69:786-789, 2013.
Váradi et al., "Synthesis and characterization of a dual kappa-delta opioid receptor agonist analgesic blocking cocaine reward behavior," *ACS Chemical Neuroscience*, 6:1813-1824, 2015.
Váradi et al., "Synthesis of Carfentanil Amide Opioids Using the Ugi Multicomponent Reaction," *ACS Chemical Neuroscience*, 6:1570-1577, 2015.
Yasuda et al., "Cloning and functional comparison of kappa and delta opioid receptors from mouse brain," *Proc. Natl. Acad. Sci. USA*, 90:6736-6740, 1993.
Yuan et al., "Design, synthesis, and biological evaluation of 14-heteroaromatic-substituted naltrexone derivatives: pharmacological profile switch from mu opioid receptor selectivity to mu/kappa opioid receptor dual selectivity," *J Med Chem*, 56:9156-9169, 2013.
Zhang et al., "Design, synthesis and biological evaluation of 4'-demethyl-4-deoxypodophyllotoxin derivatives as novel tubulin and histone deacetylase dual inhibitors," *RSC Advances*, 4:40444-40448, 2014.
Zhang et al., "Synthesis and pharmacological evaluation of 6,7-indolo/thiazolo-morphinans—further SAR of levorphanol," *Journal of Medicinal Chemistry*, 50:2747-2751, 2007.

\* cited by examiner

G-PROTEIN BIASED OPIOID RECEPTOR AGONIST/ANALGESICS WITH REDUCED ARRESTIN RECRUITMENT

This application claims the benefit of priority to U.S. Provisional Application No. 62/871,578, filed on Jul. 8, 2019. The entire contents of which are hereby incorporated by reference.

The invention was made with government support under Grant No. DA034106, R01DA046487 and R21DA045884 awarded by the National Institutes of Health. The government has certain rights in the invention.

BACKGROUND

1. Field

The present disclosure relates generally to the field of pharmaceuticals and compound which alleviate pain. More particularly, it concerns new opioid compounds which show reduced addictive potential and respiratory depression. Instead compounds described herein may show respiratory stimulation contrary to the expected respiratory depression common to clinically used mu opioid agonists like fentanyl and oxycodone.

2. Description of Related Art

Opioids are a widely used class of compounds for managing pain in patients. The use of this class of compounds is often limited by significant side effects and the compounds addictive nature. Typically, opioids generally target both the G-protein pathway as well as activate beta-arrestin. Activation of the G-protein pathway is associated with the desired pharmaceutical activity leading to reduced sensation of pain. On the other hand, the activation of the beta-arrestin pathway is associated with increased side effects such as respiratory depression and addiction. See, for example, Kruegel et al., 2016, Varadi et al., 2016, Rankovic et al., 2016, Bu et al., 2015, Li et al., 2009, Bohn et al., 1999, Raehal et al., 2005, Harding et al., 2005, Crowley et al., 2016, Grinnell et al., 2016, Dewire et al., 2013, Manglik et al., 2016, and Schmid et al., 2017. Currently used opioid drugs like morphine and fentanyl suffer from an unfavorable side effect profile as both lead to activation of both pathways. Therefore, there remains a need to develop new compounds which show an improved pharmaceutical profile including increased G-protein activation with reduced activation of the β-arrestin2 pathway.

SUMMARY

In some aspects, the present disclosure provides compounds which are opioid derivatives which show an improved pharmaceutical profile such as reduced activation of β-arrestin2. In some embodiments, the compounds described herein may form a chair confirmation in the C ring when these compounds bind to both MOR and KOR. Without wishing to be bound by any theory, it is believed that these compounds lead to G-biased signaling and pain relief without additional addictive or respiratory related side effects. In some embodiments, the compounds are further defined as:

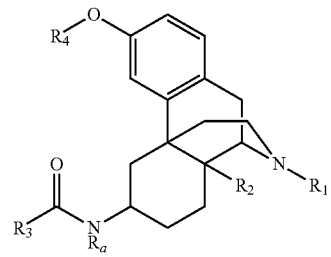

(I)

wherein:

$R_1$ is alkyl$_{(C \leq 8)}$, cycloalkyl$_{(C \leq 8)}$, alkenyl$_{(C \leq 8)}$, or —$Y_1$—$R_1'$, wherein:

$Y_1$ is alkanediyl$_{(C \leq 8)}$ or substituted alkanediyl$_{(C \leq 8)}$; and $R_1'$ is cycloalkyl$_{(C \leq 8)}$, aryl$(C \leq 12)$, or a substituted version of either of these groups;

$R_2$ is hydrogen, hydroxy, alkoxy$_{(C \leq 8)}$, alkenyloxy$_{(C \leq 8)}$, aryloxy$_{(C \leq 8)}$, aralkoxy$_{(C \leq 8)}$, acyloxy$_{(C \leq 8)}$, or a substituted version of any of the last five groups;

$R_a$ is hydrogen, alkyl$_{(C \leq 6)}$, or substituted alkyl$_{(C \leq 6)}$;

$R_3$ is a group of the formula:

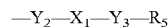

—$Y_2$—$X_1$—$Y_3$—$R_5$ wherein:

$Y_2$ and $Y_3$ are each independently selected from a covalent bond, alkanediyl$_{(C \leq 8)}$, or substituted alkanediyl$_{(C \leq 8)}$;

$X_1$ is arenediyl$_{(C \leq 12)}$, heteroarenediyl$_{(C \leq 12)}$, or a substituted version of either group; and $R_5$ is cyano, halo, hydroxy, nitro, alkyl$_{(C \leq 8)}$, substituted alkyl$_{(C \leq 8)}$, aryl$_{(C \leq 8)}$, substituted aryl$_{(C \leq 8)}$, or —C(O)$R_6$, wherein:

$R_b$ is hydrogen, alkyl$_{(C \leq 6)}$, or substituted alkyl$_{(C \leq 6)}$; or $R_5$ is amino, alkylamino$_{(C \leq 8)}$, substituted alkylamino$_{(C \leq 8)}$, dialkylamino$_{(C \leq 12)}$, substituted dialkylamino$_{(C \leq 12)}$, or —NR$_c$C(NR$_d$)R$_5'$, wherein:

$R_c$ and $R_d$ are each independently hydrogen, alkyl$_{(C \leq 6)}$, or substituted alkyl$_{(C \leq 6)}$;

$R_5'$ is amino, alkylamino$_{(C \leq 8)}$, substituted alkylamino$_{(C \leq 8)}$, dialkylamino$_{(C \leq 12)}$, or substituted dialkylamino$_{(C \leq 12)}$; and $R_4$ is hydrogen, alkyl$_{(C \leq 6)}$, substituted alkyl$_{(C \leq 6)}$, acyl$_{(C \leq 6)}$, or substituted acyl$_{(C \leq 6)}$; or a compound of the formula:

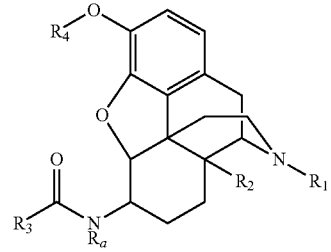

(II)

wherein:

R$_1$ is alkyl$_{(C\leq 8)}$, cycloalkyl$_{(C\leq 8)}$, alkenyl$_{(C\leq 8)}$, or —Y$_1$—R$_1$', wherein:
  Y$_1$ is alkanediyl$_{(C\leq 8)}$ or substituted alkanediyl$_{(C\leq 8)}$; and
  R$_1$' is cycloalkyl$_{(C\leq 8)}$, aryl$_{(C\leq 12)}$, or a substituted version of either of these groups;

R$_2$ is hydrogen, hydroxy, alkoxy$_{(C\leq 8)}$, alkenyloxy$_{(C\leq 8)}$, aryloxy$_{(C\leq 8)}$, aralkoxy$_{(C\leq 8)}$, acyloxy$_{(C\leq 8)}$, or a substituted version of any of the last five groups;

R$_a$ is hydrogen, alkyl$_{(C\leq 6)}$, or substituted alkyl$_{(C\leq 6)}$;

R$_3$ is a group of the formula:

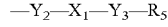

wherein:
  Y$_2$ and Y$_3$ are each independently selected from a covalent bond, alkanediyl$_{(C\leq 8)}$, or substituted alkanediyl$_{(C\leq 8)}$;
  X$_1$ is arenediyl$_{(C\leq 12)}$, heteroarenediyl$_{(C\leq 12)}$, or a substituted version of either group; and
  R$_5$ is cyano, halo, hydroxy, nitro, alkyl$_{(C\leq 8)}$, substituted alkyl$_{(C\leq 8)}$, aryl$_{(C\leq 8)}$, substituted aryl$_{(C\leq 8)}$, or —C(O)R$_b$, wherein:
    R$_b$ is hydrogen, alkyl$_{(C\leq 6)}$, or substituted alkyl$_{(C\leq 6)}$; or
  R$_5$ is amino, alkylamino$_{(C\leq 8)}$, substituted alkylamino$_{(C\leq 8)}$, dialkylamino$_{(C\leq 12)}$, substituted dialkylamino$_{(C\leq 12)}$, or —NR$_c$C(NR$_d$)R$_5$', wherein:
    R$_c$ and R$_d$ are each independently hydrogen, alkyl$_{(C\leq 6)}$, or substituted alkyl$_{(C\leq 6)}$;
    R$_5$' is amino, alkylamino$_{(C\leq 8)}$, substituted alkylamino$_{(C\leq 8)}$, dialkylamino$_{(C\leq 12)}$, or substituted dialkylamino$_{(C\leq 12)}$; and
  R$_4$ is hydrogen, alkyl$_{(C\leq 6)}$, substituted alkyl$_{(C\leq 6)}$, acyl$_{(C\leq 6)}$, or substituted acyl$_{(C\leq 6)}$;

provided that when Y$_2$ is a covalent bond, either R$_2$ is not hydroxy or R$_5$ is amino, alkylamino$_{(C\leq 8)}$, substituted alkylamino$_{(C\leq 8)}$, dialkylamino$_{(C\leq 12)}$, substituted dialkylamino$_{(C\leq 12)}$, or —NR$_c$C(NR$_d$)R$_5$';

or a pharmaceutically acceptable salt thereof.

In some embodiments, the compounds are further defined as:

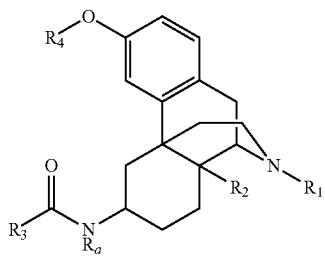

(I)

wherein:
  R$_1$ is alkyl$_{(C\leq 8)}$, cycloalkyl$_{(C\leq 8)}$, alkenyl$_{(C\leq 8)}$, or —Y$_1$—R$_1$', wherein:
    Y$_1$ is alkanediyl$_{(C\leq 8)}$ or substituted alkanediyl$_{(C\leq 8)}$; and
    R$_1$' is cycloalkyl$_{(C\leq 8)}$, aryl$_{(C\leq 12)}$, or a substituted version of either of these groups;
  R$_2$ is hydrogen, hydroxy, alkoxy$_{(C\leq 8)}$, alkenyloxy$_{(C\leq 8)}$, aryloxy$_{(C\leq 8)}$, aralkoxy$_{(C\leq 8)}$, acyloxy$_{(C\leq 8)}$, or a substituted version of any of the last five groups;
  R$_a$ is hydrogen, alkyl$_{(C\leq 6)}$, or substituted alkyl$_{(C\leq 6)}$;
  R$_3$ is a group of the formula:

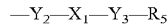

wherein:
  Y$_2$ and Y$_3$ are each independently selected from a covalent bond, alkanediyl$_{(C\leq 8)}$, or substituted alkanediyl$_{(C\leq 8)}$;
  X$_1$ is arenediyl$_{(C\leq 12)}$, heteroarenediyl$_{(C\leq 12)}$, or a substituted version of either group; and
  R$_5$ is cyano, halo, hydroxy, nitro, alkyl$_{(C\leq 8)}$, substituted alkyl$_{(C\leq 8)}$, aryl$_{(C\leq 8)}$, substituted aryl$_{(C\leq 8)}$, or —C(O)R$_b$, wherein:
    R$_b$ is hydrogen, alkyl$_{(C\leq 6)}$, or substituted alkyl$_{(C\leq 6)}$; or
  R$_5$ is amino, alkylamino$_{(C\leq 8)}$, substituted alkylamino$_{(C\leq 8)}$, dialkylamino$_{(C\leq 12)}$, substituted dialkylamino$_{(C\leq 12)}$, or —NR$_c$C(NR$_d$)R$_5$', wherein:
    R$_c$ and R$_d$ are each independently hydrogen, alkyl$_{(C\leq 6)}$, or substituted alkyl$_{(C\leq 6)}$;
    R$_5$' is amino, alkylamino$_{(C\leq 8)}$, substituted alkylamino$_{(C\leq 8)}$, dialkylamino$_{(C\leq 12)}$, or substituted dialkylamino$_{(C\leq 12)}$; and
  R$_4$ is hydrogen, alkyl$_{(C\leq 6)}$, substituted alkyl$_{(C\leq 6)}$, acyl$_{(C\leq 6)}$, or substituted acyl$_{(C\leq 6)}$; or a pharmaceutically acceptable salt thereof.

In some embodiments, the compounds are further defined as:

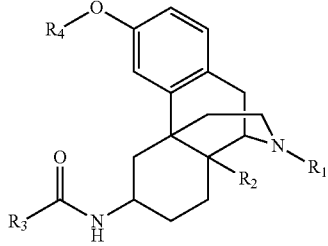

(III)

wherein:
  R$_1$ is alkyl$_{(C\leq 8)}$, cycloalkyl$_{(C\leq 8)}$, alkenyl$_{(C\leq 8)}$, or —Y$_1$—R$_1$', wherein:
    Y$_1$ is alkanediyl$_{(C\leq 8)}$ or substituted alkanediyl$_{(C\leq 8)}$; and
    R$_1$' is cycloalkyl$_{(C\leq 8)}$, aryl(C≤n), or a substituted version of either of these groups;
  R$_2$ is hydrogen, hydroxy, alkoxy$_{(C\leq 8)}$, alkenyloxy$_{(C\leq 8)}$, aryloxy$_{(C\leq 8)}$, aralkoxy$_{(C\leq 8)}$, acyloxy$_{(C\leq 8)}$, or a substituted version of any of the last five groups;
  R$_3$ is a group of the formula:

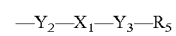

wherein:
  Y$_2$ and Y$_3$ are each independently selected from a covalent bond, alkanediyl$_{(C\leq 8)}$, or substituted alkanediyl$_{(C\leq 8)}$;
  X$_1$ is arenediyl$_{(C\leq 12)}$, heteroarenediyl$_{(C\leq 12)}$, or a substituted version of either group; and
  R$_5$ is cyano, halo, hydroxy, nitro, alkyl$_{(C\leq 8)}$, substituted alkyl$_{(C\leq 8)}$, aryl$_{(C\leq 8)}$, substituted aryl$_{(C\leq 8)}$, or —C(O)R$_b$, wherein:
    R$_b$ is hydrogen, alkyl$_{(C\leq 6)}$, or substituted alkyl$_{(C\leq 6)}$; or
  R$_5$ is amino, alkylamino$_{(C\leq 8)}$, substituted alkylamino$_{(C\leq 8)}$, dialkylamino$_{(C\leq 12)}$, substituted dialkylamino$_{(C\leq 12)}$, or —NR$_c$C(NR$_d$)R$_5$', wherein:
    R$_c$ and R$_d$ are each independently hydrogen, alkyl$_{(C\leq 6)}$, or substituted alkyl$_{(C\leq 6)}$;

$R_5'$ is amino, alkylamino$_{(C≤8)}$, substituted alkylamino$_{(C≤8)}$, dialkylamino$_{(C≤12)}$, or substituted dialkylamino$_{(C≤12)}$; and $R_4$ is hydrogen, alkyl$_{(C≤6)}$, substituted alkyl$_{(C≤6)}$, acyl$_{(C≤6)}$, or substituted acyl$_{(C≤6)}$; or a pharmaceutically acceptable salt thereof.

In some embodiments, the compounds are further defined as:

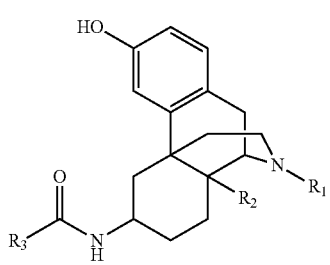

(IV)

wherein:
- $R_1$ is alkyl$_{(C≤8)}$, cycloalkyl$_{(C≤8)}$, alkenyl$_{(C≤8)}$, or —$Y_1$—$R_1'$, wherein:
  - $Y_1$ is alkanediyl$_{(C≤8)}$ or substituted alkanediyl$_{(C≤8)}$; and
  - $R_1'$ is cycloalkyl$_{(C≤8)}$, aryl$_{(C≤12)}$, or a substituted version of either of these groups;
- $R_2$ is hydrogen, hydroxy, alkoxy$_{(C≤8)}$, alkenyloxy$_{(C≤8)}$, aryloxy$_{(C≤8)}$, aralkoxy$_{(C≤8)}$, acyloxy$_{(C≤8)}$, or a substituted version of any of the last five groups; and
- $R_3$ is a group of the formula:

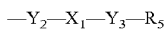

wherein:
- $Y_2$ and $Y_3$ are each independently selected from a covalent bond, alkanediyl$_{(C≤8)}$, or substituted alkanediyl$_{(C≤8)}$;
- $X_1$ is arenediyl$_{(C≤12)}$, heteroarenediyl$_{(C≤12)}$, or a substituted version of either group; and
- $R_5$ is cyano, halo, hydroxy, nitro, alkyl$_{(C≤8)}$, substituted alkyl$_{(C≤8)}$, aryl$_{(C≤8)}$, substituted aryl$_{(C≤8)}$, or —C(O)$R_b$, wherein:
  - $R_b$ is hydrogen, alkyl$_{(C≤6)}$, or substituted alkyl$_{(C≤6)}$; or
- $R_5$ is amino, alkylamino$_{(C≤8)}$, substituted alkylamino$_{(C≤8)}$, dialkylamino$_{(C≤12)}$, substituted dialkylamino$_{(C≤12)}$, or —NR$_c$C(NR$_d$)R$_5'$, wherein:
  - $R_c$ and $R_d$ are each independently hydrogen, alkyl$_{(C≤6)}$, or substituted alkyl$_{(C≤6)}$;
  - $R_5'$ is amino, alkylamino$_{(C≤8)}$, substituted alkylamino$_{(C≤8)}$, dialkylamino$_{(C≤12)}$, or substituted dialkylamino$_{(C≤12)}$;

or a pharmaceutically acceptable salt thereof.

In some embodiments, the compounds are further defined as:

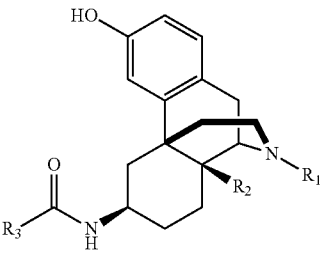

(V)

wherein:
- $R_1$ is alkyl$_{(C≤8)}$, cycloalkyl$_{(C≤8)}$, alkenyl$_{(C≤8)}$, or —$Y_1$—$R_1'$, wherein:
  - $Y_1$ is alkanediyl$_{(C≤8)}$ or substituted alkanediyl$_{(C≤8)}$; and
  - $R_1'$ is cycloalkyl$_{(C≤8)}$, aryl$_{(C≤12)}$, or a substituted version of either of these groups;
- $R_2$ is hydrogen, hydroxy, alkoxy$_{(C≤8)}$, alkenyloxy$_{(C≤8)}$, aryloxy$_{(C≤8)}$, aralkoxy$_{(C≤8)}$, acyloxy$_{(C≤8)}$, or a substituted version of any of the last five groups; and
- $R_3$ is a group of the formula:

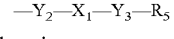

wherein:
- $Y_2$ and $Y_3$ are each independently selected from a covalent bond, alkanediyl$_{(C≤8)}$, or substituted alkanediyl$_{(C≤8)}$;
- $X_1$ is arenediyl$_{(C≤12)}$, heteroarenediyl$_{(C≤12)}$, or a substituted version of either group; and
- $R_5$ is cyano, halo, hydroxy, nitro, alkyl$_{(C≤8)}$, substituted alkyl$_{(C≤8)}$, aryl$_{(C≤8)}$, substituted aryl$_{(C≤8)}$, or —C(O)$R_b$, wherein:
  - $R_b$ is hydrogen, alkyl$_{(C≤6)}$, or substituted alkyl$_{(C≤6)}$; or
- $R_5$ is amino, alkylamino$_{(C≤8)}$, substituted alkylamino$_{(C≤8)}$, dialkylamino$_{(C≤12)}$, substituted dialkylamino$_{(C≤12)}$, or —NR$_c$C(NR$_d$)R$_5'$, wherein:
  - $R_c$ and $R_d$ are each independently hydrogen, alkyl$_{(C≤6)}$, or substituted alkyl$_{(C≤6)}$;
  - $R_5'$ is amino, alkylamino$_{(C≤8)}$, substituted alkylamino$_{(C≤8)}$, dialkylamino$_{(C≤12)}$, or substituted dialkylamino$_{(C≤12)}$;

or a pharmaceutically acceptable salt thereof.

In other embodiments, the compounds are further defined as:

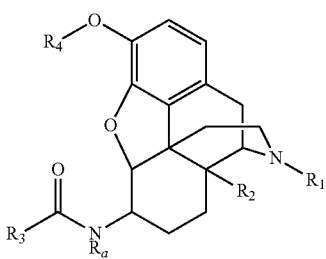

(II)

wherein:
- $R_1$ is alkyl$_{(C≤8)}$, cycloalkyl$_{(C≤8)}$, alkenyl$_{(C≤8)}$, or —$Y_1$—$R_1'$, wherein:
  - $Y_1$ is alkanediyl$_{(C≤8)}$ or substituted alkanediyl$_{(C≤8)}$; and
  - $R_1'$ is cycloalkyl$_{(C≤8)}$, aryl$_{(C≤12)}$, or a substituted version of either of these groups;

R$_2$ is hydrogen, hydroxy, alkoxy$_{(C \leq 8)}$, alkenyloxy$_{(C \leq 8)}$, aryloxy$_{(C \leq 8)}$, aralkoxy$_{(C \leq 8)}$, acyloxy$_{(C \leq 8)}$, or a substituted version of any of the last five groups;

R$_a$ is hydrogen, alkyl$_{(C \leq 6)}$, or substituted alkyl$_{(C \leq 6)}$;

R$_3$ is a group of the formula:

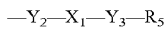

wherein:
- Y$_2$ and Y$_3$ are each independently selected from a covalent bond, alkanediyl$_{(C \leq 8)}$, or substituted alkanediyl$_{(C \leq 8)}$;
- X$_1$ is arenediyl$_{(C \leq 12)}$, heteroarenediyl$_{(C \leq 12)}$, or a substituted version of either group; and
- R$_5$ is cyano, halo, hydroxy, nitro, alkyl$_{(C \leq 8)}$, substituted alkyl$_{(C \leq 8)}$, aryl$_{(C \leq 8)}$, substituted aryl$_{(C \leq 8)}$, or —C(O)R$_b$, wherein:
  - R$_b$ is hydrogen, alkyl$_{(C \leq 6)}$, or substituted alkyl$_{(C \leq 6)}$; or
- R$_5$ is amino, alkylamino$_{(C \leq 8)}$, substituted alkylamino$_{(C \leq 8)}$, dialkylamino$_{(C \leq 12)}$, substituted dialkylamino$_{(C \leq 12)}$, or —NR$_c$C(NR$_d$)R$_5$', wherein:
  - R$_c$ and R$_d$ are each independently hydrogen, alkyl$_{(C \leq 6)}$, or substituted alkyl$_{(C \leq 6)}$;
  - R$_5$' is amino, alkylamino$_{(C \leq 8)}$, substituted alkylamino$_{(C \leq 8)}$, dialkylamino$_{(C \leq 12)}$, or substituted dialkylamino$_{(C \leq 12)}$; and R$_4$ is hydrogen, alkyl$_{(C \leq 6)}$, substituted alkyl$_{(C \leq 6)}$, acyl$_{(C \leq 6)}$, or substituted acyl$_{(C \leq 6)}$;

provided that when Y$_2$ is a covalent bond, either R$_2$ is not hydroxy or R$_5$ is amino, alkylamino$_{(C \leq 8)}$, substituted alkylamino$_{(C \leq 8)}$, dialkylamino$_{(C \leq 12)}$, substituted dialkylamino$_{(C \leq 12)}$, or —NR$_c$C(NR$_d$)R$_5$';

or a pharmaceutically acceptable salt thereof.

In some embodiments, the compounds are further defined as:

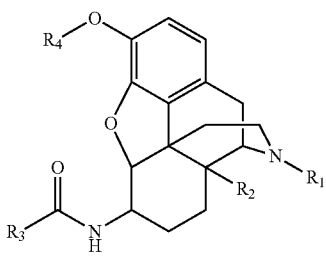

(VI)

wherein:
- R$_1$ is alkyl$_{(C \leq 8)}$, cycloalkyl$_{(C \leq 8)}$, alkenyl$_{(C \leq 8)}$, or —Y$_1$—R$_1$', wherein:
  - Y$_1$ is alkanediyl$_{(C \leq 8)}$ or substituted alkanediyl$_{(C \leq 8)}$; and
  - R$_1$' is cycloalkyl$_{(C \leq 8)}$, aryl$_{(C \leq 12)}$, or a substituted version of either of these groups;
- R$_2$ is hydrogen, hydroxy, alkoxy$_{(C \leq 8)}$, alkenyloxy$_{(C \leq 8)}$, aryloxy$_{(C \leq 8)}$, aralkoxy$_{(C \leq 8)}$, acyloxy$_{(C \leq 8)}$, or a substituted version of any of the last five groups;
- R$_3$ is a group of the formula:

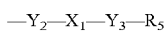

wherein:
- Y$_2$ and Y$_3$ are each independently selected from a covalent bond, alkanediyl$_{(C \leq 8)}$, or substituted alkanediyl$_{(C \leq 8)}$;
- X$_1$ is arenediyl$_{(C \leq 12)}$, heteroarenediyl$_{(C \leq 12)}$, or a substituted version of either group; and
- R$_5$ is cyano, halo, hydroxy, nitro, alkyl$_{(C \leq 8)}$, substituted alkyl$_{(C \leq 8)}$, aryl$_{(C \leq 8)}$, substituted aryl$_{(C \leq 8)}$, or —C(O)R$_b$, wherein:
  - R$_b$ is hydrogen, alkyl$_{(C \leq 6)}$, or substituted alkyl$_{(C \leq 6)}$; or
- R$_5$ is amino, alkylamino$_{(C \leq 8)}$, substituted alkylamino$_{(C \leq 8)}$, dialkylamino$_{(C \leq 12)}$, substituted dialkylamino$_{(C \leq 12)}$, or —NR$_c$C(NR$_d$)R$_5$', wherein:
  - R$_c$ and R$_d$ are each independently hydrogen, alkyl$_{(C \leq 6)}$, or substituted alkyl$_{(C \leq 6)}$;
  - R$_5$' is amino, alkylamino$_{(C \leq 8)}$, substituted alkylamino$_{(C \leq 8)}$, dialkylamino$_{(C \leq 12)}$, or substituted dialkylamino$_{(C \leq 12)}$; and R$_4$ is hydrogen, alkyl$_{(C \leq 6)}$, substituted alkyl$_{(C \leq 6)}$, acyl$_{(C \leq 6)}$, or substituted acyl$_{(C \leq 6)}$;

provided that when Y$_2$ is a covalent bond, either R$_2$ is not hydroxy or R$_5$ is amino, alkylamino$_{(C \leq 8)}$, substituted alkylamino$_{(C \leq 8)}$, dialkylamino$_{(C \leq 12)}$, substituted dialkylamino$_{(C \leq 12)}$, or —NR$_c$C(NR$_d$)R$_5$';

or a pharmaceutically acceptable salt thereof.

In some embodiments, the compounds are further defined as:

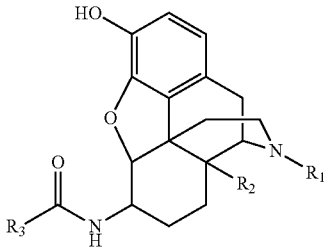

(VII)

wherein:
- R$_1$ is alkyl$_{(C \leq 8)}$, cycloalkyl$_{(C \leq 8)}$, alkenyl$_{(C \leq 8)}$, or —Y$_1$—R$_1$', wherein:
  - Y$_1$ is alkanediyl$_{(C \leq 8)}$ or substituted alkanediyl$_{(C \leq 8)}$; and
  - R$_1$' is cycloalkyl$_{(C \leq 8)}$, aryl$_{(C \leq 12)}$, or a substituted version of either of these groups;
- R$_2$ is hydrogen, hydroxy, alkoxy$_{(C \leq 8)}$, alkenyloxy$_{(C \leq 8)}$, aryloxy$_{(C \leq 8)}$, aralkoxy$_{(C \leq 8)}$, acyloxy$_{(C \leq 8)}$, or a substituted version of any of the last five groups; and
- R$_3$ is a group of the formula:

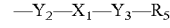

wherein:
- Y$_2$ and Y$_3$ are each independently selected from a covalent bond, alkanediyl$_{(C \leq 8)}$, or substituted alkanediyl$_{(C \leq 8)}$;
- X$_1$ is arenediyl$_{(C \leq 12)}$, heteroarenediyl$_{(C \leq 12)}$, or a substituted version of either group; and
- R$_5$ is cyano, halo, hydroxy, nitro, alkyl$_{(C \leq 8)}$, substituted alkyl$_{(C \leq 8)}$, aryl$_{(C \leq 8)}$, substituted aryl$_{(C \leq 8)}$, or —C(O)R$_b$, wherein:
  - R$_b$ is hydrogen, alkyl$_{(C \leq 6)}$, or substituted alkyl$_{(C \leq 6)}$; or
- R$_5$ is amino, alkylamino$_{(C \leq 8)}$, substituted alkylamino$_{(C \leq 8)}$, dialkylamino$_{(C \leq 12)}$, substituted dialkylamino$_{(C \leq 12)}$, or —NR$_c$C(NR$_d$)R$_5$', wherein:
  - R$_c$ and R$_d$ are each independently hydrogen, alkyl$_{(C \leq 6)}$, or substituted alkyl$_{(C \leq 6)}$;
  - R$_5$' is amino, alkylamino$_{(C \leq 8)}$, substituted alkylamino$_{(C \leq 8)}$, dialkylamino$_{(C \leq 12)}$, or substituted dialkylamino$_{(C \leq 12)}$;

provided that when $Y_2$ is a covalent bond, either $R_2$ is not hydroxy or $R_5$ is amino, alkylamino$_{(C\leq 8)}$, substituted alkylamino$_{(C\leq 8)}$, dialkylamino$_{(C\leq 12)}$, substituted dialkylamino$_{(C\leq 12)}$, or $-NR_cC(NR_d)R_5'$;

or a pharmaceutically acceptable salt thereof.

In some embodiments, the compounds are further defined as:

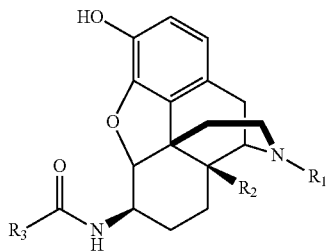
(VIII)

wherein:
- $R_1$ is alkyl$_{(C\leq 8)}$, cycloalkyl$_{(C\leq 8)}$, alkenyl$_{(C\leq 8)}$, or $-Y_1-R_1'$, wherein:
  - $Y_1$ is alkanediyl$_{(C\leq 8)}$ or substituted alkanediyl$_{(C\leq 8)}$; and
  - $R_1'$ is cycloalkyl$_{(C\leq 8)}$, aryl$_{(C\leq 12)}$, or a substituted version of either of these groups;
- $R_2$ is hydrogen, hydroxy, alkoxy$_{(C\leq 8)}$, alkenyloxy$_{(C\leq 8)}$, aryloxy$_{(C\leq 8)}$, aralkoxy$_{(C\leq 8)}$, acyloxy$_{(C\leq 8)}$, or a substituted version of any of the last five groups; and
- $R_3$ is a group of the formula:

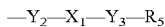
$-Y_2-X_1-Y_3-R_5$ wherein:
- $Y_2$ and $Y_3$ are each independently selected from a covalent bond, alkanediyl$_{(C\leq 8)}$, or substituted alkanediyl$_{(C\leq 8)}$;
- $X_1$ is arenediyl$_{(C\leq 12)}$, heteroarenediyl$_{(C\leq 12)}$, or a substituted version of either group; and
- $R_5$ is cyano, halo, hydroxy, nitro, alkyl$_{(C\leq 8)}$, substituted alkyl$_{(C\leq 8)}$, aryl$_{(C\leq 8)}$, substituted aryl$_{(C\leq 8)}$, or $-C(O)R_b$, wherein:
  - $R_b$ is hydrogen, alkyl$_{(C\leq 6)}$, or substituted alkyl$_{(C\leq 6)}$; or
- $R_5$ is amino, alkylamino$_{(C\leq 8)}$, substituted alkylamino$_{(C\leq 8)}$, dialkylamino$_{(C\leq 12)}$, substituted dialkylamino$_{(C\leq 12)}$, or $-NR_cC(NR_d)R_5'$, wherein:
  - $R_c$ and $R_d$ are each independently hydrogen, alkyl$_{(C\leq 6)}$, or substituted alkyl$_{(C\leq 6)}$;
- $R_5'$ is amino, alkylamino$_{(C\leq 8)}$, substituted alkylamino$_{(C\leq 8)}$, dialkylamino$_{(C\leq 12)}$, or substituted dialkylamino$_{(C\leq 12)}$;

provided that when $Y_2$ is a covalent bond, either $R_2$ is not hydroxy or $R_5$ is amino, alkylamino$_{(C\leq 8)}$, substituted alkylamino$_{(C\leq 8)}$, dialkylamino$_{(C\leq 12)}$, substituted dialkylamino$_{(C\leq 12)}$, or $-NR_cC(NR_d)R_5'$;

or a pharmaceutically acceptable salt thereof.

In some embodiments, $R_a$ is hydrogen. In some embodiments, $R_4$ is hydrogen. In some embodiments, $R_1$ is $-Y_1-R_1'$. In some embodiments, $Y_1$ is alkanediyl$_{(C\leq 8)}$ such as methylene. In some embodiments, $R_1'$ is cycloalkyl$_{(C\leq 8)}$ or substituted cycloalkyl$_{(C\leq 8)}$. In some embodiments, $R_1'$ is cycloalkyl$_{(C\leq 8)}$ such as cyclopropyl.

In some embodiments, $R_2$ is hydrogen. In other embodiments, $R_2$ is hydroxy. In other embodiments, $R_2$ is alkoxy$_{(C\leq 8)}$ or substituted alkoxy$_{(C\leq 8)}$. In some embodiments, $R_2$ is alkoxy$_{(C\leq 8)}$ such as methoxy. In some embodiments, $Y_2$ is a covalent bond. In other embodiments, $Y_2$ is alkanediyl$_{(C\leq 8)}$ or substituted alkanediyl$_{(C\leq 8)}$. In some embodiments, $Y_2$ is alkanediyl$_{(C\leq 8)}$ such as methylene.

In some embodiments, $X_1$ is arenediyl$_{(C\leq 12)}$ or substituted arenediyl$_{(C\leq 12)}$. In some embodiments, $X_1$ is arenediyl$_{(C\leq 12)}$ such as benzenediyl. In some embodiments, the $Y_3$ and $R_5$ groups are meta substituted on the $X_1$ group. In some embodiments, $Y_3$ is a covalent bond. In other embodiments, $Y_3$ is alkanediyl$_{(C\leq 8)}$ or substituted alkanediyl$_{(C\leq 8)}$. In some embodiments, $Y_3$ is alkanediyl$_{(C\leq 8)}$ such as methylene. In some embodiments, $R_5$ is amino. In other embodiments, $R_5$ is halo such as iodo. In other embodiments, $R_5$ is $-NR_cC(NR_d)R_5'$. In some embodiments, $R_c$ is hydrogen. In some embodiments, $R_1'$ is hydrogen. In some embodiments, $R_5'$ is amino. In some embodiments, the C ring adopts a chair confirmation. In some embodiments, the C ring adopts the chair confirmation when the compound is bound to the active site of an opioid receptor. In some embodiments, the C ring adopts the chair confirmation when the compound is bound to the active site of two or more opioid receptors.

In some embodiments, the compounds are further defined as:

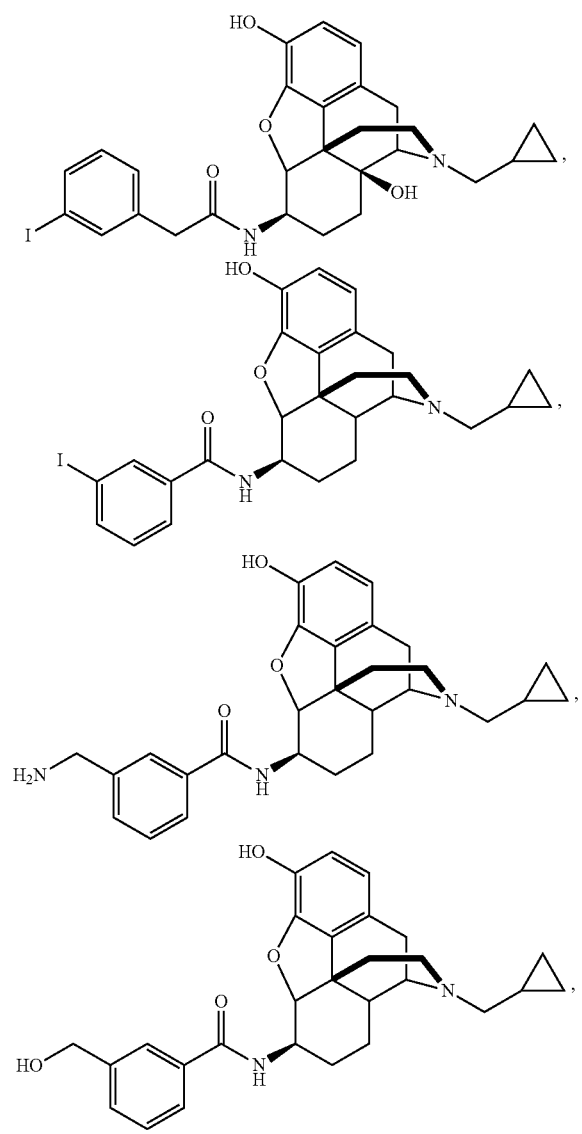

-continued

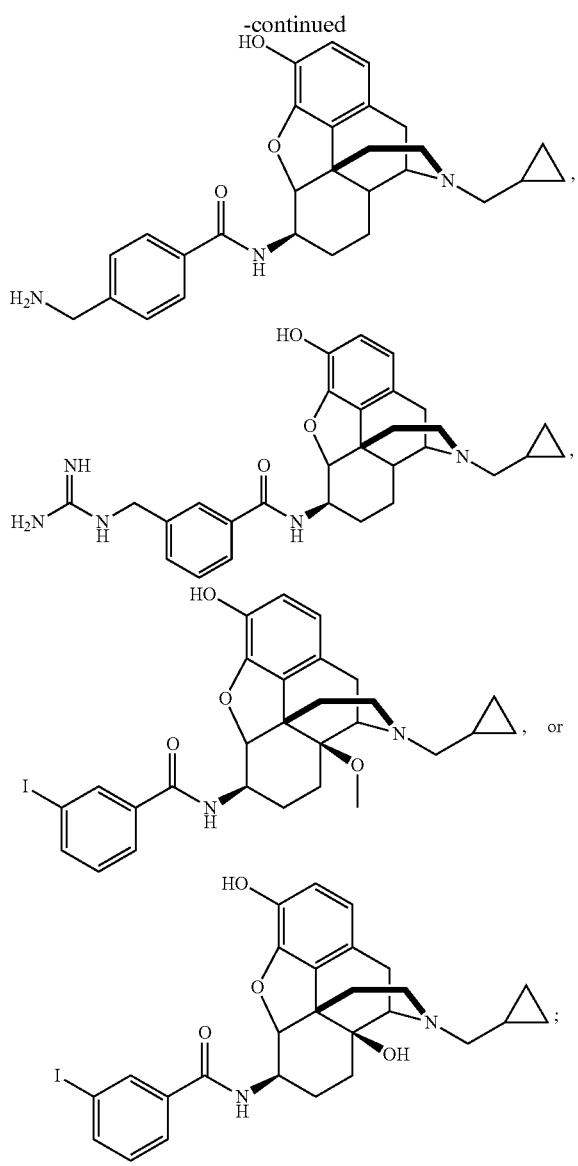

or a pharmaceutically acceptable salt thereof.

In another aspect, the present disclosure provides pharmaceutical compositions comprising:
(A) a compound described herein; and
(B) an excipient.

In some embodiments, the pharmaceutical compositions are formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularly, intravitreally, liposomally, locally, mucosally, parenterally, rectally, subconjunctivally, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion. In some embodiments, the pharmaceutical compositions are formulated for oral administration, sublingual administration, subcutaneous administration, topical administration, or intraperitoneal administration. In some embodiments, the pharmaceutical compositions are formulated as a unit dose.

In still another aspect, the present disclosure provides methods of treating a disease or disorder in a patient in need thereof comprising administering to the patient a therapeutically effective amount of a compound or composition described herein. In some embodiments, the disease or disorder causes pain. In some embodiments, the disease or disorder causes the patient to undergo a pain causing event.

In yet another aspect, the present disclosure provides methods of alleviating pain in a patient in need thereof comprising administering to the patient a therapeutically effective amount of a compound or composition described herein. In some embodiments, the pain is caused by a disease or disorder. In other embodiments, the pain is caused by a pain causing event happening to the patient. In some embodiments, the compound or composition is given before the pain causing event. In other embodiments, the compound or composition is given after the pain causing event. In some embodiments, the pain causing event is an injury. In other embodiments, the pain causing event is surgery. In some embodiments, the patient is a mammal such as a human. In some embodiments, the methods comprise administering the compound once. In other embodiments, the methods comprise administering the compound two or more times.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A & 1B MP1104 (triange) is a balanced full agonist in hMOR in cAMP inhibition and Tango-arrestin recruitment assays compared to DAMGO (circle). Gi: MP1104, $EC_{50}$=0.074 (10.13±0.05) nM, $E_{max}$=94±1 and DAMGO $EC_{50}$=0.84(9.07±0.08) nM. Arrestin: MP1104, $EC_{50}$=0.573(9.24±0.08) nM, $E_{max}$=90±2.28 and DAMGO $EC_{50}$=13.9 (7.86±0.06) nM. Bias factor toward G protein: 0.6 for MP1104, respectively (N=3) against DAMGO as a control at hMOR. FIGS. 1C & 1D MP1104 (triangle) is a balanced full agonist in hKOR in cAMP inhibition and Tango-arrestin recruitment assays compared to U50,488h (circle). Gi: MP1104, $EC_{50}$=0.00184 (11.74±0.04) nM, $E_{max}$=107±1 and U50488h $EC_{50}$=0.0768(10.11±0.04) nM. Arrestin: MP1104, $EC_{50}$=0.03944(10.4±0.06) nM, $E_{max}$=117±2 and U50,488h $EC_{50}$=3.6(8.44±0.04) nM. Bias factor toward G protein: 0.2 for MP1104, respectively (N=3) against U50,488h as a control at hKOR. FIGS. 1E & 1F The preferred docking pose of MP1104 (boat form, stick) at MOR and MP1104 (boat form, stick) in the active state of KOR. Ring-C of MP1104 in boat form forces the iodophenyl moiety to reside in a region between TM2-TM3 at MOR/KOR. FIGS. 1G & 1H MP1202 (triangle) is a G-biased full agonist in hMOR in cAMP inhibition and partial agonist in Tango-arrestin recruitment assays compared to DAMGO (circle). Gi: MP1202, $EC_{50}$=0.077 (10.11±0.06) nM, $E_{max}$=92±1.4 and DAMGO $EC_{50}$=3.78(8.4±0.06) nM. Arrestin: MP1202, $EC_{50}$=26.8(7.57±0.1) nM, $E_{max}$=53±2 and DAMGO $EC_{50}$=58.8(7.23±0.06) nM. Bias factor toward G protein: 31 for MP1202, respectively (N=3) against DAMGO as a control at hMOR. FIGS. 1I & 1J MP1202 (triangle) is a balanced full agonist in hKOR in cAMP inhibition and in Tango-arrestin recruitment assays compared to U50,488h (circle). Gi: MP1202, $EC_{50}$=0.0016 (11.8±0.05) nM, $E_{max}$=110±1 and U50,488h $EC_{50}$=0.0768 (10.11±0.04) nM. Arrestin: MP1202, $EC_{50}$=0.0457 (10.34±0.05) nM, $E_{max}$=101±1 and U50,488h $EC_{50}$=3.6 (8.44±0.04) nM. Bias factor toward G protein: 0.6 for MP1202, respectively (N=3) against U50,488h as a control at hKOR. FIGS. 1K & 1F The docking poses of MP1202 (chair form, brown stick) and (boat form, green stick) at an active states of MOR and KOR are shown. At MOR, the saturated ring C in MP1202 leads to interaction of the ligand in the ECL2 and TM5 region leading to a preference of chair form shown by an arrow. At KOR, MP1202 behaves similar to MP1104 and the flip of ring C conformation from chair to boat is shown by an arrow.

FIG. 2A MP1104 targets the TM2-TM3 region and is a balanced agonist at mMOR: The preferred docking pose of MP1104 (boat form, stick) at an active state of MOR is shown. Ring C of MP1104 in boat form forces the iodophenyl moiety to reside in a region between TM2-TM3. MP1104 (triangle) is a balanced partial agonist in mMOR in BRET assays measuring G-protein activation and arrestin recruitment compared to DAMGO (circle). Gi: MP1104, $EC_{50}$=0.66 (9.2±0.11) nM, $E_{max}$=62±2 and DAMGO $EC_{50}$=7.3 (8.1±0.07) nM. Arrestin: MP1104, $EC_{50}$=0.285 (9.55±0.12) nM, $E_{max}$=53±1.6 and DAMGO $EC_{50}$=31.5 (7.5±0.06) nM. Bias factor toward G-protein: 0.1 for MP1104, respectively (n=3) against DAMGO as a control at mMOR. FIG. 2B IBNtxA targets the TM5-ECL2 region and is G-protein biased agonist at mMOR: The docking poses of IBNtxA (chair form, stick) at an active state of MOR is shown. The saturated ringC in IBNtxA leads to interaction of the ligand in the ECL2 and TM5 region which leads to a preference of chair form in our docking studies. At mMOR, it is a G-biased partial agonist compared to DAMGO (circle) in BRET assays with Gi: $EC_{50}$=0.054 (10.3±0.02) nM, $E_{max}$=59±2.2; DAMGO, $EC_{50}$=12.9 (7.8±0.06) nM and Arrestin: IBNtxA, $EC_{50}$=11.32(4.9±0.3) μM, $E_{max}$=75±13.9; DAMGO, $EC_{50}$=0.77(6.11±0.16) μM. Bias factor toward G-protein for IBNtxA is 404 against DAMGO as a control at mMOR. FIG. 2C MP1202 targets the TM5-ECL2 region and is a G-protein biased agonist at mMOR: The preferred docking pose of MP1202 (chair form, stick) at an active state of MOR. The saturated ringC in MP1202 leads to interaction of the ligand in the ECL2 and TM5 region. MP1202 (triangle) is a G-biased partial agonist in mMOR in BRET assays measuring G-protein activation and arrestin recruitment compared to DAMGO (circle). Gi: MP1202, $EC_{50}$=0.63 (9.2±0.09) nM, $E_{max}$=61±1.5 and DAMGO $EC_{50}$=6.31 (8.2±0.07) nM. Arrestin: MP1202, $EC_{50}$=3140 (5.5±0.28) nM, $E_{max}$=53±1.6 and DAMGO $EC_{50}$=114 (6.9±0.15) nM. Bias factor toward G protein: 58 for MP1202, respectively (n=3) against DAMGO as a control at mMOR. FIG. 2D MP1207 and MP1208 target the TM5-ECL2 region and show no arrestin recruitment at mMOR: Docking results showed that m-amino methyl (MP1207) or m-guanidinomethyl (MP1208) moieties (replacing an iodo group in MP1202) forced these compounds in chair form preferred confirmation at MOR (chair form in dark stick and boat form in light stick). MP1207 (diamond) and MP1208 (triangle) are partial agonists at mMOR in BRET assays compared to DAMGO (circle). At MOR, chair forms of MP1207 and MP1208 introduce additional interactions between m-amino or m-guanidino group and $D218^{ECL2}$ and $T220^{ECL2}$. Gi: MP1207, $EC_{50}$=3.61 (8.44±0.26) nM, $E_{max}$=42±2.6; MP1208, $EC_{50}$=2.27 (8.64±0.29) nM, $E_{max}$=41±3 and DAMGO, $EC_{50}$=3.27 (8.49±0.08) nM. Arrestin: no arrestin recruitment was observed for both agonists thereby limiting to calculate their bias factors against DAMGO as a control at mMOR.

FIG. 2E MP1305 and MP1601 target the TM5-ECL2 region and show no arrestin recruitment at mMOR: Chair and boat forms of MP1305 and MP1601 at an active state MOR (in light) are shown. Docking modes of MP1305 and MP1601 are analogous and they both maintain chair confirmation at MOR and are biased towards G-protein. In BRET assays using mMOR, MP1305 (square) and MP1601 (triangle) are partial agonists compared to DAMGO (circle) with no measurable arrestin recruitment, Gi: MP1305, $EC_{50}$=0.74(9.1±0.12) nM, $E_{max}$=72±2 and DAMGO, $EC_{50}$=3.3(8.4±0.08) nM and MP1601, $EC_{50}$=2.2(8.6±0.3) nM, $E_{max}$=49±3 and DAMGO, $EC_{50}$=0.9(9.0±0.1) nM. Arrestin: no arrestin recruitment was observed for both agonists against DAMGO as a control at mMOR. Data from BRET assays using rodent opioid receptors were normalized to $E_{max}$ of the corresponding controls, DAMGO where, the dose response curves were fit using a three-parameter logistic equation in GraphPad Prism and the data are presented as mean $EC_{50}$(p$EC_{50}$±SEM) for assays run in triplicate. In summary, targeting TM5-ECL2 and ring C taking chair form leads to bias at MOR in both rodents as well as human receptors with analogs.

FIG. 3A MP1104 targets the TM2-TM3 region and is a balanced agonist at mKOR: The preferred docking pose of MP1104 (boat form, stick) at an active state of KOR is shown. The iodophenylamido moiety aligns in the hydrophobic pocket between TM2 and TM3 in KOR, a cavity lined with $V118^{2.63}$, $W124^{ECL1}$ and $L135^{3.29}$. In addition, polar residue $Q115^{2.60}$ adopts a slightly different conformation which allows more room for the hydrophobic moiety. Such increase in hydrophobic nature of the KOR binding pocket may well be associated yielding the best docking scores of MP1104 in its boat conformation. MP1104 (triangle) is a balanced full agonist in rKOR in BRET assays measuring G-protein activation and arrestin recruitment compared to U50,488H (diamond). Gi: MP1104, $EC_{50}$=0.073 (10.14±0.04) nM, $E_{max}$=93±1 and U50,488h $EC_{50}$=1.05(8.98±0.03) nM. Arrestin: MP1104, $EC_{50}$=1.14(8.94±0.07) nM, $E_{max}$=89±2.6 and U50,488h $EC_{50}$=110(6.95±0.05) nM. Bias factor toward G-protein:

0.23 for MP1104, respectively (n=3) against U50,488H as a control at hMOR. FIG. 3B IBNtxA prefers the boat form at KOR and displays balanced agonism: The docking poses of IBNtxA (chair form, light stick) and (boat form, dark stick) at an active state of KOR are shown. At KOR, the iodophenylamido moiety of IBNtxA aligns in the hydrophobic pocket between TM2 and TM3 in KOR, a cavity lined with V118$^{2.63}$, W124$^{ECL1}$ and L135$^{3.29}$. In BRET assays using rKOR, IBNtxA is a balanced agonist compared with U50, 488H (square), Gi: IBNtxA, $EC_{50}$=0.064(10.2±0.1) nM, $E_{max}$=101±2.3; U50,488H, $EC_{50}$=27.7(7.6±0.01) nM and Arrestin: IBNtxA, $EC_{50}$=1.23(8.9±0.02) nM, $E_{max}$=133±7.3; U50,488, $EC_{50}$=345.6(6.4±0.03) nM. Bias factor toward G-protein is 0.6 for IBNtxA against U50,488H as a control at rKOR. FIG. 3C MP1202 prefers the boat form at KOR and displays balanced agonism: The preferred docking pose of MP1104 (boat form, light stick) and MP1202 (chair form, dark stick) at an active state of KOR. The iodophenylamido moiety aligns in the hydrophobic pocket between TM2 and TM3 in KOR, a cavity lined with V118$^{2.63}$, W124$^{ECL1}$ and L135$^{3.29}$. In addition, polar residue Q115$^{2.60}$ adopts a slightly different conformation allowing more room for the hydrophobic moiety. Such increase in hydrophobic nature of the KOR binding pocket may well be associated yielding the best docking scores of both MP1104, IBNtxA and MP1202 with their boat conformation. MP1202 (triangle) is a balanced full agonist in rKOR in BRET assays measuring G-protein activation and arrestin recruitment compared to U50,488H (circle). Gi: MP1202, $EC_{50}$=0.134 (9.87±0.09) nM, $E_{max}$=104±2 and U50,488h $EC_{50}$=4.79 (8.32±0.07) nM. Arrestin: MP1202, $EC_{50}$=1.44(8.84±0.25) nM, $E_{max}$=77±5 and U50,488h $EC_{50}$=235(6.63±0.18) nM. Bias factor toward G-protein: 0.4 for MP1202, respectively (n=3) against U50,488H as a control at rKOR. FIG. 3D m-Aminomethyl (MP1207) and m-guanidinomethyl (MP1208) analogs prefer the chair conformation and target the TM5-ECL2 region and show no arrestin recruitment at KOR. Docking results showed that m-amino methyl (MP1207) or m-guanidinomethyl (MP1208) moieties (replacing an iodo group in MP1202) forced these compounds in chair form preferred confirmation at KOR (chair form in dark stick and boat form in light stick). Unlike boat MP1202, chair MP1207 at KOR may form a new salt bridge interaction between amino group and D223$^{5.35}$ and E209A pulling the amidophenyl moiety away from the hydrophobic pocket between TM2 and TM3. Likewise, chair MP1208 forms salt bridge interactions between guanidino group and D223$^{5.35}$ as well as with E209$^{ECL2}$. MP1207 (diamond) and MP1208 (triangle) are partial agonists at rKOR in BRET assays compared to U50,488H (big diamond). Gi: MP1207, $EC_{50}$=1.13 (8.95±0.31) nM, $E_{max}$=32±2.3; MP1208, $EC_{50}$=1.1(8.97±0.29) nM, $E_{max}$=40±2.4 and U50,488H, $EC_{50}$=82.6(7.1±0.09) nM. Arrestin: no arrestin recruitment was observed for both agonists; (n=3) against U50,488H as a control at rKOR. FIG. 3E MP1305 showed no arrestin recruitment and MP1601 was a balanced agonist at rKOR: Chair and boat forms of MP1305 and MP1601 at an active state KOR (in grey) are shown. Both MP1305 (triangle) and MP1601 (black) are partial agonists at rKOR in BRET assays compared to U50,488H (circle). Gi: MP1305, $EC_{50}$=5.04 (8.3±0.32) nM, $E_{max}$=35±3 and U50,488H, $EC_{50}$=40.3(7.4±0.07) nM; MP1601, $EC_{50}$=8.9(8.1±0.12) nM, $E_{max}$=75±3; and U50,488H, $EC_{50}$=26.7(7.6±0.09) nM. Arrestin: essentially, no arrestin recruitment was observed for MP1305 whereas for MP1601 (black), $EC_{50}$=56.5 (7.2±0.23) nM, $E_{max}$=37±3, and U50,488H, $EC_{50}$=169.6 (6.7±0.07) nM. Bias factor toward G-protein for MP1601 is 0.9 against U50,488H as a control at rKOR. Data from BRET assays using rodent opioid receptors were normalized to $E_{max}$ of the corresponding controls, U50,488H where, the dose response curves were fit using a three-parameter logistic equation in GraphPad Prism and the data are presented as mean $EC_{50}$(p$EC_{50}$±SEM) for assays run in triplicate. In summary, targeting TM5-ECL2 and ring C taking chair form leads to bias at KOR in both rodents as well as human receptors with analogs.

FIG. 4A Overview of the key hypothesis, suggesting that TM5-ECL2 engagement by morpinan ligand with ring-C chair form leads to preferred G-protein signaling, whereas TM2-TM3 engagement and ring-C boat form leads to balanced G-protein and arrestin signaling. FIG. 4B Structures of the studied m&p-substituted arylamidoepoxymorphinans (MP1104, MP1202, IBNtxA, MP1305, MP1207, MP1208, MP1209, MP1210), m-iodoarylamidomorphinan, (MP1601), and 6'GNTI.

FIGS. 5A & 5B At hMOR, IBNtxA (square) is a G-protein biased agonist compared with DAMGO (circle) Gi: $EC_{50}$=0.07 (10.2±0.006) nM, $E_{max}$=95±2; DAMGO (circle), $EC_{50}$=0.99 (9.0±0.007) nM and Arrestin: IBNtxA, $EC_{50}$=5.86 (8.2±0.002) nM, $E_{max}$=29±0.02; DAMGO, $EC_{50}$=14.16 (7.9±0.003) nM. Bias factor toward G-protein for IBNtxA is 23 against DAMGO as a control at hMOR. FIGS. 5C & 5D At hKOR, IBNtxA (circle) is a balanced agonist in cAMP inhibition and Tango-arrestin recruitment assays compared to U50,488H (square). Gi: IBNtxA, $EC_{50}$=0.47 (12.3±0.06) μM, $E_{max}$=106±0.7; U50,488H, $EC_{50}$=0.076(10.1±0.04) nM and Arrestin: IBNtxA, $EC_{50}$=0.013(10.9±0.07) nM, $E_{max}$=109±1.8; U50,488, $EC_{50}$=3.63(8.4±0.03) nM. Bias factor toward G-protein is 0.2 for IBNtxA against U50,488H as a control at hKOR. FIGS. 5F & 5G However, at mMOR, it is a G-biased partial agonist compared to DAMGO (circle) in BRET assays with Gi: $EC_{50}$=0.054(10.3±0.02) nM, $E_{max}$=59±2.2; DAMGO, $EC_{50}$=12.9(7.8±0.06) nM and Arrestin: IBNtxA, $EC_{50}$=11.32(4.9±0.3) μM, $E_{max}$=75±13.9; DAMGO, $EC_{50}$=0.77(6.11±0.16) μM. Bias factor toward G-protein for IBNtxA is 404 against DAMGO as a control at mMOR. FIGS. 5H & 5I In BRET assays using rKOR, IBNtxA is a balanced agonist compared with U50, 488H (square), Gi: IBNtxA, $EC_{50}$=0.064(10.2±0.1) nM, $E_{max}$=101±2.3; U50,488, $EC_{50}$=27.7(7.6±0.01) nM and Arrestin: IBNtxA, $EC_{50}$=1.23(8.9±0.02) nM, $E_{max}$=133±7.3; U50,488H, $EC_{50}$=345.6(6.4±0.03) nM. Bias factor toward G-protein is 0.6 for IBNtxA against U50,488H as a control at rKOR. FIGS. 5E & 5J The docking poses of IBNtxA (chair form, dark stick) and (boat form, light stick) at an active state of MOR and KOR are shown. At MOR, the saturated ring C in IBNtxA leads to interaction of the ligand in the ECL2 and TM5 region leading to a preference of chair form shown by an arrow. At KOR, the iodophenylamido moiety of IBNtxA aligns in the hydrophobic pocket between TM2 and TM3 in KOR, a cavity lined with V118$^{2.63}$, W124$^{ECL1}$ and L135$^{3.29}$ similar to MP1202. This flip of ring C conformation from chair to boat going is shown by a blue arrow. Data from both cAMP inhibition and Tango arrestin assays using human opioid receptors and BRET assays using rodent opioid receptors were normalized to $E_{max}$ of the corresponding controls, U50,488H and DAMGO. The dose response curves were fit using a three-parameter logistic equation in GraphPad Prism and the data are presented as mean $EC_{50}$(p$EC_{50}$±SEM) for assays run in triplicate. Preference for chair form correlates with G-protein bias while preference for boat form correlates with arrestin recruitment.

FIGS. 7A & 7B Unlike MP1202, MP1207 (diamond) and MP1208 (triangle) are full G protein biased agonists at hKOR in cAMP inhibition and Tango-arrestin recruitment assays compared to U50, 488 (circle). Gi: MP1207, $EC_{50}$=0.11 (9.98±0.07) nM, $E_{max}$=90±1.7; MP1208, $EC_{50}$=0.14 (9.9±0.07) nM, $E_{max}$=96±1.9; and U50,488, $EC_{50}$=0.64(9.2±0.06) nM. Arrestin: MP1207, $EC_{50}$=3.97(8.4±0.18) nM, $E_{max}$=37±2, MP1208, $EC_{50}$=16.41(7.79±0.14) nM, $E_{max}$=48±2.4, and U50,488, $EC_{50}$=7.55(8.12±0.06) nM. Bias factor toward G protein: 8 and 23 for MP1207 and MP1208 respectively against U50,488 as a control at hKOR. FIGS. 7C & 7D Docking results showed that amino methyl (MP1207) or guanidino (MP1208) moieties (replacing an iodo group in MP1202) forced these compounds in chair form preferred confirmation at hKOR (chair form in dark stick and boat form in light stick). Unlike boat MP1202, chair MP1207 at hKOR may form a new salt bridge interaction between amino group and $D223^{5.35}$ and $E209^{ECL2}$ pulling amidophenyl moiety away from the hydrophobic pocket between TM2 and TM3 (FIG. 7C). Likewise, chair MP1208 forms salt bridge interactions between guanidino group and $D223^{5.35}$ as well as with $E209^{ECL2}$ FIG. 7D The flip in conformation of ringC from boat to chair for both MP1207 and MP1208 is shown by an arrow. FIGS. 7E & 7F MP1207 (diamond) and MP1208 (triangle) are partial agonists at hMOR in cAMP inhibition and Tango-arrestin recruitment assays compared to DAMGO (circle). Gi: MP1207, $EC_{50}$=0.034 (10.47±0.15) nM, $E_{max}$=33±1.4; MP1208, $EC_{50}$=0.008 (8.73±0.12) nM, $E_{max}$=42±1.3; and DAMGO, $EC_{50}$=1.86 (8.73±0.06) nM. Arrestin: Essentially, no arrestin recruitment was observed for both agonists MP1207 and MP1208 thereby limiting calculation of their bias factors against DAMGO as a control at hMOR FIGS. 7E & 7F Similarly, MP1207 (diamond) and MP1208 (triangle) are partial agonists at mMOR in BRET assays compared to DAMGO (circle). Gi: MP1207, $EC_{50}$=3.61 (8.44±0.26) nM, $E_{max}$=42±2.6; MP1208, $EC_{50}$=2.27 (8.64±0.29) nM, $E_{max}$=41±3 and DAMGO, $EC_{50}$=3.27(8.49±0.08) nM. Arrestin: no arrestin recruitment was observed for both agonists thereby limiting to calculate their bias factors against DAMGO as a control at mMOR.

FIGS. 7G & 7H At AMOR chair forms of MP1207 and MP1208 introduce additional interactions between amino or guanidino group and $D218^{ECL2}$ and $T220^{ECL2}$. Thus, biased signaling events of MP1207 and MP1208 are dictated from chair favored binding via the involvement of their m-amino or m-guanidino group with TM5-ECL2 region.

FIGS. 8A & 8C At Y312W-hKOR, MP1202 (triangle) is a G-biased agonist in cAMP inhibition FIG. 8A and Tango-arrestin recruitment assays FIG. 8C compared to U50,488H (circle). Gi: MP1202, $EC_{50}$=0.21 (10.69±0.07)μM, $E_{max}$=101±1.5; U50,488H, $EC_{50}$=2.7(8.56±0.06) nM and Arrestin: MP1202, $EC_{50}$=3.4(8.5±0.14) nM, $E_{max}$=55±2.6; U50,488H, $EC_{50}$=0.63(7.2±0.06) nM. Bias factor toward G-protein is 34 for MP1202 against U50,488H as a control at Y312W-hKOR. FIG. 8B At WT-hKOR, Arrestin: MP1202 (diamond), $EC_{50}$=0.0457(10.34±0.05) nM, $E_{max}$=101±1 and U50,488h (triangle) $EC_{50}$=3.6(8.44±0.04) nM. Bias factor toward G-protein: 0.6 for MP1202, respectively (n=3) against U50,488H as a control at WT-hKOR. FIG. 8D At WT-hMOR, Arrestin: MP1202 (triangle), $EC_{50}$=26.8 (7.57±0.1) nM, $E_{max}$=53±2 and DAMGO (circle) $EC_{50}$=58.8(7.23±0.06) nM. Bias factor toward G-protein: 31 for MP1202, respectively (n=3) against DAMGO as a control at hMOR. FIGS. 8E & 8G At Y312W-hKOR, MP1207 (light green) and 1208 (dark green) show full agonism in cAMP inhibition FIG. 8E and reduced arrestin measurement in Tango-arrestin recruitment assays FIG. 8G compared to U50,488H (circle). Gi: MP1207, $EC_{50}$=0.16 (9.8±0.08) nM, $E_{max}$=95±1.8; MP1208, $EC_{50}$=0.36 (10.44±0.05)μM, $E_{max}$=97±1; U50,488H, $EC_{50}$=0.92(9.04±0.04) nM and Arrestin: MP1207&1208, $EC_{50}$=nd, $E_{max}$=nd; U50,488H, $EC_{50}$=14(7.85±0.1) nM. FIG. 8F At WT-KOR, Arrestin: MP1207 (diamond), $EC_{50}$=3.97(8.4±0.18) nM, $E_{max}$=37±2, MP1208 (triangle), $EC_{50}$=16.41(7.79±0.14) nM, $E_{max}$=48±2.4, and U50,488H (circle), $EC_{50}$=7.55 (8.12±0.06) nM. Bias factor toward G-protein: 8 and 23 for MP1207 and MP1208 respectively against U50,488H as a control at hKOR. FIG. 8H At WT-MOR, Arrestin: Essentially, no arrestin recruitment was observed for both agonists MP1207 and MP1208 thereby limiting calculation of bias factors against DAMGO as a control at hMOR. Data from both cAMP inhibition and Tango arrestin assays using human opioid receptors were normalized to $E_{max}$ of the corresponding standards, U50,488H and DAMGO. The dose response curves were fit using a three-parameter logistic equation in GraphPad Prism and the data are presented as mean $EC_{50}(pEC_{50}±SEM)$ for assays run in triplicate FIG. 8J Conformation of selected residues seen in high resolution active state MOR structure along with crystallographic waters around TM2-TM3 region and crystallized ligand (BU72). MOR, conformation of conserved $Q^{2.60}$ is maintained by a rather extensive hydrogen-bonding network mediated by $W^{7.35}$ and at least four tightly bound waters as found in the crystal structure FIG. 8J Conformation of selected residues and MP1202 seen in active state KOR structure, along with modeled waters around TM2-TM3 region, in KOR no crystallographic waters were resolved in the structure, the non-conserved residues, including $Y^{7.35}$ instead of $W^{7.35}$, would rearrange water network and change conformation of $Q^{2.60}$, paramount for ligand binding. A theoretical water network was modeled using SampleFlood method of ICM Molsoft in the orthosteric ligand site, and resulting waters were optimized via several rounds of extensive conformational sampling. As a result of significant difference observed in the water network, compared to MOR, KOR's $Q115^{2.60}$ moves further inwards and is positioned between $D138^{3.32}$ and $Y312^{7.43}$, and this new position of $Q115^{2.60}$ is stabilized via a water-mediated hydrogen bond with $Y312^{7.35}$. FIG. 8K Docking poses of chair and boat conformations of MP1202 in Y312W KOR mutant. The chair form (−56.53) is favored over boat form (−53.75) at this mutant receptor for MP1202.

FIGS. 9A & 9B MP1209 (triangle) and MP1210 (upside down triangle) are balanced agonists at hKOR in cAMP inhibition and Tango-arrestin recruitment assays compared to U50,488 (circle). Gi: MP1209, $EC_{50}$=0.024 (10.6±0.05) nM, $E_{max}$=100±1.23, MP1210, $EC_{50}$=0.025 (10.6±0.05) nM, $E_{max}$=101.1±1.1 and U50,488, $EC_{50}$=0.05 (10.29±0.06) nM. Arrestin: MP1209, $EC_{50}$=0.37(9.43±0.19) nM, $E_{max}$=67±3, MP1210, $EC_{50}$=1.16 (8.94±0.17) nM, $E_{max}$=63±3.3 and U50,488, $EC_{50}$=7.85 (8.11±0.1) nM. Bias factor toward G protein for MP1209 and MP1210 are 0.6 and 1.2 against U50,488 as a control at hKOR. FIGS. 9C & 9D Similarly, MP1209 (triangle) and MP1210 (square) are full agonists at hMOR in cAMP inhibition and Tango-arrestin recruitment assays compared to DAMGO (circle). Gi: MP1209, $EC_{50}$=0.25(9.61±0.04) nM, $E_{max}$=98.5±0.96, MP1210, $EC_{50}$=0.15(9.81±0.05) nM, $E_{max}$=94.6±0.98, and DAMGO, $EC_{50}$=0.2 (9.7±0.06) nM. Arrestin: Essentially, no arrestin recruitment was observed for both agonists MP1209 and MP1210 thereby limiting calculation of bias factors against DAMGO as a control at hMOR. Regioselectivity of ring substituent is important for kappa bias. The p-methyl amino and m-methyl alcohol do not form salt-bridge within TM5-ECL2 unlike the m-methyl amino group of MP1207 as a result similar to MP1202 with respect to bias at KOR and MOR.

FIGS. 10A & 10B MP1305 (triangle) is a balanced agonist at hKOR in cAMP inhibition and Tango-arrestin recruitment assays compared to U50,488H (circle). Gi: MP1305, $EC_{50}$=0.72 (9.14±0.05) nM, $E_{max}$=102±1.2 and U50,488H, $EC_{50}$=0.076(10.11±0.04) nM. Arrestin: MP1305, $EC_{50}$=25.72(7.6±0.04) nM, $E_{max}$=75±1 and U50,488H, $EC_{50}$=3.6(8.44±0.04) nM. Bias factor toward G-protein for MP1305 is 4 against U50,488H as a control at hKOR. FIGS. 10C & 10D Similarly, MP1305 (triangle) is a full agonist at hMOR in cAMP inhibition and Tango-arrestin recruitment assays compared to DAMGO (circle). Gi: MP1305, $EC_{50}$=0.12(9.9±0.12) nM, $E_{max}$=69±1.8 and DAMGO, $EC_{50}$=3.88(8.4±0.05) nM. Arrestin: MP1305, $EC_{50}$=16.4(7.8±0.3) nM, $E_{max}$=21±3 and DAMGO, $EC_{50}$=168.1(6.77±0.09) nM. Bias factor toward G-protein for MP1305 is 11 against DAMGO as a control at hMOR. FIGS. 10E & 10F MP1601 (upside down triangle) is a balanced agonist at hKOR in cAMP inhibition and Tango-arrestin recruitment assays compared to U50,488H (circle). Gi: MP1601, $EC_{50}$=0.17(9.76±0.05) nM, $E_{max}$=109±1 and U50,488H, $EC_{50}$=0.077(10.11±0.04) nM. Arrestin: MP1601, $EC_{50}$=3.23(8.49±0.07) nM, $E_{max}$=107±3 and U50,488H, $EC_{50}$=3.6(8.44±0.04) nM. Bias factor toward G-protein for MP1601 is 0.15 against U50,488H as a control at hKOR. FIGS. 10G & 10H Similarly, MP1601 (diamond) is a partial agonist at hMOR in cAMP inhibition and Tango-arrestin recruitment assays compared to DAMGO (circle). Gi: MP1601, $EC_{50}$=0.1(9.99±0.09) nM, $E_{max}$=69±1 and DAMGO, $EC_{50}$=3.88(8.4±0.05) nM. Arrestin: MP1601, $EC_{50}$=4.02(8.4±0.2) nM, $E_{max}$=27±2 and DAMGO, $EC_{50}$=168.1(6.77±0.09) nM. Bias factor toward G-protein for MP1601 is 4 against DAMGO as a control at hMOR. The data were normalized to $E_{max}$ of U50,488H and dose response curves were fit using a three-parameter logistic equation in GraphPad Prism; data are presented as mean $EC_{50}$($pEC_{50}$±SEM) for assays run in triplicate. FIGS. 10I & 10J Molecular docking of MP1305 and MP1601 with a chair (dark stick) or a boat confirmation (light stick) at hKOR and hMOR. FIGS. 10K & 10L Chair and boat forms of MP1305 and MP1601 at an active state hKOR (in gray) and Chair and boat forms of MP1305 and MP1601 at an active state hMOR (in light). Preferred docking modes of MP1305 and MP1601 are analogous and they both maintain chair confirmation at hMOR and are biased towards G-protein, while being balanced agonists at hKOR taking boat conformation.

FIGS. 11A & 11B MP1202 in KOR favors boat conformation. FIGS. 11C & 11D MP1305 in KOR favors chair conformation. $14^{th}$-position-Methoxy of MP1305 causes sidechain of $Q115^{2.60}$ residue to undergo a conformational change, when compared to ligands with non-Methoxy substitutions at 14th-position (shown in light carbon sticks representation). FIG. HE IBNtxA in KOR favors boat conformation. FIG. 11F Stabilization of IBNtxA in boat form through internal hydrogen-bonding between 14-OH and amide and with $Q115^{2.60}$ is shown. The docked and energy minimized pose of MP1305 shows the substitution of 14-OH with larger methoxy group displaces the conserved $Q115^{2.60}$ of KOR. In ligands with 14-OH, the $Q115^{2.60}$ residue of KOR is directed towards the ligand and forms hydrogen bonds with the 14-OH. In the case of MP1305, the methoxy group pushes $Q115^{2.60}$ residue away to avoid steric clashes, and the polar terminus of the side chain ends up in the previously hydrophobic TM2-TM3 subpocket of KOR. Furthermore, due to internal ligand sterics, the internal hydrogen bond between the amide and 14-OH, as seen in compounds such as IBNtxA (FIGS. 11E & 11F), is not possible for MP1305. The combination of these two factors, increasing polarity of the hydrophobic TM2-TM3 subpocket (an effect similar to $Y312W^{6.35}$ KOR sub-pocket mutation-See FIG. 8) and lack of an internal hydrogen bond stabilizing the boat form, shifts the equilibrium towards the chair form for MP1305.

FIG. 12A Dose-response curve: Groups of C57BL/6J mice were supraspinally (dev) administered MP1207, MP1208, morphine and U50,488h and antinociception measured using the 55° C. tail withdrawal assay. $ED_{50}$ (with 95% CI)=6.1 nmol (4.1, 8.9), 19.8 nmol (12.6-34.0), 2.35 nmol (1.13-5.03) and 8.62 nmol (5.74-11.9) nmol was determined for MP1207, MP1208, morphine and U50,488h respectively. The means of each point in each determination were calculated as percentage maximal possible effect (% MPE) [(observed latency−baseline latency)/(maximal latency−baseline latency)]×100.

Points represent mean±SEM. FIG. 12B MP1207 analgesia in KO mice: Analgesic effect of MP1207 (30 nmol iev) was evaluated in group of (n=8) in two independent experiments of WT, MOR KO, KOR KO, and DOR KO mice. Antinociception of MP1207 remained intact in DOR KO mice while it was found attenuated in MOR KO and KOR KO mice. Results were analyzed with one-way ANOVA followed by Tukey's multiple comparisons test, $F_{3,28}$=10.11, p=0.0001.p=0.0093 relative to WT, *p=0.0002 relative to WT, ns=p>0.05 relative to WT. All values are expressed as the mean±SEM. FIG. 12C Conditioned place preference or aversion (CPP/CPA): The baseline preferences were determined for 20 min as the pre-condition test prior to the administration of a drug on the conditioning day. C57 mice (n=18-24) were conditioned for 20 minutes on each session with either saline, morphine (10 mg/kg, IP), U50,488h (30 mg/kg, IP), or MP1207 (100 nmol iev) after being habituated for one hour. On the postconditioning testing day, animals were placed in the side paired with saline and allowed to freely explore both compartments for 20 min. The difference score was calculated by subtracting the time spent in each compartment postconditioning to that of the corresponding compartment during preconditioning. The MP1207 did not display GPP seen with morphine or CPA behavior seen with U50, 488h; (P<0.05) as determined by ANOVA followed by Tukey's multiple-comparison test. FIG. 12D Respiratory rate: An average breath rate of a groups of C57 mice was measured every 20 min for 180 min to determine a percent baseline prior to the drug administration. Mice were administered either saline (n=15), morphine (10 mg/kg, IP or 30 nmol, iev; n=15, each dose), or MP1207 (30 or 100 nmol, iev, n=15, each dose) and the breath rates was measured every 20 min for 180 minutes. Morphine caused significant reduction in respiratory rates whereas MP1207 displayed an increase in the respiratory rate at a lower dose (30 nmol, iev) and showed a slight right shift of effect at higher dose (100 nmol, iev). FIG. 12E Locomotor effect: A groups of C57/B6 mice (n=15) were dosed with either saline, morphine (30 or 100 nmol, icv) or MP1207 (30 or 100 nmol, icv) and the distance travelled by each group of mice was measured. An increase in the forward locomotory effect was observed in MP1207 (30 or 100 nmol, icv) dosed mice.

DESCRIPTION OF ILLUSTRATIVE EMBODIMENTS

Figures 1A, 1B, 1C, 1D, 1E, 1F, 1G, 1H, 1I, 1J, 1K, 1L:
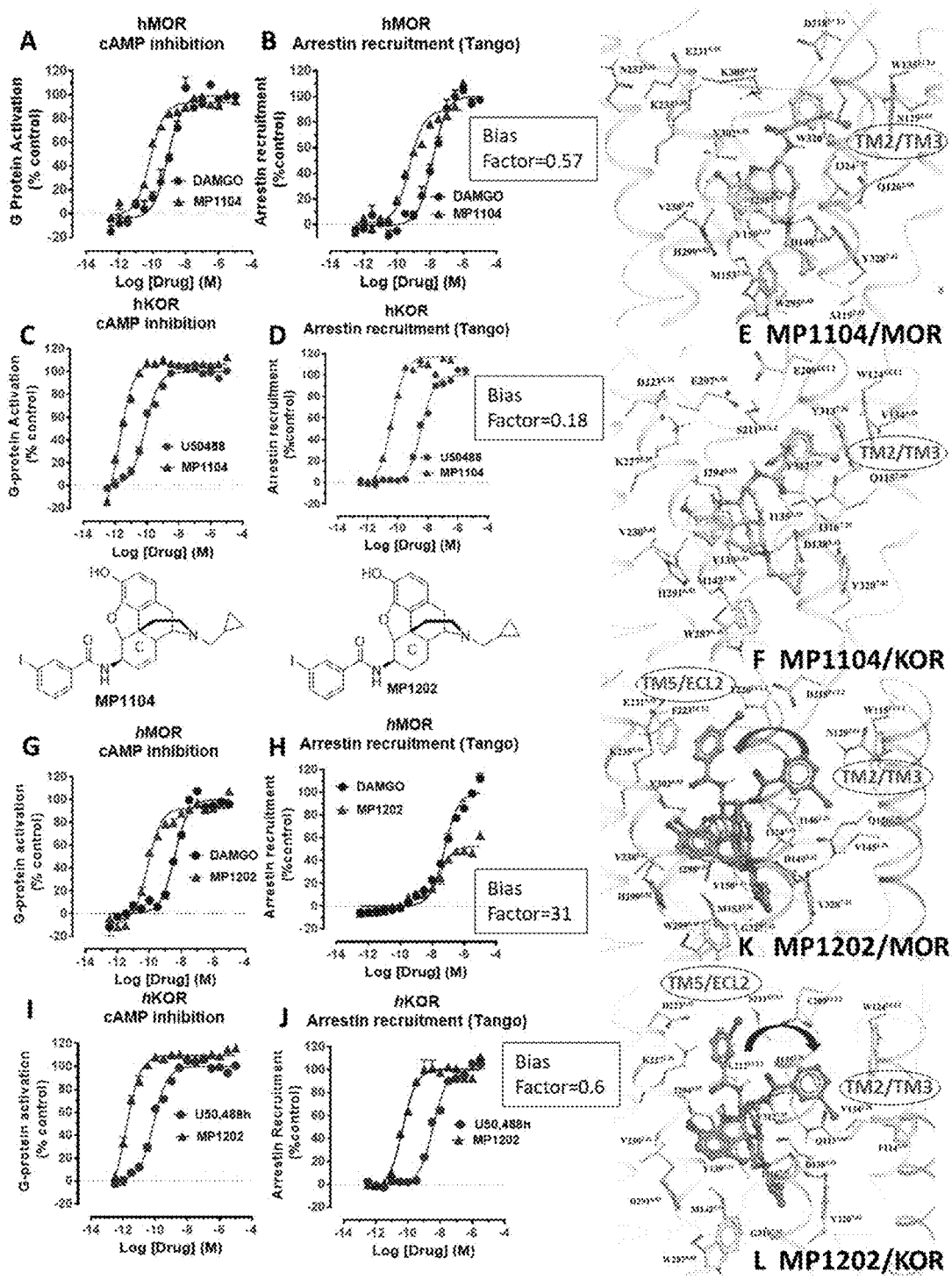
FIGS. 1A-1L show MP1104 targets the TM2-TM3 region and is a balanced agonist at both MOR and KOR, whereas MP1202 targets the TM5-ECL2 region is G-protein biased at MOR while being a balanced agonist at KOR targeting TM2-TM3.

Described herein are a series of compounds which show an improved pharmaceutical profile such as shown reduced activation of beta-arrestin. Without wishing to be bound by any theory, it is believed that these compounds may have a C ring which preferentially binds to an opioid receptor in the chair confirmation rather than in the boat confirmation. In particular, these compounds may show reduced side effects such as reduced respiratory depression or may be less addictive than other opioids currently in clinical use. These and other aspects of the present disclosure are described in the claims and the following sections.

I. Opioids and Opioid Receptors

A. Opioids

Opiates are drugs derived from opium and include morphine, codeine and a wide variety of semisynthetic opioid congeners derived from these and from the baine, another component of opium. Opioids include the opiates and all agonists and antagonists with morphine-like activity and naturally occurring endogenous and synthetic opioid peptides. Although morphine and other morphine-like opioid agonists are commonly used to produce analgesia, the severity and high incidence of side effects limits their clinical use.

There are now many compounds with pharmacological properties similar to those produced by morphine, but none has proven to be clinically superior in relieving pain. The effects of morphine on human beings are relatively diverse and include analgesia, drowsiness, mood changes, respiratory depression, decreased gastrointestinal motility, nausea, vomiting, and alterations of the endocrine and autonomic nervous systems. Pasternak (1993) Clin. Neuropharmacol. 16:1. Doses of morphine need to be tailored based on individual sensitivity to the drug and the pain-sparing needs of the individual. Likewise, responses of an individual patient can vary dramatically with different morphine-like drugs and patients can have side effects with one such drug and not another. For example, it is known that some patients who are unable to tolerate morphine may have no problems with an equianalgesic dose of methadone. The mechanisms underlying individual variations in response to morphine and morphine-like agonists have not been defined.

The analgesic effects of morphine are transduced through opioid receptors in the central nervous system (CNS), located at both spinal and multiple supraspinal sites. Morphine and its agonists induce profound analgesia when administered intrathecally or instilled locally into the dorsal horn of the spinal cord. Recently, it has been shown that opioids elicit analgesia at peripheral sites and therefore, topical administration of morphine is also effective in modulating pain. Several mechanisms of action are believed to mediate the inhibition of nociceptive reflexes from reaching higher centers of the brain, including the inhibition of neurotransmitter release by opioid receptors on the termini of primary afferent nerves and post-synaptic inhibitory actions on interneurons and on the out-put neurons of the spinothalamic tract.

Opiates can interfere with normal gastrointestinal activity such as decreases both gastric motility and stomach secretion of hydrochloric acid. For example, morphine can delay passage of gastric contents through the duodenum for as long as 12 hours. Morphine also decreases biliary, pancreatic, and intestinal secretions and delays the digestion of food in the small intestine. Often, the propulsive peristaltic waves in the colon are diminished or abolished when morphine is used resulting commonly in constipation. For a detailed review of the physiologic effects of morphine, see Reisine and Pasternak (1996) Goodman & Gilman's, The pharmacological basis of therapeutics, Ninth Edition (Hardman et al. eds.) McGraw-Hill pp. 521-555.

Side effects resulting from the use of morphine range from mild to life-threatening. Morphine causes constriction of the pupil by an excitatory action on the parasympathetic nerve innervating the pupil. Morphine depresses the cough reflex through inhibitory effects on the cough centers in the medulla. Nausea and vomiting occur in some individuals through direct stimulation of the chemoreceptor trigger zone for emesis, in the postrema of the medulla. Therapeutic doses of morphine also result in peripheral vasodilatation, reduced peripheral resistance and inhibition of baroreceptor reflexes in the cardiovascular system.

Additionally, morphine provokes the release of histamines, which can cause hypotension. Morphine depresses respiration, at least in part by direct effects on brainstem regulatory systems. In humans, death from morphine poisoning is nearly always due to respiratory arrest. Opioid antagonists can produce a dramatic reversal of severe respiratory depression; naloxone is currently the treatment of choice. High doses of morphine and related opioids can produce convulsions that are not always relieved by naloxone.

The development of tolerance and physical dependence with repeated use is a characteristic feature of all opiates. Dependence seems to be closely related to tolerance, since treatments that block tolerance to morphine also block dependence. In vivo studies in animal models demonstrate the importance of neurotransmitters and their interactions with opioid pathways in the development of tolerance to morphine. Blockade of glutamate actions by noncompetitive and competitive NMDA (N-methyl-D-aspartate) antagonists blocks morphine tolerance. Trujillo and Akil (1991) Science 251:85; Elliott et al. (1994) Pain 56:69; U.S. Pat. Nos. 5,654,281; 5,523,323; and 5,321,012; and WO/98/14427. NMDA antagonists include, but are not limited to, dextromethorphan, dextrorphan, ketamine, pyroloquinoline quinone, cA-4-(phosphonomethyl)-2-piperdine carboxylic acid, and MK801. Blockade of the glycine regulatory site on NMDA receptors exerts similar effects to block tolerance. Kolesnikov et al. (1994) Life Sci. 55:1393. Administering inhibitors of nitric oxide synthase in morphine-tolerant animals reverses tolerance, despite continued opioid administration. Kolesnikov et al. (1993) Proc. Natl. Acad. Sci. USA 90:5162.

These studies illustrate several important aspects of tolerance and dependence. First, the selective actions of drugs on tolerance and dependence demonstrate that analgesia can be dissociated from these two unwanted actions. Second, the reversal of preexisting tolerance by NMDA antagonists and nitric oxide synthase inhibitors indicates that tolerance is a balance between activation of processes and reversal of those processes. These observations suggest that, by use of selective agonists and/or antagonists, tolerance and dependence in the clinical management of pain can be minimized or disassociated from the therapeutic effects. Unfortunately, NMDA antagonists are difficult to administer systemically due to their profound psychomimetic and dysphoric actions.

In addition to morphine, a variety of opioids are suitable for clinical use. These include, but are not limited to, Levorphanol, Meperidine, Fentanyl, Methadone, Codeine, Propoxyphene and various opioid peptides. Certain opioids are mixed agonists/antagonists and partial agonists. These include pentazocine, nalbuphine, butorphanol, and buprenorphine.

The pharmacological effects of levorphanol closely parallel those of morphine although clinical reports suggest that levorphanol produces less nausea. Dextromethorphan, the d-isomer of the codine analog of levorphanol, has been used specifically for the treatment of mouth pain. See, U.S. Pat. No. 4,446,140.

Meperidine exerts its chief pharmacological effects on the CNS and the neural elements in the bowel. Meperidine produces a pattern of effects similar, but not identical to, those described for morphine. In equianalgesic doses, meperidine produces as much sedation, respiratory depression, and euphoria as morphine. The pattern of unwanted side effects that follows the use of meperidine are similar to those observed after equianalgesic doses of morphine, except that constipation and urinary retention are less common.

Fentanyl is a synthetic opioid estimated to be 80 times as potent as morphine as an analgesic. High doses of fentanyl can result in severe toxicity and produce side effects including muscular rigidity and respiratory depression.

Methadone is an opioid with pharmacologic properties similar to morphine. The pharmacologic properties of methadone include effective analgesic activity, efficacy by the oral route and persistent effects with repeated administration. Side effects include detection of miotic and respiratory-depressant effects for more than 24 hours after a single dose, and, marked sedation is seen in some patients. Effects on cough, bowel motility, biliary tone and the secretion of pituitary hormones are qualitatively similar to those of morphine. In contrast to morphine, codeine is approximately 60% as effective orally as parenterally, both as an analgesic and as a respiratory depressant.

Codeine has an exceptionally low affinity for opioid receptors, the analgesic effect of codeine is due to its conversion to morphine. However, codeine's antitussive actions probably involve distinct receptors that specifically bind codeine.

Propoxyphene produces analgesia and other CNS effects that are similar to morphine. It is likely that at equianalgesic doses the incidence of side effects such as nausea, anorexia, constipation, abdominal pain, and drowsiness would be similar to those of codeine.

B. Opioid Receptors

Opioid receptors comprise a family of cell surface proteins, which control a range of biological responses, including pain perception, modulation of affective behavior and motor control, autonomic nervous system regulation and neuroendocrinologic function. There are three major classes of opioid receptors in the CNS, designated mu, kappa and delta, which differ in their affinity for various opioid ligands and in their cellular distribution. The different classes of opioid receptors are believed to serve different physiologic functions. Olson et al. (1989) Peptides 10:1253; Lutz and Pfister (1992) J. Receptor Res. 12:267; and Simon (1991) Medicinal Res. Rev. 11:357. Opiates, such as morphine, produces analgesia primarily through the mu-opioid receptor. However, among the opioid receptors, there is substantial overlap of function as well as of cellular distribution.

The mu-opioid receptor mediates the actions of morphine and morphine-like opioids, including most clinical analgesics. In addition to morphine, several highly selective agonists have been developed for mu-opioid receptors, including [D-Ala$^2$,MePhe$^4$,Gly(ol)$^5$] enkephalin (DAMGO), levorphanol, etorphine, fentanyl, sufentanil, bremazocine and methadone. Mu-opioid receptor antagonists include naloxone, naltrexone, D-Phe-Cys-Try-D-Trp-Om-Thr-Pen-Thr-NH$_2$ (CTOP), diprenorphine, β-funaltrexamine, naloxonazine, nalorphine, nalbuphine, and naloxone benzoylhydrazone. Differential sensitivity to antagonists, such as naloxonazine, indicates the pharmacologic distinctions between the mu-opioidreceptor subtypes, mu$_1$, and mu$_2$. Several of the opioid peptides also interact with mu-opioid receptors.

There are three known kappa-opioid receptor subtypes, designated kappa$_1$, kappa$_2$ and kappa$_3$. Each kappa-opioid receptor subtype possesses distinct pharmacologic properties. For example, kappa$_1$-opioid receptors produce analgesia spinally and kappa$_3$-opioid receptors relieve pain through supraspinal mechanisms. In addition, the kappa$_1$-opioid receptor selectively binds to the agonist U50,488. Additional agonists of the kappa$_1$-opioid receptor include etorphine; sufentanil; butorphanol; β-funaltrexamine; nalphorine; pentazocine; nalbuphine; bremazocine; ethylketocyclazocine; U50,488; U69,593; spiradoline; and nor-binaltorphimine. Agonists of the kappa$_3$-opioid receptor include etorphine; levorphanol; DAMGO; nalphorine; nalbuphine; naloxone benzoylhydrazone; bremazocine; and ethylketocyclazocine. Effects of agonists on the kappa$_1$-opioidreceptors are reversed by a number of antagonists, including buprenorphine, naloxone, naltrexone, diprenorphine, naloxonazine, naloxone benzoylhydrazone, naltrindole and nor-binaltorphimine. Antagonists of the kappa$_3$-opioid receptors include naloxone, naltrexone and diprenorphine.

The delta-opioid receptors are divided into two subclasses, delta$_1$ and delta$_2$. The delta opioid receptors modulate analgesia through both spinal and supraspinal pathways.

The two subclasses were proposed based on their differential sensitivity to blockade by several novel antagonists. Portoghese et al. (1992) Eur. J. Pharmacol. 218:195; and Sofuoglu et al. (1991) J. Pharmacol. Ther. 257:676. The agonists [D-Pro$^2$,Glu$^4$] deltorphin and [D-Ser$^2$,Leu$^5$]enkephalin-Thr$^6$ (DSLET) preferentially bind to the delta$_2$ receptors, whereas [D-Pen$^2$,D-Pen$^5$]enkephalin (DPDPE) has a higher affinity for delta$_1$ receptors.

There are three distinct families of endogenous opioid peptides, the enkephalins, endorphins and dynorphins. Each such peptide is derived from a distinct precursor polypeptide. Mu-opioid receptors have a high affinity for the enkephalins as well as β-endorphin and dynorphin A. The enkephalins are also endogenous ligands for the delta receptors, along with dynorphin A and dynorphin B. The kappat-opioidreceptor endogenous opioid peptide agonists include dynorphin A, dynorphin B and α-neoendorphin. See Reisine and Pasternak (1996).

Members of each known class of opioid receptor have been cloned from human cDNA and their predicted amino acid sequences have been determined. Yasuda et al. (1993) Proc. Natl. Acad. Sci. USA 90:6736; and Chen et al. (1993) Mol. Pharmacol. 44:8. The opioid receptors belong to a class of transmembrane spanning receptors known as G-protein coupled receptors. G-proteins consist of three tightly associated subunits, alpha, beta and gamma (1:1:1) in order of decreasing mass. Signal amplification results from the ability of a single receptor to activate many G-protein molecules, and from the stimulation by G-α-GTP of many catalytic cycles of the effector. Most opioid receptor-mediated functions appear to be mediated through G-protein interactions. Standifer and Pasternak (1997) Cell Signal. 9:237. Antisense oligodeoxynucleotides directed against various G-protein alpha subunits were shown to differentially block the analgesic actions of the mu-, delta-, and kappa-opioid agonists in mice. Standifer et al. (1996) Mol. Pharmacol. 50:293.

II. Compounds of the Present Disclosure

The compounds of the present disclosure are shown, for example, above, in the summary of the invention section, and in the claims below. They may be made using standard methods that can be further modified and optimized using the principles and techniques of organic chemistry as applied by a person skilled in the art. Such principles and techniques are taught, for example, in Smith, March's Advanced Organic Chemistry: Reactions, Mechanisms, and Structure, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, Practical Process Research & Development—A Guide for Organic Chemists (2012), which is incorporated by reference herein.

All the opiate compounds of the present disclosure may in some embodiments be used for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all the compounds of the present invention are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the opiate compounds of the present disclosure have the advantage that they may be more efficacious than, be less toxic than, be longer acting than, be more potent than, produce fewer side effects than, be more easily absorbed than, more metabolically stable than, more lipophilic than, more hydrophilic than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise. In particular, the compounds described herein may have a better pharmacological profile in that the show reduced activation of beta-arrestin.

Opiate compounds of the present disclosure may contain one or more asymmetrically-substituted carbon or nitrogen atom and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration. In some embodiments, the present opiate compounds may contain two or more atoms which have a defined stereochemical orientation.

Chemical formulas used to represent opiate compounds of the present disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the opiate compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

In some embodiments, opiate compounds of the present disclosure exist in salt or non-salt form. With regard to the salt form(s), in some embodiments the particular anion or cation forming a part of any salt form of a compound provided herein is not critical, so long as the salt, as a whole, is pharmacologically acceptable. Additional examples of pharmaceutically acceptable salts and their methods of preparation and use are presented in Handbook of Pharmaceutical Salts: Properties, and Use (2002), which is incorporated herein by reference.

III. Pharmaceutical Formulations and Routes of Administration

In another aspect, for administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of a opiate compounds disclosed herein formulated with one or more excipients and/or drug carriers appropriate to the indicated route of administration. In some embodiments, the opiate compounds disclosed herein are formulated in a manner amenable for the treatment of human and/or veterinary patients. In some embodiments, formulation comprises admixing or combining one or more of the compounds disclosed herein with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. In some embodiments, the pharmaceutical formulations may be subjected to pharmaceutical operations, such as sterilization, and/or may contain drug carriers and/or excipients such as preservatives, stabilizers, wetting agents, emulsifiers, encapsulating agents such as lipids, dendrimers, polymers, proteins such as albumin, nucleic acids, and buffers.

Pharmaceutical formulations may be administered by a variety of methods, e.g., orally or by injection (e.g. subcutaneous, intravenous, and intraperitoneal). Depending on the route of administration, the opiate compounds disclosed herein may be coated in a material to protect the compound from the action of acids and other natural conditions which may inactivate the compound. To administer the active compound by other than parenteral administration, it may be necessary to coat the compound with, or co-administer the compound with, a material to prevent its inactivation. In some embodiments, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The opiate compounds disclosed herein may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or poly alcohols such as mannitol and sorbitol, in the composition. Prolonged absorption of the injectable compositions can be brought about by including in the composition an agent which delays absorption, for example, aluminum monostearate or gelatin.

The opiate compounds disclosed herein can be administered orally, for example, with an inert diluent or an assimilable edible carrier. The compounds and other ingredients may also be enclosed in a hard or soft-shell gelatin capsule, compressed into tablets, or incorporated directly into the patient's diet. For oral therapeutic administration, the compounds disclosed herein may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such pharmaceutical formulations is such that a suitable dosage will be obtained.

The therapeutic compound may also be administered topically to the skin, eye, ear, or mucosal membranes. Administration of the therapeutic compound topically may include formulations of the compounds as a topical solution, lotion, cream, ointment, gel, foam, transdermal patch, or tincture. When the therapeutic compound is formulated for topical administration, the compound may be combined with one or more agents that increase the permeability of the compound through the tissue to which it is administered. In other embodiments, it is contemplated that the topical administration is administered to the eye. Such administration may be applied to the surface of the cornea, conjunctiva, or sclera. Without wishing to be bound by any theory, it is believed that administration to the surface of the eye allows the therapeutic compound to reach the posterior portion of the eye. Ophthalmic topical administration can be formulated as a solution, suspension, ointment, gel, or emulsion. Finally, topical administration may also include administration to the mucosa membranes such as the inside of the mouth. Such administration can be directly to a particular location within the mucosal membrane such as a tooth, a sore, or an ulcer. Alternatively, if local delivery to the lungs is desired the therapeutic compound may be administered by inhalation in a dry-powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical carrier. In some embodiments, the specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals. In some embodiments, the human equivalent dose (HED) in mg/kg can be calculated in accordance with the following formula (see, e.g., Reagan-Shaw et al., 2008, which is incorporated herein by reference):

HED (mg/kg)=Animal dose (mg/kg)×
(Animal $K_m$/Human $K_m$)

Use of the $K_m$ factors in conversion results in HED values based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are specific to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a opiate compounds disclosed herein or composition comprising a opiate compounds disclosed herein administered to a patient may be determined by physical and physiological factors such as type of animal treated, age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some embodiments, the amount is less than 10,000 mg per day with a range of 750 mg to 9,000 mg per day.

In some embodiments, the amount of the active compound in the pharmaceutical formulation is from about 2 to about 90 weight percent. In some of these embodiments, the amount if from about 25 to about 60 weight percent.

Single or multiple doses of the agents are contemplated. Desired time intervals for delivery of multiple doses can be determined by one of ordinary skill in the art employing no more than routine experimentation. As an example, patients may be administered two doses daily at approximately 12-hour intervals. In some embodiments, the agent is administered once a day.

The agent(s) may be administered on a routine schedule. As used herein a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the patient has eaten or will eat.

IV. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means=NH; "cyano" means —CN; "isocyanyl" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means=S; "thiocarbonyl" means —C(=S)—; "sulfonyl" means —S(O)$_2$—; and "sulfinyl" means —S(O)—.

In the context of chemical formulas, the symbol means a single bond, "=" means a double bond, and "≡" means triple bond. The symbol "- - - -" represents an optional bond, which if present is either single or double. The symbol "═══" represents a single bond or a double bond. Thus, the formula

covers, for example,

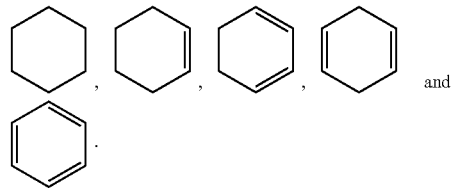

And it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol "⁓", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂▬" means a single bond where the group attached to the thick end of the wedge is "out of the page." The symbol "⦀⦀⦀" means a single bond where the group attached to the thick end of the wedge is "into the page". The symbol "⁓" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

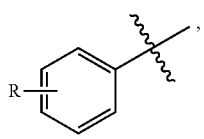

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

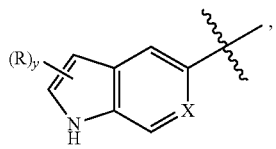

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" or "C=n" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "cycloalkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocycloalkyl$_{(C≤8)}$" is two, the minimum number of carbon atoms in the group "cycloalkyl$_{(C≤8)}$" is three, and the minimum number of carbon atoms in the groups "aryl$_{(C≤8)}$" and "arenediyl$_{(C≤8)}$" is six. "Cn-n'" defines both the minimum (n) and maximum number (n') of carbon atoms in the group. Thus, "alkyl$_{(C2≤10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefines" are all synonymous. Except as noted below, every carbon atom is counted to determine whether the group or compound falls with the specified number of carbon atoms. For example, the group dihexylamino is an example of a dialkylamino$_{(C=12)}$ group; however, it is not an example of a dialkylamino$_{(C=6)}$ group. Likewise, phenylethyl is an example of an aralkyl$_{(C=8)}$ group. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C=6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system. An aromatic compound or chemical group may be depicted as a single resonance structure; however, depiction of one resonance structure is taken to also refer to any other resonance structure. For example:

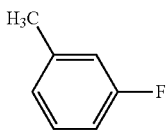

is also taken to refer to

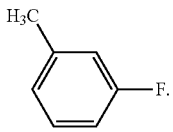

Aromatic compounds may also be depicted using a circle to represent the delocalized nature of the electrons in the fully conjugated cyclic π system, two non-limiting examples of which are shown below:

The term "alkyl" refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, Z-butyl, Z-Bu or $^t$Bu), and —CH$_2$C(CH$_3$)$_3$ (neo-pentyl) are non-limiting examples of alkyl groups. The term "alkanediyl" refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above.

The term "cycloalkyl" refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" refers to a divalent saturated aliphatic group with two carbon atoms as points of attachment, no carbon-carbon double or triple bonds, and no atoms other than carbon and hydrogen. The group

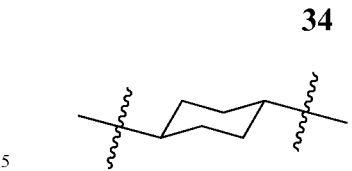

is a non-limiting example of cycloalkanediyl group. A "cycloalkane" refers to the class of compounds having the formula H—R, wherein R is cycloalkyl as this term is defined above.

The term "alkenyl" refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" refers to a divalent unsaturated aliphatic group, with two carbon atoms as points of attachment, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule.

The term "aryl" refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

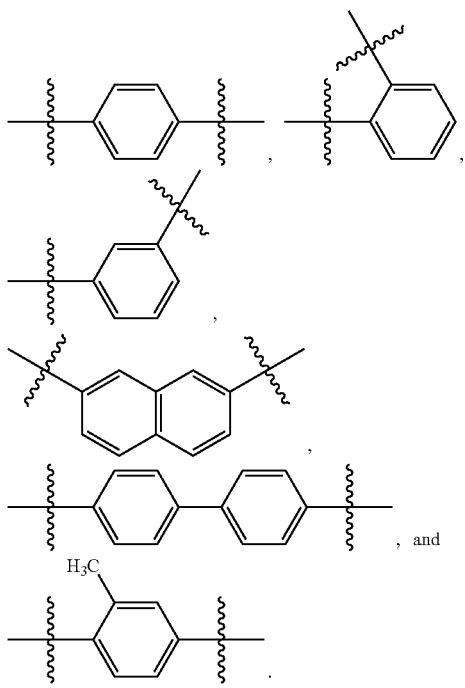
, and

An "arene" refers to the class of compounds having the formula H—R, wherein R is aryl as that term is defined above. Benzene and toluene are non-limiting examples of arenes.

The term "heteroaryl" refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include benzoxazolyl, benzimidazolyl, furanyl, imidazolyl (Im), indolyl, indazolyl (Im), isoxazolyl, methylpyridinyl, oxazolyl, oxadiazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "/V-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes.

The term "acyl" refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The "aldehyde" corresponds to an alkyl group, as defined above, attached to a —CHO group.

The term "alkoxy" refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), or —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group.

The term "alkylamino" refers to the group —NHR, in which R is an alkyl, as that term is defined above. Non-limiting examples include: —NHCH$_3$ and —NHCH$_2$CH$_3$. The term "dialkylamino" refers to the group —NRR', in which R and R' can be the same or different alkyl groups. Non-limiting examples of dialkylamino groups include: —N(CH$_3$)$_2$ and —N(CH$_3$)(CH$_2$CH$_3$). The term "amido" (acylamino), when used without the "substituted" modifier, refers to the group —NHR, in which R is acyl, as that term is defined above. A non-limiting example of an amido group is —NHC(O)CH$_3$.

When a chemical group is used with the "substituted" modifier, one or more hydrogen atom has been replaced, independently at each instance, by —OH, —F, —Cl, —Br, —I, —NH$_2$, —NO$_2$, —CO$_2$H, —CO$_2$CH$_3$, —CO$_2$CH$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. For example, the following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups. Non-limiting examples of substituted aralkyls are: (3-chlorophenyl)-methyl, and 2-chloro-2-phenyl-eth-1-yl. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON (CH$_3$)$_2$, are non-limiting examples of substituted acyl groups. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects or patients.

An "active ingredient" (AI) or active pharmaceutical ingredient (API) (also referred to as an active compound, active substance, active agent, pharmaceutical agent, agent, biologically active molecule, or a therapeutic compound) is the ingredient in a pharmaceutical drug that is biologically active.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to the patient or subject, is sufficient to effect such treatment or prevention of the disease as those terms are defined below.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, horse, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesullonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug, agent, or preparation) is a composition used to diagnose, cure, treat, or prevent disease, which comprises an active pharmaceutical ingredient (API) (defined above) and optionally contains one or more inactive ingredients, which are also referred to as excipients (defined above).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an active pharmaceutical ingredient of the present invention. The prodrug itself may or may not have activity with in its prodrug form. For example, a compound comprising a hydroxy group may be administered as an ester that is converted by hydrolysis in vivo to the hydroxy compound. Non-limiting examples of suitable esters that may be converted in vivo into hydroxy compounds include acetates, citrates, lactates, phosphates, tartrates, malonates, oxalates, salicylates, propionates, succinates, fumarates, maleates, methylene-bis-P-hydroxynaphthoate, gentisates, isethionates, di-p-toluoyltartrates, methanesulfonates, ethanesulfonates, benzenesulfonates, p-toluenesulfonates, cyclohexylsulfamates, quinates, and esters of amino acids. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

The term "unit dose" refers to a formulation of the compound or composition such that the formulation is prepared in a manner sufficient to provide a single therapeutically effective dose of the active ingredient to a patient in a single administration. Such unit dose formulations that may be used include but are not limited to a single tablet, capsule, or other oral formulations, or a single vial with a syringeable liquid or other injectable formulations.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

V. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Synthesis of New Opioid Derivatives

A. General

Reagents purchased from Sigma-Aldrich Chemicals, Fisher Scientific, Alfa Aesar; were used without further purification. While synthesizing the compounds, reaction mixtures were purified by silica gel flash chromatography on E. Merck 230-400 mesh silica gel 60 using a Teledyne ISCO CombiFlash $R_f$ instrument with UV detection at 280 and 254 nm. RediSep $R_f$ silica gel normal phase columns were used with a gradient range of 0-10% MeOH in DCM. Reported yields are isolated yields upon purification of each intermediate. Final clean (purity ≥95%, UPLC) compounds were used for the study. NMR spectra were collected using Bruker Avance III 500, or Avance III 600 with DCH CryoProbe instruments. Chemical shifts are reported in parts per million (ppm) relative to residual solvent peaks at the nearest 0.01 for proton and 0.1 for carbon (CDCl$_3$ $^1$H: 7.26, $^{13}$C: 77.1; and CD$_3$OD $^1$H: 3.31, $^{13}$C: 49.0). Peak multiplicity is reported as the NMR spectra were processed with MestreNova software, namely s—singlet, d—doublet, t—triplet, q—quartet, m—multiplet for examples. Coupling constant (J) values are expressed in Hz. High resolution mass spectra were obtained using a Waters Acuity Premiere XE TOE LC-MS by electrospray ionization and the accurate masses are reported for the molecular ion [M+H]+.

B. Synthesis

MP1202, MP1207 and MP1208. Synthesis of m-iodoarylamidomorphinans (MP1202) was achieved, by starting with known codeine phthalimide (Varadi et al., 2015) 1 in six sequential steps (Scheme 1A). The codeine phthalimides 1 was prepared from morphine in two steps according to the literature procedures. The reduction of codeine phthalimides in the presence of Pd/C and hydrogen followed by phthalimide group removal using excess of hydrazine hydrate gave the β-dihydrocodeine amine 2 (Crooks et al., 2006; Simon et al., 1994; Simon et al., 1992). The β-dihydrocodeine amine 2 was treated to m-iodobenzoic acid in the presence coupling reagent HATH with an organic base DIPEA to furnish corresponding m-iodoarylamidomorphinan 3. The m-iodoarylamidomorphinan 3 was treated with DIAD at 65° C. in acetonitrile for 20 hours followed by two equivalents of pyridine hydrochloride (Py.HCl) treatment at room temperature to obtain the m-iodoarylamidonormorphinan 4 (Yuan et al., 2013). A-alkylation of 4 was achieved by heating it with (bromomethyl)cyclopropane in the presence of $K_2CO_3$ in DMF to furnish 5. Finally, O-demethylation in 5 was performed using standard $BBr_3$ demethylation protocol obtain MP1202 (Varadi et al., 2015). On the other hand, MP1207-MP1208 were prepared (Scheme 1B) using β-dihydronaltrexamine 6 which was prepared form morphine in seven steps using known protocols (Simon et al., 1994; Simon et al., 1992). In addition, di-Boc-guanidinomethyl benzoic acid 8 was prepared by reacting amino methyl benzoic acid with N,N'-di-Boc-1H-pyrazole-1-carboxamidine at 50° C. (Robinson & Roskamp, 1997). Next, Boc-aminomethyl benzoic acid (Zhang et al., 2014) 7 and di-Boc-guanidinomethyl benzoic acid 8 were coupled with β-dihydronaltrexamine 6 in DMF in the presence of HATH and DIPEA to obtain corresponding analogs 9-10. Finally, deprotection of Boc group at 9-10 using TFA/DCM in the presence of triethyl silane as a cation scavenger furnished the desired compounds; m-aminomethyl and m-guanidinomethyl arylamidodihydromorphinans MP1207-MP1208.

Scheme 1. Synthesis of m-iodoarylamido dihydromorphinans MP1202, MP1207 and MP1208

A. MP1202 synthesis

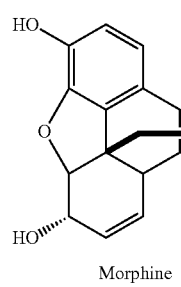

Morphine

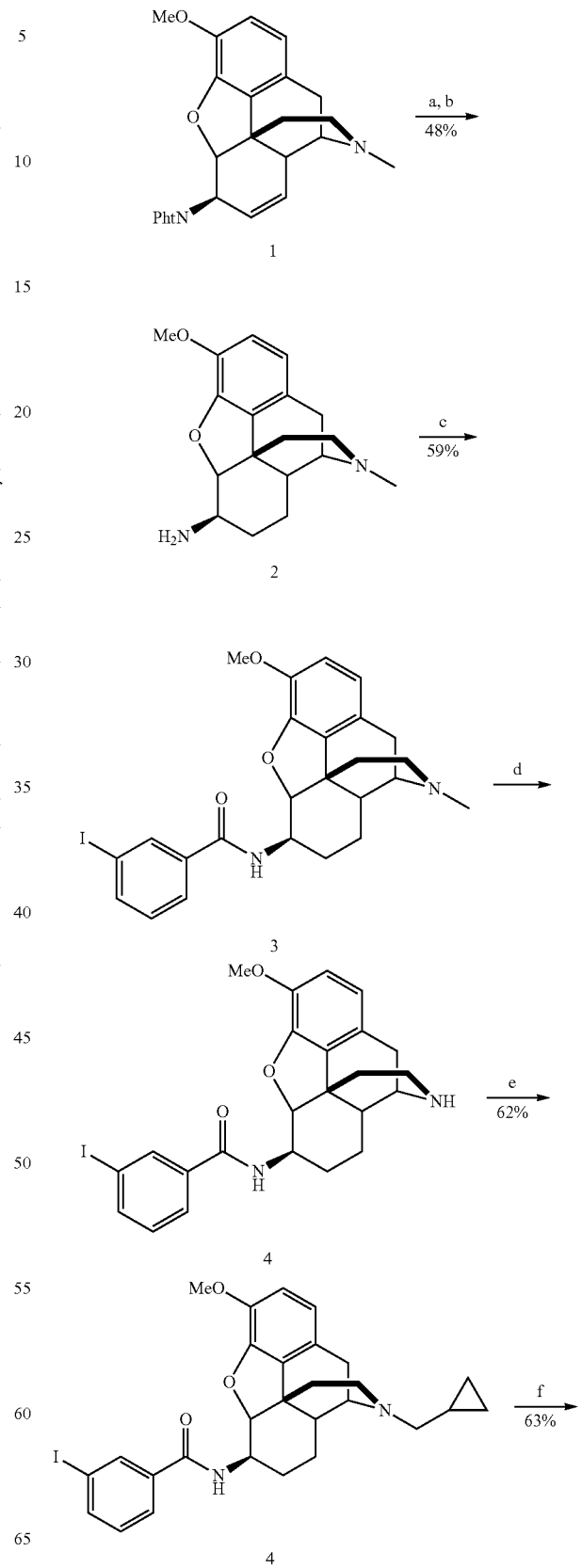

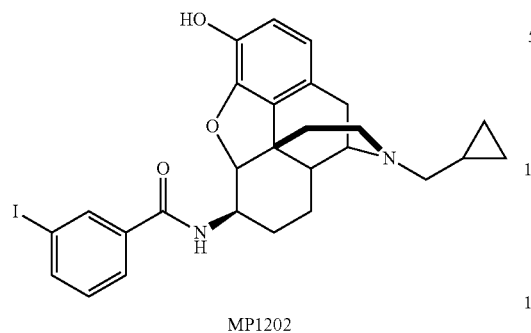

MP1202

B. MP1207 and MP1208 synthesis

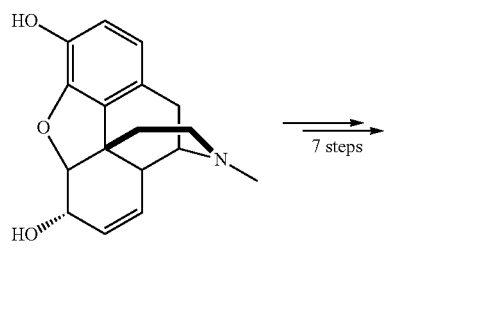

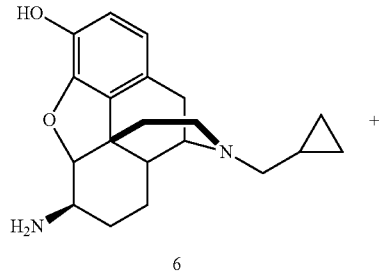

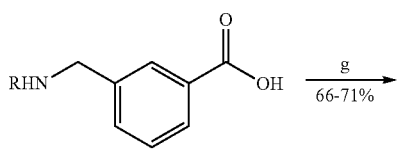

7, R = Boc
8, R = 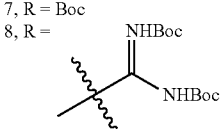

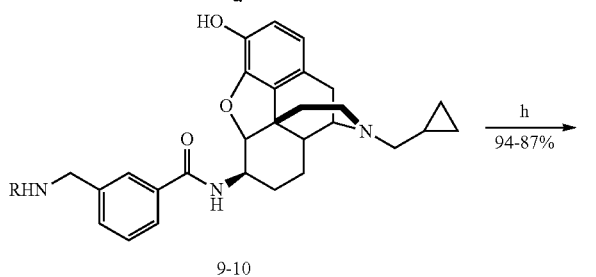

9-10

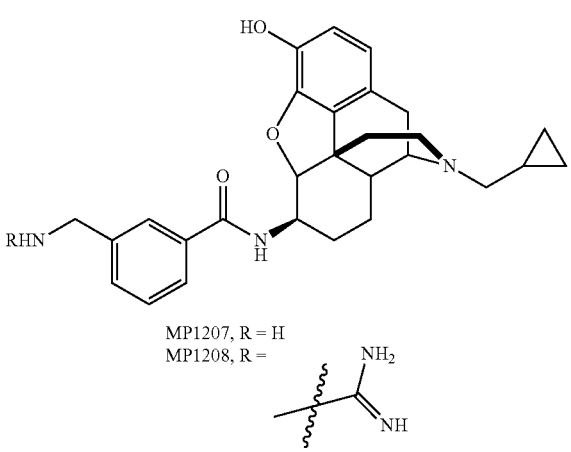

MP1207, R = H
MP1208, R = (NH₂, NH group)

Reagents/condition: a) Pd/C, H₂, 100 Psi 24 h, MeOH; b) NH₂—NH₂*H₂O, MeOH; c) m-IBA, HATU, DIPEA, DMF, 0° C.-rt; d) i. DIAD, AcN, 65° C., ii. Py•HCl/ACN; e) Na₂CO₃, R—X, DMF, 90° C.; f) BBr₃, DCM 0° C.-rt; g) HATU, DIPEA, DCM, 0° C.-rt; h) TES, TFA/DCM, rt.

MP1305. Synthesis of 14-O-methyl m-iodoarylamidomorphinan MP1305 was achieved by starting with the known ketal 11 in seven sequential steps (Scheme 2). At first, phenolic and ketone groups in naloxone were protected to obtain the ketal 11 prior the methylation of statically hindered 14-0 position (Nagase et al., 2006). The ketal 11 was treated with an excess of NaH at 0° C. in DMF and the mixture was heated with iodomethane at 55° C. Then, the ketal protecting group was removed by treating with an aqueous HCl in methanol at mild heat resulting in the known 14-O-methyl ketone 12 (Kobylecki et al., 1982). Stereoselective reduction of the ketone 12 using lithium selectride in THF at low temperature furnished corresponding a alcohol 13. The stereocenter inversion at C-6 position, with the introduction of a phthalimide moiety, was achieved using DIAD and PPh₃ by employing standard Mitsunobu protocol. Next, phthalimide moiety was removed by treating with excess of hydrazine hydrate in methanol to obtain β amine 14. Then, amine 14 was treated to m-iodobenzoic acid in the presence HATU and DIPEA in DMF followed by 3-O—demethylation of the intermediate using BBr₃ in DCM furnished 14-O-methyl m-iodoarylamidomorphinan MP1305.

Scheme 2. Synthesis of 14-O-methyl m-iodoarylamidomorphinan MP1305

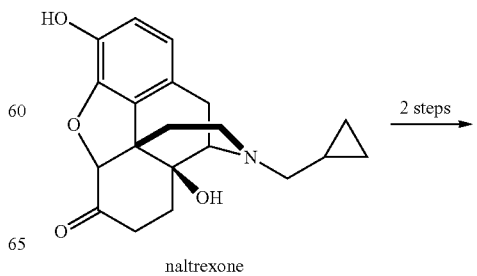

naltrexone

-continued

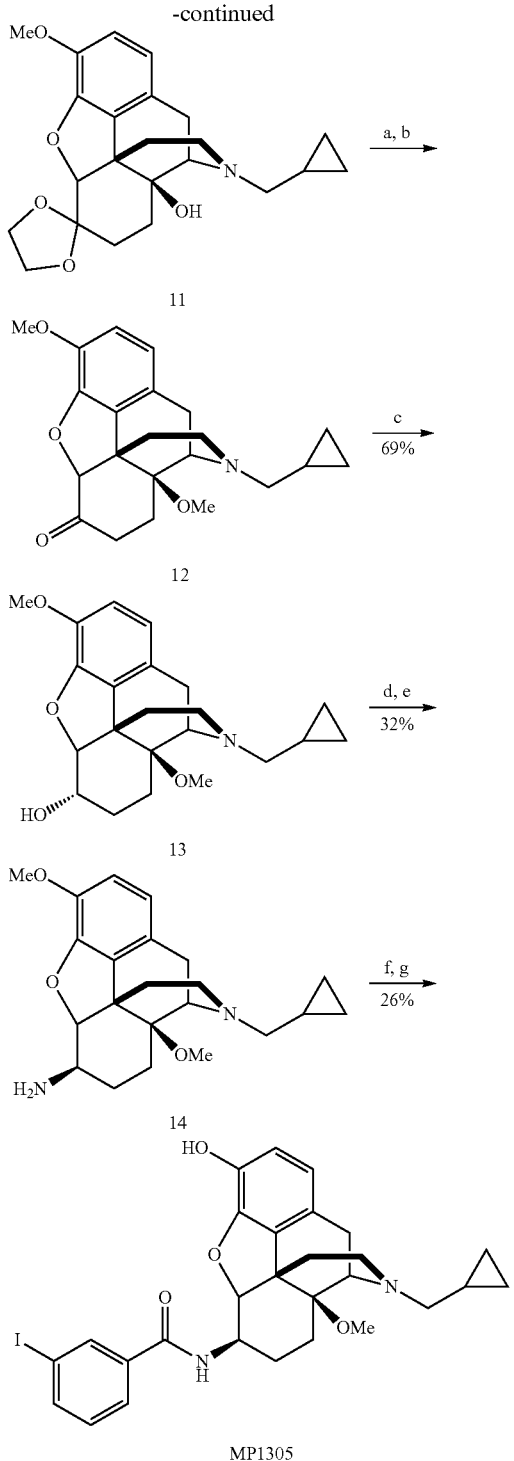

Reagents/condition: a) NaH, MeI, DMF, 55° C.; b) aq. HCl, MeOH; c) Li-selectride, THF, -78° C.-rt; d) PhtNH, PPh₃, DIAD, THF, 0° C.-rt; e) NH₂—NH₂*H₂O, MeOH; f) m-IBA, HATU, DIPEA, DMF, 0° C.-rt; g) BBr₃, DCM, 0° C.-rt.

MP1408. The β-naloxamine was synthesized from naloxone in three steps by following the previously published protocol (Majumdar et al., 2011). Next, synthesis of m-iodoarylmethylamidomorphinan MP1408 was achieved through the coupling of β-naloxamine (Scheme 3) with m-iodophenyl acetic acid in presence of HATU and DIPEA in DMF.

Scheme 3. Synthesis of m-iodoarylmethylamidomorphinan MP1408

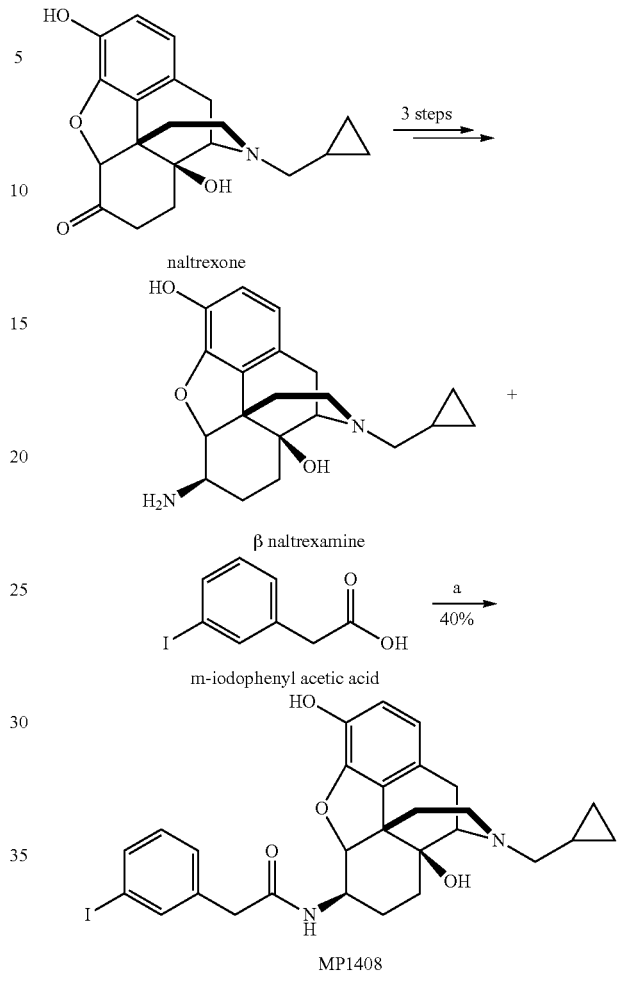

Reagents/condition: a) HATU, DIPEA, DMF, rt.

MP1601. Synthesis of m-iodoarylamido-4,5-deoxymorphinan MP1601 was achieved from the known ketone 15 (Scheme 4). The ketone 15 was synthesized in five steps using naltrexone by following literature reports (Tius and Kerr, 1992; Zhang et al., 2007; Hupp and Neumeyer, 2010). Reductive amination of the ketone 15 using NH₄OAc/NaCNBH₃ in methanol gave a racemic mixture of C-6 α/β amines (Majumdar et al., 2011). Separation of β amine from the α/β mixture while work up, was problematical then anticipated to isolate in optimum yield. However, upon using a mixture of 10% TEA and 1% MeOH in DCM as a column solvent with a silica gel column chromatography, β amine 16 was isolated in modest yield. The pattern spectral information in proton NMRs of the α and β amines are in agreement with that of close 4,5-epoxymorphinan α/β amines (Jiang et al., 1977). For instance, upon an introduction of amino moiety at C-6 position, the aromatic proton at C-4 position displays a significant downfield shift in comparison to that of ketone 15 ($\delta$=6.80 ppm $C_4$—$H_{Ar}$). The C-4 proton chemical shift ($\delta$) values in p and a amines are 7.01 and 6.86 ppm, which is about 0.21 and 0.06 ppm downfield shift respectively, indicating that p amino group poses lower effect (Jiang et al., 1977). Next, the β amine 16 was coupled with m-iodobenzoic acid using HATH as a coupling reagent in the presence of TEA to obtain 3-methoxy m-iodoary-lamido-4,5-deoxymorphinan 17. Finally, deprotection of 3-methyl group in 17 using BBr$_3$ in DCM furnished the desired m-iodoarylamido-4,5-deoxymorphinan MP1601.

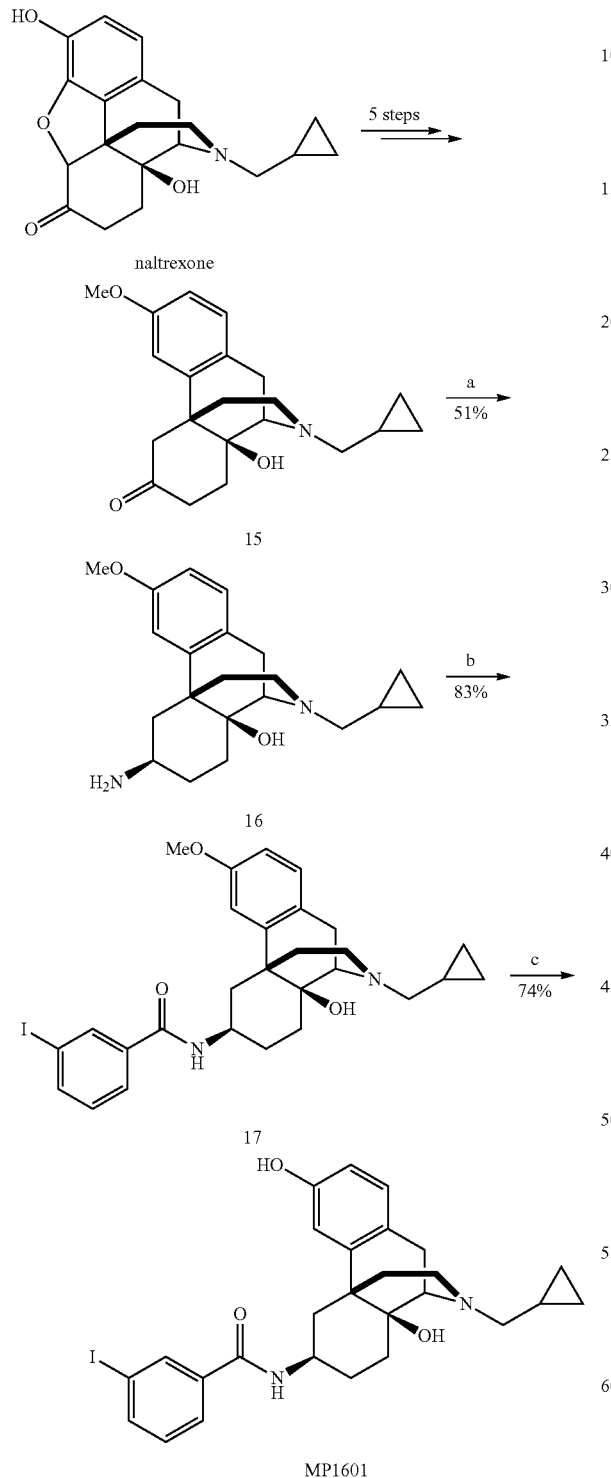

Scheme 4. Synthesis of m-iodoarylamido-4,5-deoxymorphinan MP1601

Reagents/condition: a) NH$_4$OAc, NaCNBH$_3$, MeOH, rt; b) m-IBA, HATU, DIPEA, DMF, rt; c) BBr$_3$, DCM, 0° C.-rt.

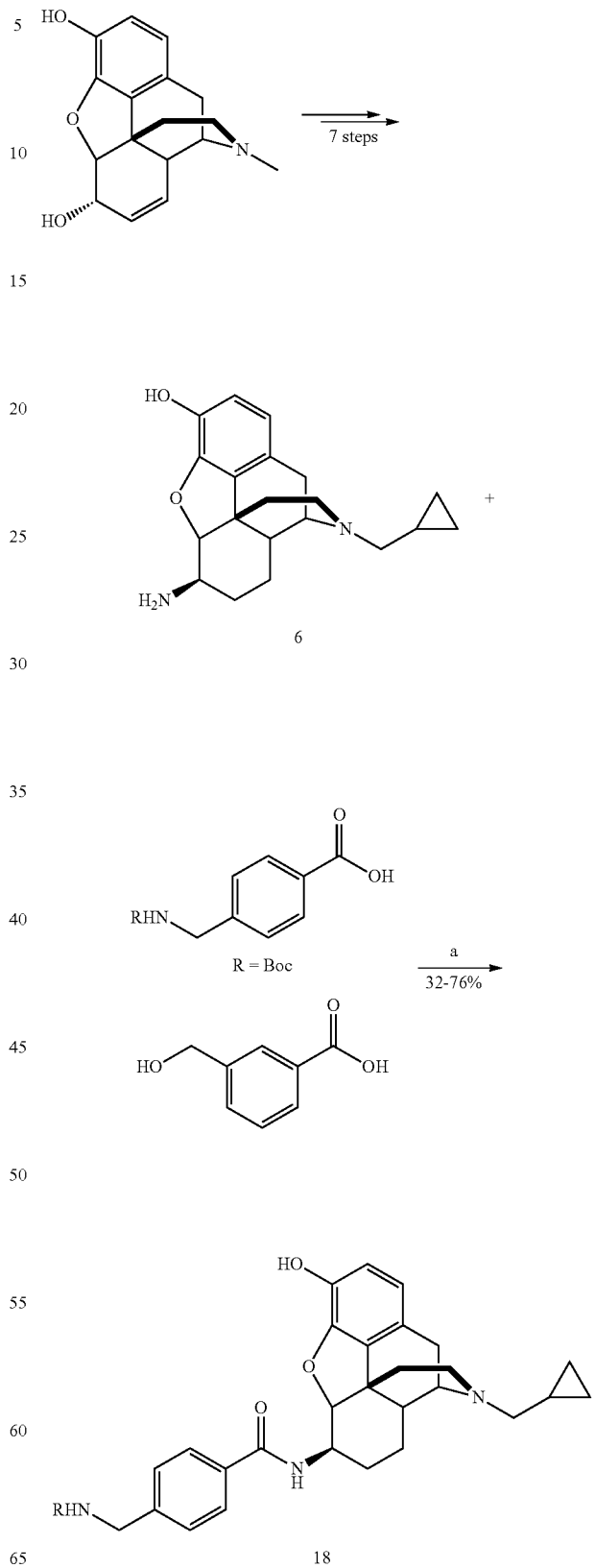

Scheme 4. Synthesis of m-hydroxymethyl and p-aminomethyl MP1209 and MP1210

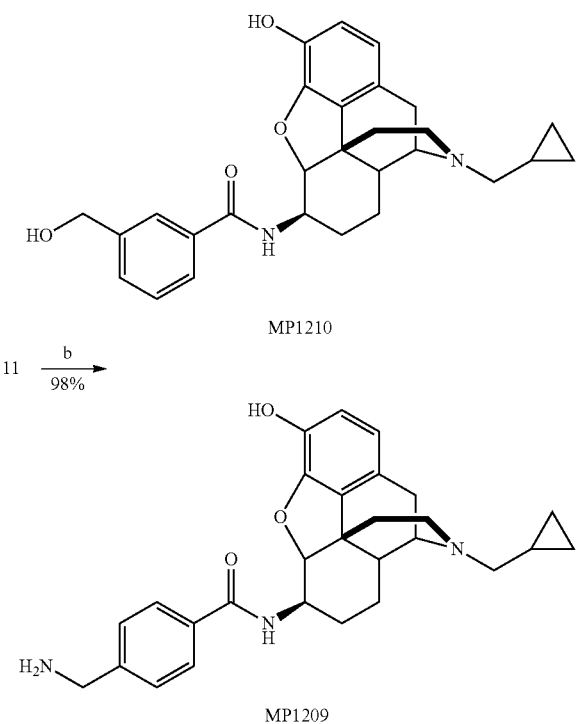

MP1210

11 $\xrightarrow[98\%]{b}$

MP1209

Reagents/condition: a) PyBOF, DIPEA, THF, rt; b) 4N HCL in dioxane, rt.

C. Preparation and Characterization of New Compounds (7R,12bS)-9-methoxy-3-methyl-2,3,4,4a,5,6,7,7a-octahydro-1H-4,12-methanobenzofuro[3,2-e]isoquinolin-7-amine (2). The known phthalimide 1 (3 g, 7.0 mmol) was dissolved in a stirred solution of DCM (15 mL) in methanol (100 mL). Palladium catalyst (10% Pd/C, 149 mg, 0.2 eq.) was added and the mixture was hydrogenated at 50 psi. After the completion of reaction monitored by mass spectrometry, the solution was filtered through Celite®, concentrated under reduced pressure, and the crude product was purified by silica gel column chromatography (ISCO, 40 g column) using methanol (5-15%) in DCM to get a white solid (2.7 g; Yield 90%) of the desired phthalimide dihydro intermediate whose spectral data matched with the literature reports. Then, hydrazine hydrate (21.5 mL, 34.5 mmol, 10 eq.) was added to the stirred solution of phthalimide dihydro intermediate (1.48 g, 3.4 mmol) in dry methanol (10 mL) at once at rt and the reaction was continued overnight. The reaction mixture was diluted with DCM (40 mL) and the organic layer washed with brine (2×20 mL), dried over anhydrous $Na_2SO_4$, filtered and concentrated under reduced pressure. The crude product was purified by silica gel column chromatography (ISCO, 12 g column) using a mixture of methanol in ethyl acetate with small amount of ammonium hydroxide as a base (87% EtOAC/10% MeOH/3% $NH_4OH$) to get a white solid. Finally, the white solid was redissolved in EtOAc, filtered, and precipitated by petroleum ether to get (0.96 g; Yield 93%) of the desired product 2. The spectral data of the compound 2 is matched with the literature reports (Varadi et al., 2015; Simon et al., 1992).

3-Iodo-N-((7R,12bS)-9-methoxy-3-methyl-2,3,4,4a,5,6,7,7a-octahydro-1H-4,12-methanobenzofuro[3,2-e]isoquinolin-7-yl)benzamide (3). m-Iodobenzoic acid (1.0 g, 4.03 mmol, 1.3 eq.) was added to a stirred solution of β-7,8-dihydro-codeine-$NH_2$ 2 (932 mg, 3.10 mmol) in DMF (10 mL) at. HATU (1.5 g, 4.03 mmol, 1.3 eq.) was added to the mixture at rt at once and after 5 minutes, DIPEA (1.62 mL, 9.31 mmol, 3 eq.) was added. After 20 minutes, the reaction mixture was diluted with EtOAc (80 mL). The EtOAc layer was washed with brine (5×50 mL) to remove DMF, dried over anhydrous $Na_2SO_4$, filtered, and concentrated under reduced pressure. The crude product was purified by silica gel column chromatography using a mixture of methanol (0-5%) in DCM to get desired products 3; (977 mg; Yield 59%). $^1$H NMR (600 MHz, $CDCl_3$) δ=8.10 (t, J=1.7 Hz, 1H), 7.85-7.77 (m, 1H), 7.72 (dt, J=7.9, 1.3 Hz, 1H), 7.13 (t, J=7.8 Hz, 1H), 6.73 (d, J=8.2 Hz, 1H), 6.66 (d, J=8.2 Hz, 1H), 4.56 (d, J=8.0 Hz, 1H), 3.82 (s, 3H), 3.75 (dq, J=12.6, 3.3 Hz, 1H), 3.15 (s, 1H), 3.02 (d, J=18.3 Hz, 1H), 2.57-2.51 (m, 1H), 2.43 (s, 3H), 2.27-2.14 (m, 2H), 2.05-1.98 (m, 1H), 1.87 (s, 1H), 1.70 (ddd, J=12.3, 3.8, 1.6 Hz, 1H), 1.62-1.49 (m, 1H), 1.38 (qd, J=13.0, 2.5 Hz, 1H), 1.11 (m, 1H). $^{13}$C NMR (151 MHz, $CDCl_3$) δ=165.8, 143.9, 143.7, 140.2, 136.6, 136.0, 130.1, 126.2, 119.3, 114.1, 94.1, 92.8, 77.2, 77.0, 76.8, 59.5, 56.7, 53.1, 47.2, 43.4, 42.7, 28.7, 24.1, 20.1; HRMS calcd for $C_{25}H_{27}IN_2O_3$ $[M+H]^+$, 531.1145; found, 531.1140.

3-Iodo-N-((7R,12bS)-9-methoxy-2,3,4,4a,5,6,7,7a-octahydro-1H-4,12-methanobenzofuro[3,2-e]isoquinolin-7-yl)benzamide (4). The dihydrocodeine iodoaryl amide (952 mg, 1.795 mmol) was added to a stirred solution of DIAD (636 μL, 3.21 mmol, 0.8 eq.) $CH_3CN$ (15 mL) at rt under an argon and the reaction mixture was heated to 65° C. for 20 h. The reaction mixture cooled to rt and pyridine HCl (415 mg, 3.59 mmol, 2 eq.) was added and the reaction was continued for 3 days. The solvent was removed under reduced pressure and the content was redissolved in DCM (30 mL). The DCM layer was washed with brine (2×20 mL), dried over anhydrous $Na_2SO_4$, filtered, and concentrated under reduced pressure. The crude product was purified by silica gel column chromatography using a mixture of methanol (2-15%) in DCM to get desired products 4; (607 mg; Yield, 66%). $^1$H NMR (600 MHz, $CDCl_3$) δ=9.80 (s, 2H), 8.14 (t, J=1.7 Hz, 1H), 7.80 (dt, J=7.9, 1.3 Hz, 1H), 7.75 (dt, J=7.8, 1.3 Hz, 1H), 7.15 (t, J=7.8 Hz, 1H), 6.81 (d, J=8.3 Hz, 1H), 6.75 (d, J=8.2 Hz, 2H), 4.73 (d, J=8.1 Hz, 1H), 4.00 (t, J=4.1 Hz, 1H), 3.84 (s, 3H), 3.79 (ddd, J=12.5, 8.2, 4.6 Hz, 1H), 3.32 (d, J=19.1 Hz, 1H), 3.21 (dd, J=13.5, 4.2 Hz, 1H), 3.06 (dd, J=19.2, 5.9 Hz, 1H), 2.83 (s, 1H), 2.62 (dt, J=12.4, 3.7 Hz, 1H), 2.18 (td, J=13.3, 4.6 Hz, 1H), 1.91-1.80 (m, 1H), 1.67 (dd, J=13.5, 4.1 Hz, 1H), 1.53-1.44 (m, 1H), 1.13-1.03 (m, 1H). $^{13}$C NMR (151 MHz, $CDCl_3$) δ=165.7, 149.8, 144.4, 144.0, 140.4, 136.2, 136.0, 136.0, 130.2, 127.5, 126.4, 123.7, 123.0, 120.4, 115.5, 94.2, 91.8, 56.9, 53.4, 52.6, 52.4, 42.7, 38.7, 37.9, 32.2, 28.0, 25.7, 23.3; ESI-MS m/z: 517.12 $[M+H]^+$.

N-((7R,12bS)-3-(Cyclopropylmethyl)-9-methoxy-2,3,4,4a,5,6,7,7a-octahydro-1H-4,12-methanobenzofuro[3,2-e]isoquinolin-7-yl)-3-iodobenzamide (5). $Na_2CO_3$ (92.4 mg, 0.87 mmol, 1.5 eq.) and (bromomethyl)cyclopropane (67.6 μL, 0.69 mmol, 1.2 eq.) were added to a stirred solution of dihydronorcodeine 4 (300 mg, 0.581 mmol) in DMF (1 mL) at rt under argon. The, the reaction mixture was heated to 90° C. overnight. Then the reaction mixture was cooled to rt and was diluted with EtOAc (20 mL). The EtOAc layer was washed with brine (5×20 mL) to remove DMF, dried over anhydrous $Na_2SO_4$, filtered, and concentrated under reduced pressure. The crude product was purified by silica gel column chromatography using a mixture of methanol (3-10%) in DCM to get desired products 5; (205 mg; Yield, 62%). $^1$H NMR (600 MHz, $CDCl_3$) δ=8.09 (t, J=1.8 Hz, 1H), 7.79 (dt, J=7.9, 1.3 Hz, 1H), 7.72 (dt, J=7.8, 1.3 Hz, 1H), 7.13 (t, J=7.8 Hz, 1H), 6.72 (d, J=8.2 Hz, 1H), 6.64 (d, J=8.2 Hz, 1H), 6.40 (s, 1H), 4.55 (d, J=8.0 Hz, 1H), 3.82 (s, 3H), 3.75 (ddd, J=12.4, 8.2, 4.8 Hz, 1H), 3.41 (s, 1H), 2.91 (d, J=18.3 Hz, 1H), 2.82-2.76 (m, 1H), 2.39 (dd, J=87.8, 49.2 Hz, 4H), 1.92 (d, J=16.2 Hz, 1H), 1.70 (ddd, J=12.3, 3.7, 1.7 Hz, 1H), 1.39 (td, J=12.9, 2.5 Hz, 1H), 1.12 (qd, J=12.9, 2.5 Hz, 1H), 0.87 (s, 1H), 0.53 (d, J=8.0 Hz, 2H), 0.15 (s, 2H). $^{13}$C NMR (151 MHz, CDCl$_3$) δ=171.2, 165.8, 143.8, 140.2, 136.6, 136.0, 130.1, 126.2, 119.2, 94.1, 92.9, 60.4, 59.8, 57.1, 56.6, 53.2, 45.7, 44.0, 28.7, 24.2, 21.1, 20.6, 14.2, 4.0, 3.8; HRMS calcd for C$_{28}$H$_3$IN$_2$O$_3$ [M+H]$^+$, 571.1458; found, 571.1474.

N-((7R,12bS)-3-(Cyclopropylmethyl)-9-hydroxy-2,3,4,4a,5,6,7,7a-octahydro-1H-4,12-methanobenzofuro[3,2-e]isoquinolin-7-yl)-3-iodobenzamide (MP1202). A solution of BBr$_3$ (7 mL, 7 eq.; 1M in DCM) was slowly added to a stirred solution of methoxy morphinan 4 (181 mg, 0.31 mmol) in DCM (7 mL) at 0° C. under argon. The reaction mixture was continued for 10 min at 0° C. and 20 more minutes at rt. The, the reaction mixture was quenched with excess of ammonia solution (5%) and the mixture was stirred for one hour. Then, the mixture was diluted with DCM (20 mL). The DCM layer was washed with brine (2×20 mL), dried over anhydrous Na$_2$SO$_4$, filtered, and concentrated under reduced pressure. The crude product was purified by silica gel column chromatography using a mixture of methanol (7-15%) in DCM to get desired products MP1202; (111 mg; Yield: 63%). $^1$H NMR (600 MHz, CDCl$_3$+CD$_3$OD) δ=8.10 (t, J=1.7 Hz, 1H), 7.74 (m, 2H), 7.11 (t, J=7.8 Hz, 1H), 6.62 (d, J=8.1 Hz, 1H), 6.49 (d, J=8.1 Hz, 1H), 4.38 (d, J=7.5 Hz, 1H), 3.80 (ddd, J=12.7, 7.5, 4.8 Hz, 1H), 3.55 (s, 3H), 3.43-3.23 (m, 2H), 2.82 (d, J=18.3 Hz, 1H), 2.68 (d, J=12.1 Hz, 1H), 2.41 (s, 1H), 2.32 (d, J=18.6 Hz, 2H), 2.08 (d, J=18.1 Hz, 2H), 1.81-1.76 (m, 2H), 1.61 (m, 1H), 1.56-1.50 (m, 1H), 1.35 (qd, J=13.0, 2.6 Hz, 1H), 1.09-0.97 (m, 1H), 0.79 (s, 1H), 0.49 (d, J=8.0 Hz, 2H), 0.10 (dd, J=14.1, 9.2 Hz, 2H). $^{13}$C NMR (151 MHz, CDCl$_3$+CD$_3$OD) δ=166.7, 142.8, 140.4, 136.2, 136.1, 130.1, 126.4, 119.4, 118.0, 93.9, 93.6, 59.5, 56.8, 52.2, 45.8, 43.7, 2.78, 24.1, 20.3, 3.93, 3.8; HRMS calcd for C$_{27}$H$_{29}$IN$_2$O$_3$ [M+H]$^+$, 557.1301; found, 557.1304.

(Z)-3-((2,3-bis(tert-Butoxycarbonyl)guanidino)methyl)benzoic acid (8). N,N'-di-Boc-1H-pyrazole-1-carboxamidine (54 mg, 0.17 mmol, 1.1 eq.) and triethyl amine (67 μL, 0.44 mmol, 3 eq.), were added to a stirred solution of 3-(aminomethyl) benzoic acid hydrochloride (30 mg, 0.16 mmol, 1 eq.) in MeOH (1 mL) at rt under argon. The reaction was heated to 50° C. and continued for 7 h. The solvent was removed under reduced pressure, and the content was diluted with EtOAc (15 mL). Water (15 mL) was added and the mixture was acidified with citric acid (to pH 3). The organic layer was separated and was washed with brine (15 mL), dried over anhydrous Na$_2$SO$_4$, filtered, and concentrated under reduced pressure. The crude product was purified by silica gel column chromatography using a mixture of EtOAc (20-50%) in hexanes to get the desired products 2 as a white solid; (46 mg; Yield; 78%). $^1$H NMR (600 MHz, Chloroform-7) δ=11.56 (s, 1H), 8.67 (t, J=5.4 Hz, 1H), 8.11-7.90 (m, 2H), 7.57 (dt, J=7.8, 1.4 Hz, 1H), 7.46 (t, J=7.7 Hz, 1H), 4.71 (d, J=5.3 Hz, 2H), 1.50 (d, J=17.8 Hz, 18H). $^{13}$C NMR (151 MHz, CDCl$_3$) δ=170.9, 163.5, 156.3, 153.2, 138.0, 133.1, 129.7, 129.6, 129.5, 129.0, 83.4, 79.6, 44.5, 28.3, 28.1.

tert-Butyl (3-(((7R,12bS)-3-(Cyclopropylmethyl)-9-hydroxy-2,3,4,4a,5,6,7,7a-octahydro-1H-4,12-methanobenzofuro[3,2-e]isoquinolin-7-yl)carbamoyl)benzyl)carbamate (9). The Boc aminomethylbenzoic acid 7 (28 mg, 0.11 mmol, 1.3 eq.) was added to a stirred solution of β-dihydromorphine amine 6 (28 mg, 0.08 mmol 1 eq.) in DMF (0.4 mL) at rt under argon. HATU (39 mg, 0.10 mmol, 1.2 eq.) was added to the mixture at rt at once and after 5 minutes, DIPEA (45 μL, 0.25 mmol, 3 eq.) was added. After 2 h, the reaction mixture was diluted with EtOAc (15 mL). The EtOAc layer was washed with brine (5×15 mL) to remove DMF, dried over anhydrous Na$_2$SO$_4$, filtered, and concentrated under reduced pressure. The residue was redissolved in MeOH (0.5 mL) and sodium methoxide in MeOH (0.2 mL, 0.5 M) was added to the mixture. After 15 min, the solvent was removed, redissolved in EtOAc (15 mL), washed with brine, dried over anhydrous Na$_2$SO$_4$, filtered, and the crude product was purified by silica gel column chromatography using a mixture of methanol (3-10%) in DCM to get 9 as a white solid, (31 mg, Yield; 66%); $^1$H NMR (600 MHz, Chloroform-7) δ=7.80 (s, 1H), 7.45 (d, J=44.7 Hz, 2H), 7.34 (d, J=7.6 Hz, 1H), 7.19 (t, J=7.7 Hz, 1H), 6.72 (d, J=8.0 Hz, 1H), 6.59 (d, J=8.1 Hz, 1H), 5.33 (s, 1H), 4.69 (s, 1H), 4.25 (dd, J=15.2, 5.9 Hz, 1H), 4.16 (dd, J=15.2, 6.1 Hz, 1H), 3.81 (s, 1H), 3.07 (s, 1H), 2.91 (d, J=18.3 Hz, 1H), 2.69 (s, 4H), 2.47-2.11 (m, 1H), 1.84 (d, J=12.6 Hz, 1H), 1.71 (s, 1H), 1.56 (d, J=32.4 Hz, 1H), 1.43 (s, 9H), 1.25 (s, 1H), 1.06 (q, J=12.7 Hz, 1H), 0.94-0.77 (m, 1H), 0.65 (s, 2H), 0.29 (hr, 1H). $^{13}$C NMR (151 MHz, CDCl$_3$) δ=167.3, 156.2, 143.0, 139.3, 134.3, 130.1, 128.6, 126.7, 125.7, 119.5, 92.4, 79.9, 59.1, 57.5, 52.0, 44.4, 43.1, 31.9, 29.7, 29.6, 29.3, 28.4, 24.0, 22.7, 21.0, 14.1, 4.4. ESI-MS m/z: 560.54 [M+H]$^+$.

2,3-BA(tert-Butoxycarbonyl) (—N-((7R,12bS')-3-(cyclopropylmethyl)-9-hydroxy-2,3,4,4a,5,6,7,7a-octahydro-1H-4,12-methanobenzofuro[3,2-e]isoquinolin-7-yl)-3-(guanidinomethyl)benzamide (5). The di-Boc-guanoomethylhenzoic acid 8 (32.9 mg, 0.08 mmol, 1.3 eq.) was added to a stirred solution of β-dihydromorphine amine 6 (21 mg, 0.06 mmol 1 eq.) in DMF (0.4 mL) at rt under argon. HATH (29 mg, 0.07 mmol, 1.2 eq.) was added to the mixture at rt at once and after 5 minutes, DIPEA (33 μL, 0.19 mmol, 3 eq.) was added. After 2 h, the reaction mixture was diluted with EtOAc (15 mL). The EtOAc layer was washed with brine (5×15 mL) to remove DMF, dried over anhydrous Na$_2$SO$_4$, filtered, and concentrated under reduced pressure. The residue was redissolved in MeOH (0.5 mL) and sodium methoxide in MeOH (0.2 mL, 0.5 M) was added to the mixture. After 15 min, the solvent was removed, redissolved in EtOAc (15 mL), washed with brine, dried over anhydrous Na$_2$SO$_4$, filtered, and the crude product was purified by silica gel column chromatography using a mixture of methanol (3-10%) in DCM to get 10 as a white solid, (32 mg, Yield; 71%); $^1$H NMR (600 MHz, Chloroform-7) δ=11.52 (s, 1H), 8.82 (d, J=6.9 Hz, 1H), 7.78 (s, 1H), 7.43 (d, J=7.5 Hz, 1H), 7.29 (d, J=7.6 Hz, 1H), 7.19 (t, J=7.7 Hz, 1H), 7.07 (d, J=14.4 Hz, 1H), 6.82 (d, J=8.1 Hz, 1H), 6.63 (d, J=8.2 Hz, 1H), 4.87 (s, 1H), 4.57 (dd, J=15.4, 6.7 Hz, 1H), 4.44-4.34 (m, 1H), 3.85 (s, 2H), 3.24 (s, 1H), 2.97 (d, J=18.1 Hz, 1H), 2.74 (s, 3H), 2.48 (s, 1H), 2.37-2.16 (m, 1H), 2.03-1.91 (m, 1H), 1.83 (s, 1H), 1.62 (dd, J=30.8, 8.7 Hz, 1H), 1.49 (d, J=6.2 Hz, 18H), 1.37 (dd, J=13.6, 8.9 Hz, 1H), 1.32-1.21 (m, 1H), 1.13 (q, J=12.7 Hz, 1H), 0.93-0.78 (m, 1H), 0.68 (s, 2H), 0.37 (d, J=54.7 Hz, 2H). $^{13}$C NMR (151 MHz, CDCl$_3$) δ=167.0, 163.1, 156.3, 153.2, 143.1, 141.4, 137.9, 133.7, 129.8, 128.6, 126.5, 126.2, 120.0, 118.4, 92.4, 83.5, 80.0, 59.2, 57.9, 52.2, 46.7, 44.0, 43.0, 32.0, 29.7, 29.7, 29.6, 29.5, 29.4, 28.5, 28.3, 28.2, 28.1, 28.0, 23.8, 22.7, 21.1, 14.2, 14.2, 4.5. ESI-MS m/z: 702.55 [M+H]$^+$.

3-(Aminomethyl)-N-((7R,726S)-3-(cyclopropylmethyl)-9-hydroxy-2,3,4,4a,5,6,7,7a-octahydro-1H-4,12-methanobenzofuro[3,2-e]isoquinolin-7-yl)benzamide (MP1207).

Triethylsilane (21 µL, 0.19 mmol, 2.5 eq.) was added to the solution of 9 (30 mg, 0.05 mmol 1 eq.) in TFA/DCM (1:1, 1 mL) at rt. The reaction was continued for 30 minutes. Mass spectrometry indicated the reaction was completed. The volatilities were removed under reduced pressure. The content was redissolved in DCM (0.4 mL) and treated with Et$_2$O (3 mL) while shaking resulting in a white precipitation. The precipitate was washed with Et$_2$O (3 mL) and dried under high vacuum to get the desired amino product MP1207 as a white solid (33 mg, Yield 94%); $^1$H NMR (600 MHz, deuterium oxide) δ=7.79 (dd, J=7.0, 1.4 Hz, 2H), 7.64 (dt, J=7.9, 1.4 Hz, 1H), 7.61-7.53 (m, 1H), 6.95-6.85 (m, 1H), 6.85-6.75 (m, 1H), 4.74 (dd, J=11.0, 8.1 Hz, 1H), 4.23 (s, 3H), 3.77 (ddt, J=12.2, 8.3, 4.1 Hz, 1H), 3.42 (td, J=11.6, 9.7, 5.4 Hz, 1H), 3.36-3.26 (m, 1H), 3.20 (d, J=19.7 Hz, 1H), 3.10-2.95 (m, 2H), 2.76 (td, J=13.2, 4.0 Hz, 1H), 2.48 (ddd, J=12.5, 4.6, 2.8 Hz, 1H), 2.14 (td, J=13.5, 4.7 Hz, 1H), 1.92 (ddd, J=13.8, 4.2, 1.7 Hz, 1H), 1.87-1.72 (m, 2H), 1.54 (qd, J=13.1, 2.5 Hz, 1H), 1.19-0.99 (m, 2H), 0.83-0.61 (m, 2H), 0.46-0.28 (m, 2H). $^{13}$C NMR (151 MHz, D$_2$O, without TFA peaks) δ=170.0, 142.1, 139.8, 134.5, 133.1, 132.2, 129.5, 128.0, 127.6, 122.9, 120.5, 92.1, 58.8, 58.6, 51.6, 46.5, 42.6, 42.4, 42.1, 39.7, 32.4, 27.4, 23.1, 20.4, 5.2, 3.6, 3.4, HRMS calcd for C$_{28}$H$_{34}$N$_3$O$_3$ [M+H]$^+$, 460.2600; found, 460.2585.

N-((7R,12bS)-3-(Cyclopropylmethyl)-9-hydroxy-2,3,4,4a,5,6,7,7a-octahydro-1H-4,12-methanobenzofuro[3,2-e]isoquinolin-7-yl)-3-(guanidinomethyl)benzamide (MP1208). Triethylsilane (35.6 µL, 0.22 mmol, 5 eq.) was added to the solution of 10 (31 mg, 0.04 mmol 1 eq.) in TFA/DCM (1:1, 1 mL) at rt. The reaction was continued for 30 minutes. Mass spectrometry indicated the reaction was completed. The volatilities were removed under reduced pressure. The content was redissolved in DCM (0.4 mL) and treated with Et$_2$O (3 mL) while shaking resulting in a white precipitation. The precipitate was washed with Et$_2$O (3 mL) and dried under high vacuum to get the desired amino product MP1208 as a white solid (28 mg, Yield 87%); $^1$H NMR (600 MHz, deuterium oxide) δ=7.64-7.51 (m, 2H), 7.48-7.28 (m, 2H), 6.86-6.49 (m, 2H), 4.68-4.57 (m, 1H), 4.37 (d, J=5.7 Hz, 2H), 4.12 (dd, J=5.7, 2.8 Hz, 1H), 3.66 (ddd, J=12.7, 8.2, 4.3 Hz, 1H), 3.31 (td, J=16.6, 15.0, 5.9 Hz, 1H), 3.22-3.15 (m, 1H), 3.10 (dd, J=19.8, 3.2 Hz, 1H), 3.00-2.85 (m, 2H), 2.65 (td, J=13.2, 4.2 Hz, 1H), 2.38 (ddd, J=12.3, 4.4, 2.7 Hz, 1H), 2.04 (td, J=13.5, 4.6 Hz, 1H), 2.00-1.92 (m, OH), 1.87-1.76 (m, 1H), 1.76-1.62 (m, 1H), 1.43 (tdd, J=13.9, 10.4, 5.3 Hz, 1H), 0.98 (tdd, J=13.7, 8.9, 4.8 Hz, 2H), 0.71-0.58 (m, 2H), 0.34-0.19 (m, 2H). $^{13}$C NMR (151 MHz, D$_2$O, without TFA peaks) δ=170.3, 156.8, 142.2, 139.7, 136.7, 134.2, 130.3, 129.2, 128.0, 126.3, 125.5, 122.9, 120.5, 118.1, 92.1, 58.8, 58.6, 51.6, 46.5, 44.1, 42.1, 39.7, 32.4, 27.4, 23.1, 20.4, 5.2, 3.6, 3.4. HRMS calcd for C$_{29}$H$_{36}$N$_5$O$_3$ [M+H]$^+$, 502.2818; found, 502.2816.

4-(aminomethyl)-N-((4R,4aR,7R,7aR,12bS)-3-(cyclopropylmethyl)-9-hydroxy-2,3,4,4a,5,6,7,7a-octahydro-1H-4,12-methano[1]benzofuro[3,2-e]isoquinolin-7-yl)benzamide (MP1209) To a suspension of PyBOP (70 mg, 0.135 mmol, 2.2 equiv) in THF (100 mL) were sequentially added a solution of 4-(((tert-butoxy carbonyl)amino)methyl)benzoic acid (34 mg, 0.135 mmol, 2.2 equiv) in THF (100 mL) and NEt(iPr)$_2$ (24 mL, 0.135 mmol, 2.2 equiv) and the resulting mixture was stirred for 40 min. at r. t. This solution was subsequently added via cannula to a suspension of solution of β-dihydro N—CPM morphineamine 6 (20 mg, 0.061 mmol, 1.0 equiv) in THF (100 mL) and the mixture was stirred at r. t. overnight. To the crude mixture methanol and potassium carbonate were added and stirring was continued for 2 hours. After filtration the solvent was removed on a rotary evaporator, and the crude product was loaded on a 4 g Silica Gold column. Chromatography was performed with 5% to 10% MeOH (containing 10% concentrated NH$_4$OH solution) gradient in 6 minutes. The desired Boc protected intermediate eluted around 5-6 minutes. Deprotection of the Boc protected amine (18) was achieved in 3 h using 4N HCl in dioxane. The product was obtained as a white powder after removal of the solvent and trituration with diethyl ether (25 mg, 76%). $^1$H NMR (400 MHz, CDCl$_3$) δ: 7.92 (dd, J=8.3, 2.1 Hz, 2H), 7.60-7.53 (m, 2H), 6.79-6.67 (m, 2H), 4.78 (dd, J=8.0, 1.9 Hz, 1H), 4.18 (s, 3H), 3.88-3.71 (m, 1H), 3.64 (d, J=1.9 Hz, 2H), 3.51-3.39 (m, 1H), 3.38-3.28 (m, 1H), 3.20 (d, J=19.0 Hz, 1H), 3.06-2.92 (m, 2H), 2.73 (td, J=13.0, 4.0 Hz, 1H), 2.63 (d, J=12.2 Hz, 1H), 2.26 (td, J=13.5, 4.7 Hz, 1H), 1.95-1.71 (m, 3H), 1.69-1.49 (m, 1H), 1.24-1.06 (m, 3H), 0.78 (dd, J=10.7, 7.5 Hz, 2H), 0.58-0.43 (m, 2H). $^{13}$C NMR (101 MHz, CDCl$_3$) δ: 164.45, 139.51, 138.14, 133.32, 131.56, 125.44, 124.54, 124.52, 124.29, 117.92, 116.55, 114.77, 87.95, 63.45, 55.79, 55.34, 48.72, 39.16, 39.09, 36.66, 29.62, 24.71, 20.07, 17.26, 2.17. HRMS calcd for C$_{28}$H$_{33}$N$_3$O$_3$ [M+H]$^+$, 460.2594; found, 460.2599.

N-((4R,4aR,7R,7aR,12bS)-3-(cyclopropylmethyl)-9-hydroxy-2,3,4,4a,5,6,7,7a-octahydro-1H-4,12-methano[1]benzofuro[3,2-e]isoquinolin-7-yl)-3-(hydroxymethyl)benzamide (MP1210). To a suspension of PyBOP (70 mg, 0.135 mmol, 2.2 equiv) in THF (100 mL) were sequentially added a solution of 3-(hydroxymethyl)benzoic acid (21 mg, 0.135 mmol, 2.2 equiv) in THF (100 mL) and NEt(iPr)$_2$ (24 mL, 0.135 mmol, 2.2 equiv) and the resulting mixture was stirred for 40 min. at r. t. This solution was subsequently added via cannula to a suspension of solution of β-dihydro N—CPM morphineamine 6 (20 mg, 0.061 mmol, 1.0 equiv) in THF (100 mL) and the mixture was stirred at r. t. overnight. To the crude mixture methanol and potassium carbonate were added and stirring was continued for 2 hours. After filtration the solvent was removed on a rotary evaporator, and the crude product was loaded on a 4 g Silica Gold column. Chromatography was performed with 5% to 20% MeOH (containing 10% concentrated NH$_4$OH solution) gradient in 12 minutes. The desired product eluted around 11-12 minutes (15 mg, Yield 51%). $^1$H NMR (400 MHz, CDCl$_3$) δ: 8.27 (s, 1H), 8.20 (d, J=7.7 Hz, 1H), 7.97 (d, J=7.7 Hz, 1H), 7.89 (dt, J=10.6, 5.1 Hz, 1H), 7.19 (d, J=8.3 Hz, 1H), 7.09 (d, J=8.1 Hz, 1H), 5.14 (s, 2H), 5.09-5.03 (m, 1H), 4.87 (s, 5H), 4.40-4.29 (m, 1H), 4.26 (s, 1H), 3.82 (d, J=14.1 Hz, 1H), 3.55 (d, J=11.7 Hz, 1H), 3.44 (s, 1H), 3.32 (s, 1H), 3.20 (s, 1H), 3.16 (s, 1H), 3.03 (s, 1H), 2.91 (s, 1H), 2.68-2.63 (m, OH), 2.62 (s, 1H), 2.34 (d, J=13.3 Hz, 1H), 2.25 (d, J=13.1 Hz, 1H), 2.13 (d, J=13.1 Hz, 1H), 1.97 (q, J=13.1 Hz, 1H), 1.63-1.52 (m, 2H), 1.15 (d, J=8.1 Hz, 2H), 0.83 (d, J=13.5 Hz, 2H). $^{13}$C NMR (101 MHz, CDCl$_3$) δ: 169.20, 143.41, 142.19, 141.22, 134.71, 130.51, 128.80, 126.51, 125.92, 120.05, 118.79, 93.14, 64.24, 59.50, 58.21, 52.41, 46.80, 43.52, 40.79, 33.97, 28.81, 24.26, 21.39, 7.49, 4.65, 4.46. HRMS calcd for C$_{28}$H$_{32}$N$_2$O$_4$ [M+H]$^+$, 461.2435; found, 460.2440.

(4aS,7S,12bS)-3-(Cyclopropylmethyl)-4a,9-dimethoxy-2,3,4,4a,5,6,7,7a-octahydro-1H-4,12-methanobenzofuro[3,2-e]isoquinolin-7-ol (13). A solution of Li-selectride (1.3 mL, 1.3 mmol, 2 eq. 1M in THF) was slowly added to the stirred solution of known ketone (Kobylecki et al., 1982) 12 (320 mg, 0.86 mmol) in THF (5 mL) at −78° C. The reaction mixture was continued at the temperature for 90 minutes. The reaction mixture was quenched with cold methanol (0.2 mL) at −78° C. and the cold bath was removed and is continued stirring for 10 minutes to warm up to rt. Then, the product was extracted four times (4×20 mL) using DCM. The organic layer was dried over anhydrous sodium sulfate, filtered, and concentrated under reduced pressure. The crude product was purified by silica column (ISCO flash column) using methanol (1-2%) in DCM. The product fraction was concentrated and dried under high vacuum to get desired products 13; (240 mg, Yield 75%); $^1$H NMR (600 MHz, Chloroform-7) δ=6.71 (d, J=8.2 Hz, 1H), 6.58 (d, J=8.2 Hz, 1H), 4.66 (dd, J=4.8, 1.1 Hz, 1H), 4.22 (dt, J=9.4, 4.6 Hz, 1H), 3.87 (s, 3H), 3.53 (d, J=6.0 Hz, 1H), 3.29 (s, 3H), 3.12 (d, J=18.3 Hz, 1H), 2.65 (dd, J=12.0, 5.2 Hz, 1H), 2.53-2.40 (m, 2H), 2.38 (dd, J=18.4, 6.1 Hz, 1H), 2.28-2.10 (m, 2H), 1.88-1.73 (m, 1H), 1.66 (ddt, J=14.7, 8.4, 4.0 Hz, 1H), 1.42 (ddd, J=12.3, 3.8, 1.6 Hz, 1H), 1.16-1.02 (m, 2H), 0.93-0.84 (m, 1H), 0.62-0.43 (m, 2H), 0.16--0.06 (m, 2H). ESI-MS m/z: 372.4 [M+H]$^+$ (4aS,7R,12bS)-3-(Cyclopropylmethyl)-4a,9-dimethoxy-2,3,4,4a,5,6,7,7a-octahydro-1H-4,12-methanobenzofuro[3,2-e]isoquinolin-7-amine (14). Phthalimide (36.4 mg, 0.24 mmol, 2 eq.) and triphenylphosphine (48.7 mg, 0.18 mmol, 1.5 eq.) were added to a stirred solution of alcohol 13 (46 mg, 0.12 mmol) in THF (1 mL.) under argon. Diisopropyl azodicarboxylate (36.8 µL, 0.18 mmol, 1.5 eq.) was added drop wise to the reaction mixture at 0° C. and the reaction was continued for overnight. The reaction mixture was quenched with water (0.5 mL) and the mixture was stirred for 10 minutes at rt. The organic solvent was removed under reduced pressure. The residue was treated with 2% aqueous citric acid (1 mL), and dilute HCl (0.1 M, 1 mL) solutions. The mixture was washed with Et$_2$O (3×2 mL). Then, the aqueous layer was basified (pH=10) using an ammonia solution. The product was extracted in CHCl$_3$ (3×5 mL), dried over anhydrous Na$_2$SO$_4$, filtered, and concentrated under reduced pressure. The crude product was purified by silica gel column chromatography using methanol (1-5%) in DCM to obtain white solid of phthalimides intermediates (19 mg, 32%) upon drying. Then, hydrazine hydrate (23.8 µL, 10 eq.) was added to the stirred solution of the phthalimide intermediate in methanol (2 mL) at once heated to 50° C. for 90 minutes to complete the reaction. The reaction mixture was diluted with DCM (4 mL) and the product was extracted in dilute HCl (3×2 mL), the aqueous layer was basified with dilute NH$_4$OH (5%) and the amine is extracted in DCM (3×2 mL). The DCM layer was dried over anhydrous Na$_2$SO$_4$, filtered and concentrated under reduced pressure to get the desired product 14; (14 mg, yield; quantitative, which was used without further purification); $^1$H NMR (600 MHz, Chloroform-7) 5 6.69 (d, J=8.2 Hz, 1H), 6.59 (d, J=8.1 Hz, 1H), 4.30 (d, J=6.9 Hz, 1H), 3.86 (s, 3H), 3.55 (d, J=5.1 Hz, 1H), 3.25 (s, 3H), 3.11 (d, J=18.2 Hz, 1H), 2.69-2.52 (m, 2H), 2.52-2.26 (m, 4H), 2.05 (td, J=12.1, 3.9 Hz, 1H), 1.82 (dt, J=14.3, 3.3 Hz, 1H), 1.63 (qd, J=12.8, 2.7 Hz, 1H), 1.52-1.39 (m, 1H), 1.36-1.20 (m, 2H), 1.20-1.05 (m, 1H), 0.87 (tt, J=8.9, 7.1, 3.3 Hz, 1H), 0.64-0.43 (m, 2H), 0.24-0.09 (m, 2H). ESI-MS m/z: 371.37 [M+H]$^+$.

N-((4aS,7R,12bS)-3-(Cyclopropylmethyl)-9-hydroxy-4a-methoxy-2,3,4,4a,5,6,7,7a-octahydro-1H-4,12-methanobenzofuro[3,2-e]isoquinolin-7-yl)-3-iodobenzamide (MP1305). m-Iodobenzoic acid (8.86 mg, 0.035 mmol, 1.3 eq.) was added to a stirred solution of β-amine 14 (12 mg, 0.032 mmol) in DMF (0.2 mL) at. HATU (14.7 mg, 0.038 mmol, 1.3 eq.) was added to the mixture at rt at once and after 5 minutes, DIPEA (16.9 µL, 3 eq.) was added and the reaction was continued for 1h. Then, the reaction mixture was diluted with EtOAc (5 mL) and the EtOAc layer was washed with brine (5×3 mL) to remove DMF. The organic layer was dried over anhydrous Na$_2$SO$_4$, filtered, and concentrated under reduced pressure. The crude product was purified by silica gel column chromatography using a mixture of methanol (1-2%) in DCM to obtain white solid of methoxy intermediates (10 mg, 52%) upon drying. Then, BBr$_3$ solution (116 µL, 0.116 mmol, 7 eq, 1M in DCM) was added to a stirred solution of methoxy intermediate (10 mg, 0.016 mmol) in DCM (2 mL) at 0° C. under argon. The reaction mixture was continued for 10 min at 0° C. and 20 more minutes at rt. The, reaction mixture was diluted with DCM (8 mL) and quenched with excess of NH$_4$OH (5%, 2 mL) and the mixture was stirred for 1 h. The DCM layer was washed with brine (2×2 mL), dried over anhydrous Na$_2$SO$_4$, filtered, and concentrated under reduced pressure. The crude product was purified by silica gel column chromatography using a mixture of methanol (5-10%) in DCM to get desired products MP1305; (4.9 mg, Yield 26%); $^1$H NMR (600 MHz, methanol-d$_4$) δ=8.21 (t, J=1.7 Hz, 1H), 8.02-7.75 (m, 1H), 7.25 (t, J=7.8 Hz, 1H), 6.69 (q, J=8.2 Hz, 2H), 4.71 (d, J=7.7 Hz, 1H), 4.09 (s, 1H), 3.87 (ddd, J=12.7, 7.7, 5.2 Hz, 1H), 2.82 (s, 3H), 2.73-2.35 (m, 4H), 2.06 (d, J=14.6 Hz, 1H), 1.87-1.61 (m, 2H), 1.56-1.27 (m, 3H), 1.02 (s, 1H), 0.68 (d, J=55.0 Hz, 3H), 0.37 (s, 3H). $^{13}$C NMR (151 MHz, MeOD) δ=168.30, 143.52, 141.68, 137.67, 137.48, 131.39, 127.62, 120.51, 119.10, 94.71, 92.55, 76.95, 59.48, 56.11, 54.81, 53.48, 29.51, 24.91, 24.50, 23.97, 5.64, 3.31, −0.03. HRMS calcd for C$_{38}$H$_{31}$IN$_2$O$_4$ [M+H]$^+$, 587.1407; found, 587.1388.

N-((4aS,7R,12bS)-3-(Cyclopropylmethyl)-4a,9-dihydroxy-2,3,4,4a,5,6,7,7a-octahydro-1H-4,12-methanobenzofuro[3,2-e]isoquinolin-7-yl)-2-(3-iodophenyl)acetamide (MP1408). m-Iodophenyl acetic acid (15 mg, 0.057 mmol, 1.2 eq.) was added to a stirred solution of β-naloxamine (Majumdar et al., 2011) (19.6 mg, 0.057 mmol) in DMF (0.2 mL) at. HATU (26.1 mg, 0.068 mmol, 1.2 eq.) was added to the mixture at 0° C. at once and after 5 minutes, DIPEA (29.9 µL, 0.17 mmol, 3 eq.) was added and the reaction was continued at 0° C. to rt. After 2 hours, the reaction mixture was diluted with EtOAc (5 mL). The EtOAc layer was washed with brine (5×3 mL) to remove DMF, dried over anhydrous Na$_2$SO$_4$, filtered, and concentrated under reduced pressure. Then, the crude product was redissolved in methanol (1 mL) and treated with NaOMe in methanol (100 µL, 0.5 M) for 30 minutes. The solvent was removed under reduced pressure and the content was treated with EtOAc (5 mL) and the organic layer was washed with NH$_4$OH (5%, 1 mL), brine (3×3 mL), dried over anhydrous Na$_2$SO$_4$, filtered, and concentrated under reduced pressure. The crude product was purified by silica gel chromatography (ISCO flash column) using 3-7% MeOH in DCM. The product fraction was concentrated, redissolved in DCM (0.5 mL) and treated with boiling hexanes (3 mL), to remove the trace amount of tetramethyl urea byproduct, which upon cooling to room temperature furnished pure crystalline products MP1408; (13.2 mg, Yield; 40%) $^1$H NMR (600 MHz, CD$_3$OD) δ=7.68 (d, J=1.8 Hz, 1H), 7.59 (dt, J=7.9, 1.3 Hz, 1H), 7.30 (dt, J=7.8, 1.3 Hz, 1H), 7.08 (t, J=7.8 Hz, 1H), 6.63 (d, J=8.1 Hz, 1H), 6.57 (d, J=8.1 Hz, 1H), 5.84 (ddt, J=16.7, 10.2, 6.4 Hz, 1H), 5.30-5.10 (m, 2H), 4.42 (d, J=7.6 Hz, 1H), 3.66 (ddd, J=12.6, 7.6, 4.9 Hz, 1H), 3.54-3.39 (m, 2H), 3.22-3.02 (m, 3H), 2.92 (d, J=5.6 Hz, 1H), 2.68-2.52 (m, 2H), 2.25-2.07 (m, 2H), 1.81 (qd, J=12.9, 3.1 Hz, 1H), 1.63-1.51 (m, 2H), 1.47-1.35 (m, 2H). $^{13}$C NMR (151 MHz, MeOD) δ=173.07, 143.67, 139.40, 139.22, 139.22, 137.05, 136.05, 131.38, 131.36, 130.98, 129.66, 129.53, 120.28, 118.88, 94.91, 92.91, 71.59, 63.82, 59.83, 52.95, 43.27, 31.10, 25.27, 23.72, 4.92, 3.98. HRMS calcd for C$_{28}$H$_{32}$IN$_2$O$_4$ [M+H]$^+$, 587.1407; found, 587.1406.

(4bR,6R,8aS)-6-Amino-11-(cyclopropylmethyl)-3-methoxy-5,6,7,8,9,10-hexahydro-8aH-9,46-(epiminoethano)phenanthren-8a-ol (16). NH$_4$OAc (802.4 mg, 10.41 mmol, 20 eq.) was added to a stirred solution of known ketone (Zhang et al., 2007) 15 (177.7 mg, 0.52 mmol) in dry MeOH (4 mL) under argon at rt. The mixture was stirred for 8 hours. Then, NaCNBH$_3$ (163.6 mg, 2.60 mmol, 5 eq.) was added to the reaction mixture and the reaction was continued for overnight. The solvent was evaporated under reduced pressure and the content was stirred with aqueous HCl (1M, 10 mL) for 2 hours at rt. The aqueous layer was diluted with water (20 mL), basified with concentrated NH$_4$OH solution (to pH ~10) and then the product was extracted in DCM (3×15 mL). The combined DCM layer was washed with brine (10 mL), dried over anhydrous Na$_2$SO$_4$, filtered and concentrated. The crude product was purified by silica gel column chromatography using a mixture of 10% TEA and 1% MeOH in DCM. The β amine is more polar than a counterpart on using the condition, which was eluted later and upon drying furnished a white solid of the desired product 16 (P, 90 mg, Yield 51%); $^1$H NMR (600 MHz, CDCl$_3$) δ=6.99 (d, J=8.4 Hz, 1H), 6.86 (d, J=2.6 Hz, 1H), 6.69 (dd, J=8.4, 2.6 Hz, 1H), 4.65 (s, 1H), 3.78 (s, 3H), 3.00-2.91 (m, 2H), 2.77-2.66 (m, 2H), 2.56-2.48 (m, 1H), 2.38-2.27 (m, 2H), 2.15 (dd, J=13.2, 3.6 Hz, 1H), 2.07-2.00 (m, 2H), 1.80 (dd, J=13.2, 11.8 Hz, 1H), 1.63 (p, J=4.8 Hz, 2H), 1.54-1.41 (m, 2H), 1.09-1.00 (m, 1H), 0.86-0.78 (m, 1H), 0.50 (dd, J=8.1, 1.7 Hz, 2H), 0.12-0.06 (m, 2H). $^{13}$C NMR (151 MHz, CDCl$_3$) δ=158.4, 142.8, 128.3, 128.1, 111.1, 111.0, 68.7, 60.3, 59.4, 55.4, 46.4, 44.2, 42.3, 40.9, 37.0, 32.6, 31.2, 24.6, 9.6, 4.0, 3.9. ESI-MS m/z: 343.2 [M+H]$^+$.

N-((4bR,6R,8aS)-11-(Cyclopropylmethyl)-8a-hydroxy-3-methoxy-6,7,8,8a,9,10-hexahydro-5H-9,46-(epiminoethano)phenanthren-6-yl)-3-iodobenzamide (17). DIPEA (203 µL, 1.16 mmol, 3 eq.) and β-amine 16 (80 mg, 0.23 mmol) were added to the stirred solution of m-iodobenzoic acid (86.9 mg, 0.35 mmol, 1.5 eq.) dissolved in DMF (1 mL) at rt under an argon atmosphere. The reaction mixture was cooled to 0° C. and HATH (133.2 mg, 0.35 mmol, 1.3 eq.) was added to the reaction mixture. After stirring the reaction mixture for 4 hours at 0° C. to rt, the reaction mixture was poured into EtOAc (15 mL) and was washed with brine (5×15 mL). The EtOAc layer was dried over Na$_2$SO$_4$, filtered; and concentrated under reduced pressure. Then, the residue was purified by silica gel column chromatography using 2-5% MeOH in DCM. The desired product fractions were concentrated under reduced pressure and dried under high vacuum to get amorphous solid of the product 17; (110 mg, Yield 83%); $^1$H NMR (600 MHz, MeOD) δ=8.20 (t, J=1.7 Hz, 1H), 7.91 (dt, J=7.9, 1.3 Hz, 1H), 7.83 (dt, J=7.8, 1.3 Hz, 1H), 7.26 (t, J=7.8 Hz, 1H), 7.22-7.17 (m, 2H), 6.88 (dd, J=8.5, 2.5 Hz, 1H), 4.04-3.98 (m, 1H), 3.89 (s, 3H), 3.85 (s, 1H), 3.31-3.21 (m, 3H), 3.02 (d, J=12.5 Hz, 1H), 2.90 (s, 1H), 2.68 (s, 1H), 2.56-2.43 (m, 2H), 2.13 (t, J=12.7 Hz, 1H), 2.07-1.98 (m, 1H), 1.82-1.70 (m, 3H), 1.36-1.32 (m, 1H), 1.12 (dd, J=8.8, 4.2 Hz, 1H), 0.83 (d, J=8.7 Hz, 1H), 0.76 (td, J=8.8, 4.6 Hz, 1H), 0.51 (s, 2H). $^{13}$C NMR (151 MHz, MeOD) δ=168.1, 161.0, 141.5, 138.0, 137.5, 131.3, 130.2, 127.6, 115.1, 111.1, 94.6, 69.6, 62.5, 58.7, 55.9, 46.5, 42.2, 35.8, 31.7, 27.4, 25.4, 6.0, 3.4. ESI-MS m/z: 569.2 [M+H]$^+$.

N-((4bR,6R,8aS)-11-(Cyclopropylmethyl)-3,8a-dihydroxy-6,7,8,8a,9,10-hexahydro-5H-9,4b-(epiminoethano)phenanthren-6-yl)-3-iodobenzamide (MP1601). A solution of BBr$_3$ (874 µL, 0.87 mmol, 5 eq.) was added to the stirred solution of methyl ether 17 (100 mg, 0.17 mmol) dissolved in DCM (4 mL) at 0° C. under an argon atmosphere. The reaction was continued at 0° C. for 10 min and then at rt for 20 minutes. The reaction mixture was diluted with DCM (5 mL) and treated with aqueous NH$_4$OH (5%, 2 mL) for one hour. The, the DCM layer was separated and was washed with saturated solution of NaHCO$_3$ (2×10 mL), brine (5 mL), dried over anhydrous Na$_2$SO$_4$, filtered, and concentrated under reduced pressure. Then, the residue was purified by silica gel column chromatography using 10-15% MeOH in DCM. The desired product fractions were concentrated under reduced pressure and dried under high vacuum to get amorphous solid of MP1601; (72 mg, Yield 74%); $^1$H NMR (600 MHz, CDCl$_3$) δ=8.06 (d, J=1.8 Hz, 1H), 7.83-7.72 (m, 1H), 7.67 (dt, J=7.6, 1.2 Hz, 1H), 7.14 (t, J=7.8 Hz, 1H), 7.03 (d, J=2.5 Hz, 1H), 6.95 (d, J=8.3 Hz, 1H), 6.71 (dd, J=8.3, 2.4 Hz, 1H), 6.09 (s, 1H), 4.02 (tdt, J=11.9, 8.1, 4.2 Hz, 1H), 3.02 (d, J=18.2 Hz, 1H), 2.75 (d, J=18.0 Hz, 1H), 2.59 (s, 1H), 2.45-2.27 (m, 3H), 2.14 (t, J=15.5 Hz, 1H), 2.04 (d, J=5.9 Hz, 1H), 1.95-1.74 (m, 3H), 1.63 (td, J=13.3, 4.4 Hz, 1H), 1.55 (d, J=13.4 Hz, 1H), 1.31-1.16 (m, 1H), 1.14-1.03 (m, 1H), 0.86 (d, J=16.2 Hz, 1H), 0.52 (d, J=8.0 Hz, 2H), 0.13 (s, 2H). $^{13}$C NMR (151 MHz, CDCl$_3$) δ=165.3, 140.3, 136.6, 136.0, 130.3, 128.6, 126.1, 114.1, 112.0, 94.3, 68.8, 60.2, 59.3, 45.8, 44.1, 41.8, 36.3, 30.8, 27.9, 24.5, 4.0, 3.9. HRMS calcd for C$_{27}$H$_{32}$IN$_2$O$_3$ [M+H]$^+$, 559.1458; found, 559.1457.

Example 2—Biological Evaluation

A. MP1104 is a Balanced Agonist at G-Protein and Arrestin Signaling Pathways

Previously, the amidoepoxymorphinan ligand MP1104 (Varadi et al., 2015) was used to obtain the human KOR crystal structure in a nanobody-stabilized active state conformation (PDB code 6B73). Functional studies (cAMP and β-arrestin2 recruitment assays) showed that MP1104 is a balanced agonist (bias factor<1 for G-protein pathway) for both G-protein as well as β-arrestin2 pathways at mu and kappa receptors (Che et al., 2018). Its bias factors at hMOR and hKOR were determined to be 0.57 (FIGS. 1A & 1B) and 0.18 (FIGS. 1C & 1D), respectively. The potency and efficacy at G-protein activation as well as arrestin recruitment of MP1104 were evaluated using BRET assays which afford a more precise interrogation of transducer bias (Kruegel et al., 2016) in HEK-293T cells transfected with rodent opioids receptors (mMOR and rKOR). Confirming the cAMP inhibition assay and β-arrestin2 recruitment results obtained for human opioid receptors, MP1104 was found to be a balanced agonist at both mMOR (FIG. 2A) as well as mKOR (FIG. 3A) with bias factors of 0.1 and 0.23 respectively. The G-protein bias factor for each ligand was determined using functional data obtained from cAMP inhibition vs Tango assay or BRET assays, when applicable, by following previously reported calculation method (Kenakin et al., 2012).

B. Synthesis and Evaluation of MOR Biased and KOR Balanced Agonist MP1202

In contrast to MP1104, a related ligand IBNtxA (Majumdar et al., 2011) (FIG. 4B) with a hydroxyl (C14-OH) group and a saturated ring C, showed reduced β-arrestin2 recruitment at hMOR while acting as a balanced agonist at hKOR (FIGS. 5A-5D) (Che et al., 2018). At rodent receptors, the fact that IBNtxA shows strong G-protein bias was also confirmed at mMOR (FIGS. 5E-5G, bias factor=404) and retains balanced agonism at rKOR (FIGS. 5H & 5I, bias factor=0.6) As a continuation of structure-activity relationship (SAR) studies on 6β-amidoepoxymorphinans to identify the structural features responsible for β-arrestin2 recruitment over G-protein activation, MP1202 (C14-H instead of C14-OH in IBNtxA) was synthesized with the saturated cyclohexyl ring C (see synthesis in Example 1). Evaluation of MP1202 in radioligand binding assays in opioid transfected cell lines showed that it retained pan opioid sub-nM binding (Table 1) and sub-nM potency in the G protein pathway in GTPγS assays (Table 2). At human opioid receptors, MP1202 was similar to IBNtxA and was found to be G-protein biased at hMOR (bias factor=31, FIGS. 3G & 3H) while being a balanced agonist at hKOR (bias factor=0.6, FIGS. 3J & 3I).

TABLE 1

Receptor affinities of arylamidomorphinans in opioid tranfected cell lines

| | $K_i$ [nM][a] | | |
|---|---|---|---|
| Compd. | mMOR | mKOR | mDOR |
| IBNtxA | 0.11 ± 0.02 | 0.03 ± 0.001 | 0.24 ± 0.05 |
| MP1104 | 0.021 ± 0.00 | 0.0064 ± 0.0 | 0.08 ± 0.01 |
| MP1202 | 0.071 ± 0.031 | 0.11 ± 0.064 | 1.3 ± 0.8 |
| MP1207 | 0.23 ± 0.02 | 0.39 ± 0.05 | 15.62 ± 2.64 |
| MP1208 | 0.34 ± 0.01 | 0.28 ± 0.02 | 19.28 ± 6.48 |
| MP1305 | 0.25 ± 0.02 | 2.5 ± 0.3 | 11.7 ± 1.4 |
| MP1601 | 0.2 ± 0.01 | 2.13 ± 0.3 | 5.37 ± 0.9 |
| Morphine | 4.60 ± 1.81[b] | — | — |
| DAMGO | 3.34 ± 0.43[b] | — | — |
| U50, 488h | — | 0.73 ± 0.32[b] | — |
| DPDPE | — | — | 1.39 ± 0.67[b] |

[a]Competition studies were performed with the indicated compounds against $^{125}$IBNtxA (0.1 nM) in membranes from CHO cells stably expressing the indicated cloned mouse opioid receptors. $K_i$ values were calculated from the $IC_{50}$ values and represent the means ± SEM of at least three independent replications.
[b]Literature values (Váradi et al., 2015)

TABLE 2

[$^{35}$S]GTPγS Functional assays[a] in transfected cell lines

| | mMOR | | mKOR | | mDOR | | |
|---|---|---|---|---|---|---|---|
| Compd. | $EC_{50}$ (nM) | $E_{max}$ (%) | $EC_{50}$ (nM) | $E_{max}$ (%) | $EC_{50}$ (nM) | $E_{max}$ (%) | $IC_{50}$ (nM) |
| IBNtxA | 0.49 ± 0.12 | 101 ± 3 | 0.22 ± 0.02 | 102 ± 4 | 4.08 ± 0.67 | 95 ± 2 | — |
| MP1104 | 0.21 ± 0.03 | 103 ± 2 | 0.027 ± 0.002 | 104 ± 2 | 0.41 ± 0.11 | 88 ± 0 | — |
| MP1202 | 0.32 ± 0.03 | 68 ± 1 | 0.13 ± 0.02 | 94 ± 1 | 4 ± 1.6 | 71 ± 2 | — |
| MP1207 | 1.29 ± 0.65 | 41 ± 1 | 1.52 ± 0.07 | 39.3 ± 1.3 | nd | 10-15% | 27.34 ± 1.95 |
| MP1208 | 1.13 ± 0.05 | 54 ± 0.7 | 1.36 ± 0.23 | 43 ± 0.8 | nd | 10-15% | 11.39 ± 0.3 |
| MP1305 | 0.7 ± 0.1 | 81.2 ± 16 | 7.4 ± 1.8 | 42.2 ± 5.3 | 31.7 ± 3.6 | 22 ± 0.9 | — |
| MP1601 | 0.5 ± 0.2 | 45 ± 4.6 | 3 ± 0.7 | 72 ± 4.5 | 10 ± 1.6 | 67 ± 3.9 | — |
| DAMGO | 3.4 ± 0.2 | — | — | — | — | — | — |
| U50, 488h | — | — | 9.5 ± 1.8 | — | — | — | — |
| DPDPE | — | — | — | — | 16.2 ± 5.1 | — | — |

[a]Efficacy data were determined using an agonist induced stimulation of [$^{35}$S]GTPγS binding assay. Efficacy is represented as $EC_{50}$ (nM) and percent maximal stimulation ($E_{max}$) relative to standard agonist DAMGO (mMOR), DPDPE (mDOR), or U50, 488H (mKOR) at 1 μM. To determine the antagonistic properties of a compound, membranes were incubated with 100 nM of the appropriate agonist by varying its concentrations. Results are presented as nM ± SEM from three independent experiments performed as triplicate.

Figures 2A, 2B, 2C, 2D, 2E:
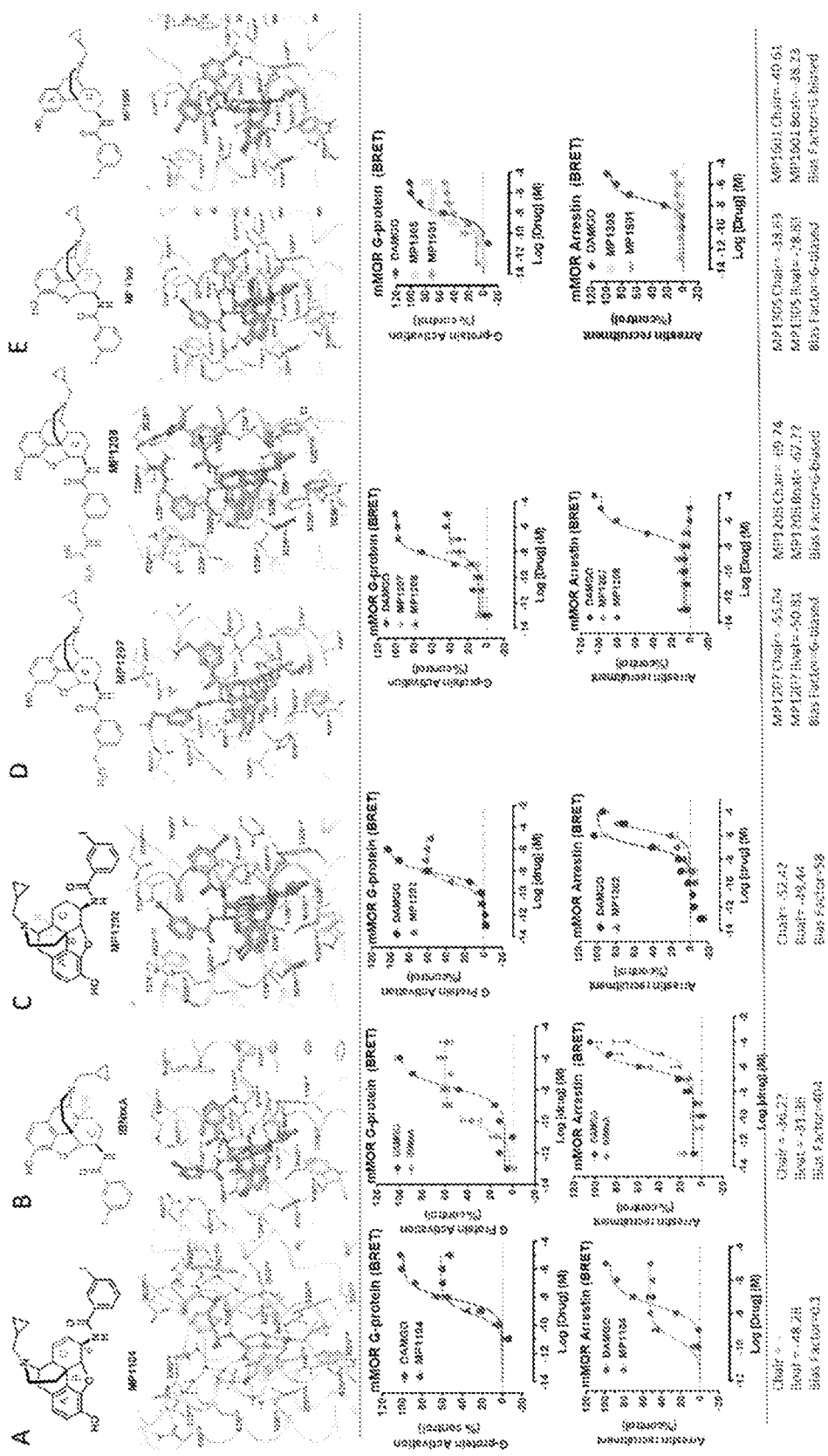
FIGS. 2A-2E shows the characterization of ligands (MP1104, IBNtxA, MP1202, MP1207, MP1208, MP1305 and MP1601) at mouse mu opioid receptor (mMOR) using BRET assays-chemical structure, docking in MOR, G-protein activity and arrestin recruitment, docking scores of chair/boat and bias factors.

At rodent receptors in BRET assays, MP1202 retained balanced agonism at rKOR (bias factor=0.39, FIG. 3C), although showing a diminished potency on β-arrestin2 recruitment at mMOR relative to DAMGO, resulting in a G-protein bias factor at MOR of 58 in BRET assays (FIG. 2C).

C. Predicted Engagement of the TM5-ECL2 Region Promotes G-Protein Bias

Figures 3A, 3B, 3C, 3D, 3E:
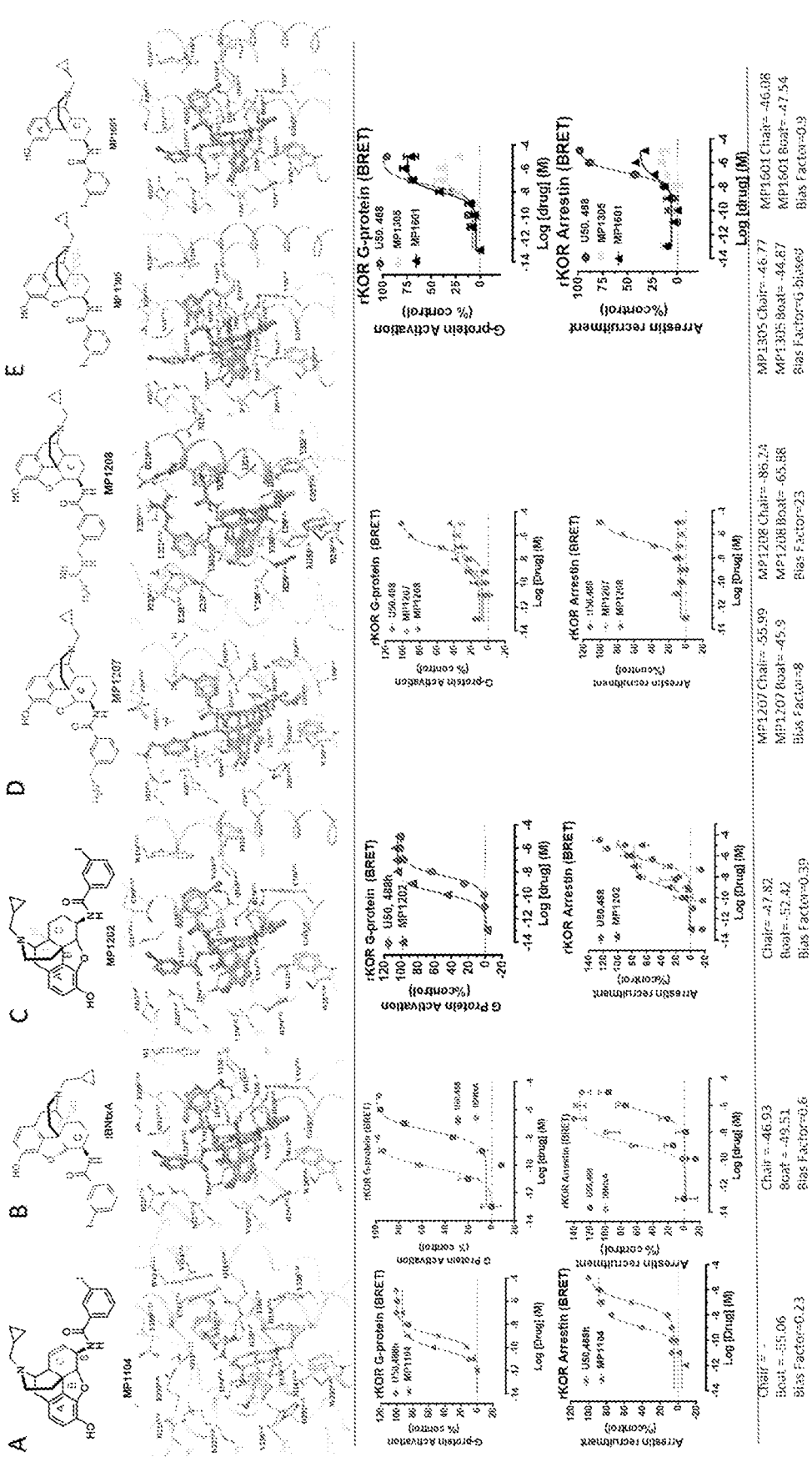
FIGS. 3A-3E shows the characterization of ligands (MP1104, IBNtxA, MP1202, MP1207, MP1208, MP1305 and MP1601) at rat kappa opioid receptor (rKOR) using BRET assays-chemical structures, docking in MOR, G-protein activity and arrestin recruitment, docking scores of chair/boat and bias factors.
Figures 4A, 4B:
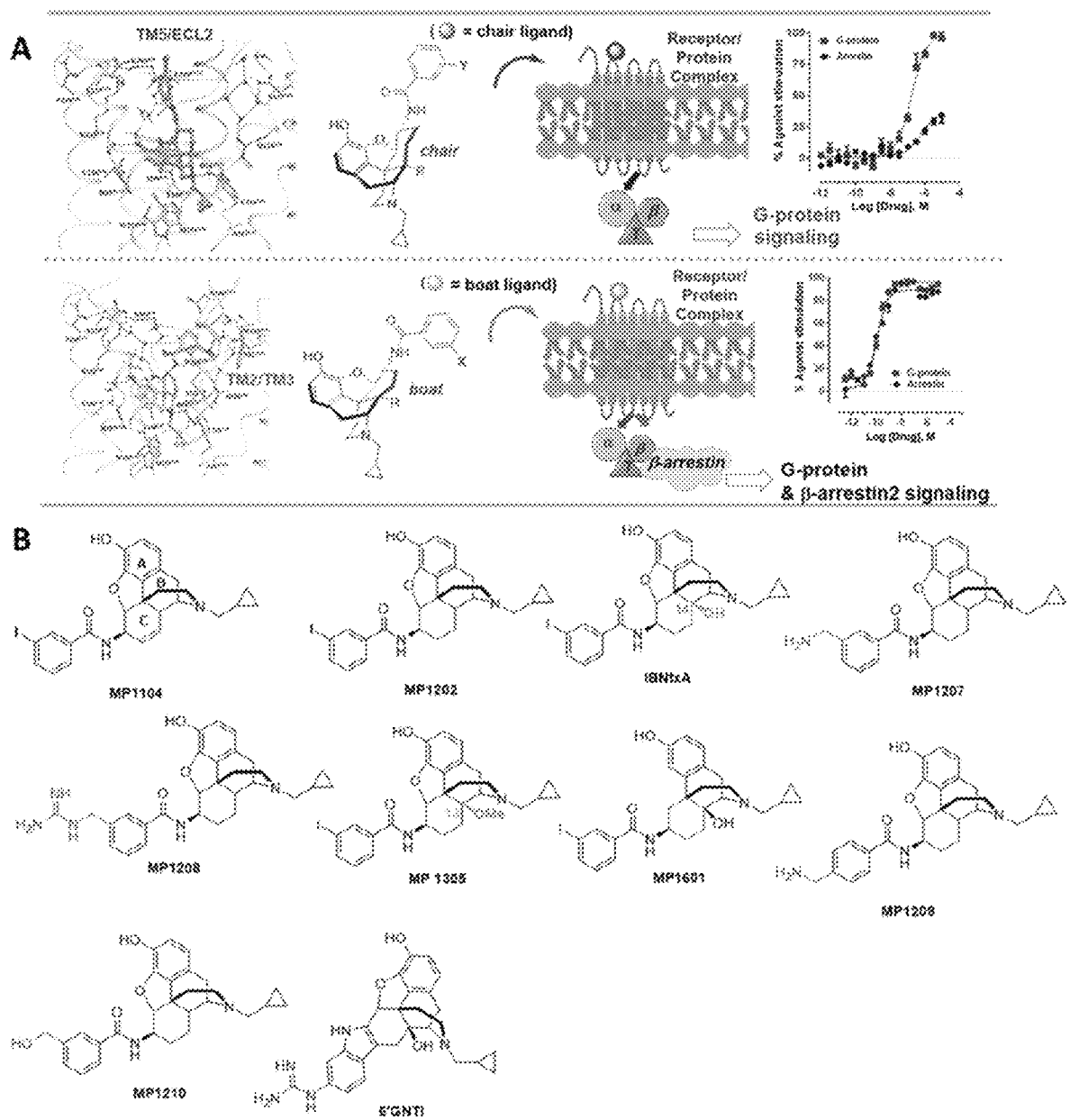
FIGS. 4A & 4B show the design concept, structures of ligands synthesized and evaluated, and bias factors at opioids receptors.
Figures 5A, 5B, 5C, 5D, 5E, 5F, 5G, 5H, 5I:
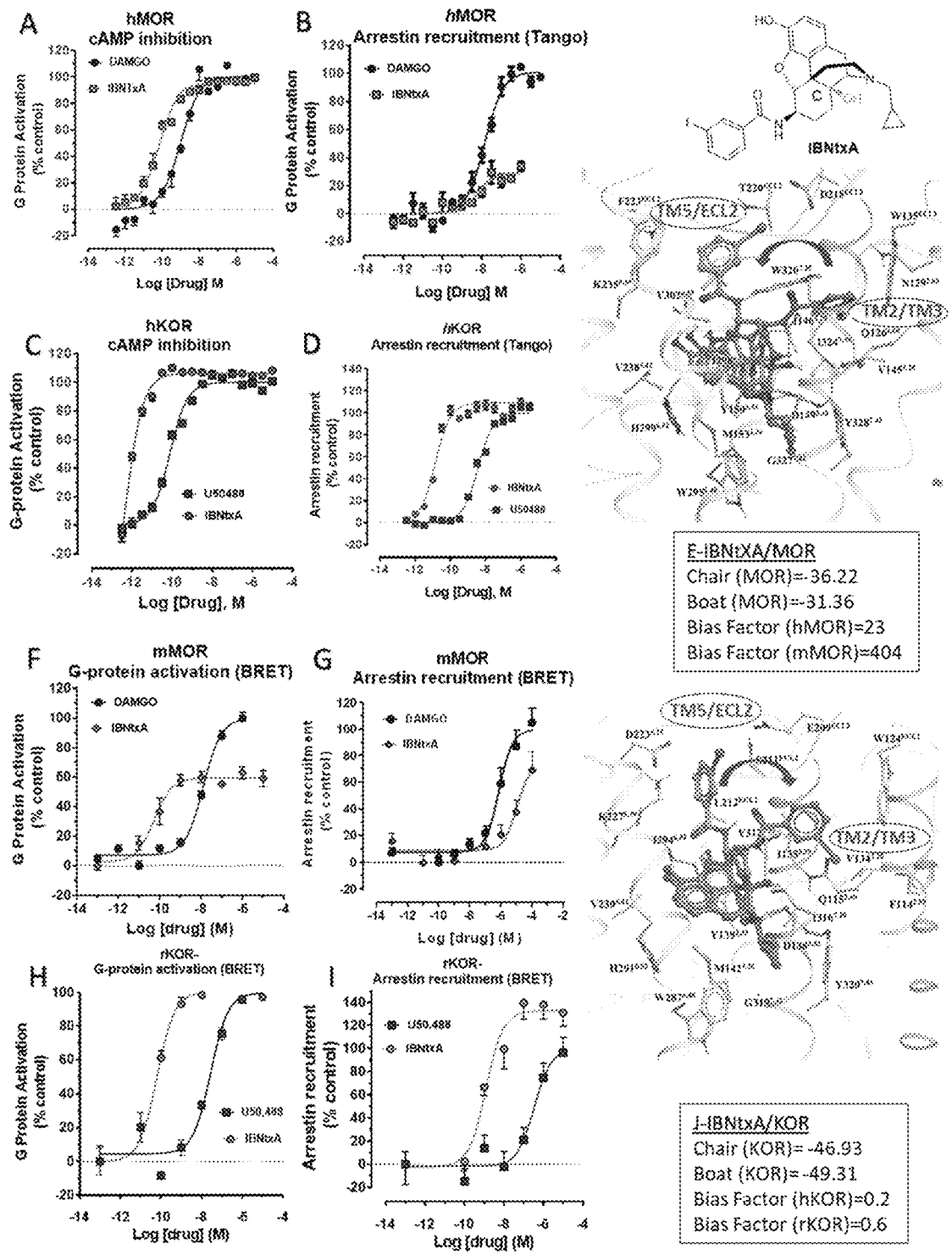
FIGS. 5A-5I shows IBNtxA showed a balanced agonism at KOR and G-protein biased agonism at MOR.

Differences in the bias profiles of MP1104, IBNtxA, and MP1202 suggested distinct interaction modes of these ligands at MOR and KOR. Both the ligand-based and the receptor-based structure design approaches were relied upon to understand the observed pharmacology. In terms of ligand structure, the three ligands have two structural variations among them: the presence/absence of C14-OH and the saturation/unsaturation of the ring C (FIG. 4B). The similarity of the bias profiles for IBNtxA and MP1202 suggested that C14-OH is not important for bias. However, the contrast between the strong bias of IBNtxA and MP1202 and balanced agonism of MP1104 at MOR suggested a useful SAR between the conformation of the C ring and ligand function. Indeed, a strong preference was found for the unsaturated ring C of MP1104 to be in the boat conformation, based on analysis of similar ligands in the Crystallography Open Database and the quantum mechanics (QM) energy calculations. At the same time, the saturated C rings of both IBNtxA and MP1202 could assume both chair and boat conformations with only a modest preference for chair conformation (Tables 3 & 4). To analyze the differences between boat and chair conformations of the C rings in the context of ligand-receptor interactions, energy-based docking studies were performed for these ligands in all-atom models of the receptors, based on recently solved active-state crystal structures for MOR (Huang et al., 2015) and KOR (Che et al., 2018). Due to the boat-form restriction for the unsaturated ring C, the amidophenyl moiety of the best-scored docking poses for MP1104 in both MOR and KOR occupied a sub-pocket between TM2 and TM3 (FIGS. 3E & 3F). In the absence of such conformational limitation for the saturated ring C in IBNtxA and MP1202, both chair and boat conformations of the ring were observed among the top 10 poses ranked by energy score. However, IBNtxA (FIG. 5E) and MP1202 (FIG. 3K) were found to be the best-scored docking poses with MOR consistently adopted chair conformation of ring C, while in KOR the best-scored poses adopted boat conformation (FIGS. 5J and 3L).

TABLE 3

Energy calculated by computational QM calculations.

| Ligand (Basis set) | Energy(Chair-Boat) HF | Energy(Chair-Boat) kcal/mol | Energy (Chair-Boat) kJ/mol |
|---|---|---|---|
| MP1104 (LanL2DZ) | 0.03671637 | 23.0396323 | 96.3988294 |
| MP1104 (DGDZVP) | 0.03493887 | 21.9242457 | 91.7320032 |
| IBNtxA (LanL2DZ) | −0.0014450 | −0.90674184 | −3.7938475 |

TABLE 3-continued

Energy calculated by computational QM calculations.

| Ligand (Basis set) | Energy(Chair-Boat) HF | Energy(Chair-Boat) kcal/mol | Energy (Chair-Boat) kJ/mol |
|---|---|---|---|
| IBNtxA (DGDZVP) | −0.0016583 | −1.040599833 | −4.353869701 |
| MP1202 (LanL2DZ) | −0.01402513 | −8.8009031585 | −36.822978815 |
| MP1202 (DGDZVP) | −0.011652 | −7.31174652 | −30.59234743997 |

TABLE 4

Best docking scores of each ligand with a chair or a boat conformation at active state human mu and kappa opioid receptors and ligand bias factor towards G-protein at human and rodent opioid receptors.

| Drugs | MP1104 | IBNtxA | MP1202 | MP1207 | MP1208 | MP1305 | MP1601 | 6'GNTI | MP1209 | MP1210 |
|---|---|---|---|---|---|---|---|---|---|---|
| Docking score of Chair/hMOR | — | −36.22 | −52.42 | −55.04 | −69.74 | −38.63 | −40.61 | | −51.03 | −44.17 |
| Boat/hMOR | −48.28 | −31.36 | −49.44 | −50.81 | −67.72 | −28.83 | −38.23 | | −43.67 | −36.18 |
| Chair/hKOR | — | −46.93 | −47.82 | −55.99 | −86.24 | −46.77 | −46.08 | −64.86 | −57.63 | −53.91 |
| Boat/hKOR | −55.06 | −49.51 | −52.42 | −45.9 | −65.88 | −44.87 | −47.54 | | −60.77 | −55.43 |
| Bias factor (G-protein)/hMOR | 0.57 | 23 | 31 | nd | nd | 11 | 4 | | nd | nd |
| /mMOR | 0.1 | 404 | 58 | nd | nd | nd | nd | | | |
| /hKOR | 0.18 | 0.2 | 0.6 | 8 | 23 | 4 | 0.15 | | 0.6 | 1.2 |
| /rKOR | 0.23 | 0.6 | 0.39 | nd | nd | nd | 0.9 | | | |

These reproducible differences between KOR and MOR can be explained by different physical properties of their TM2/TM3 sub-pockets, which accommodate the hydrophobic amidophenyl arm of these ligands. This sub-pocket is more hydrophobic in KOR because of the presence of the non-conserved VI $18^{2.63}$ residue and a conformational change in the conserved $Q115^{2.60}$ residue. Although the MOR sub-pocket does share some hydrophobic residues, namely $W^{ECL2}$, $V^{3.28}$ and $I^{3.29}$, exposed polar groups of $N129^{2.63}$ and $Q126^{2.60}$ side chains increase the polarity. Therefore, while in KOR the hydrophobic amidophenyl arm of the ligand retains its preference for binding the TM2-TM3 sub-pocket, in MOR it is preferentially redirected towards TM5-ECL2 region. Without wishing to be bound by any theory, it is believed that this binding interaction preference of the amidophenyl arm of IBNtxA and MP1202 is reflected in the switching of the C-ring from the chair conformation when bound in MOR to the boat conformation when interacting with KOR. Notably, this concerted switch of C-ring conformation and the amidophenyl "arm" position correlates with the observed signaling bias. Specifically, whereas the chair conformation of IBNtxA and MP1202 ligands in MOR results in the "arm" interactions with TM5-ECL2 region and favors G-protein activation, while boat conformation in KOR results in TM2-TM3 sub-pocket interactions and balanced activation. This observation is further corroborated by the balanced activation in both MOR and KOR found for the boat-restricted MP1104 ligand.

D. Structure-Inspired Design of MP1207 and MP1208 as Dual MOR/KOR G-Protein Biased Agonists.

Figure 6:
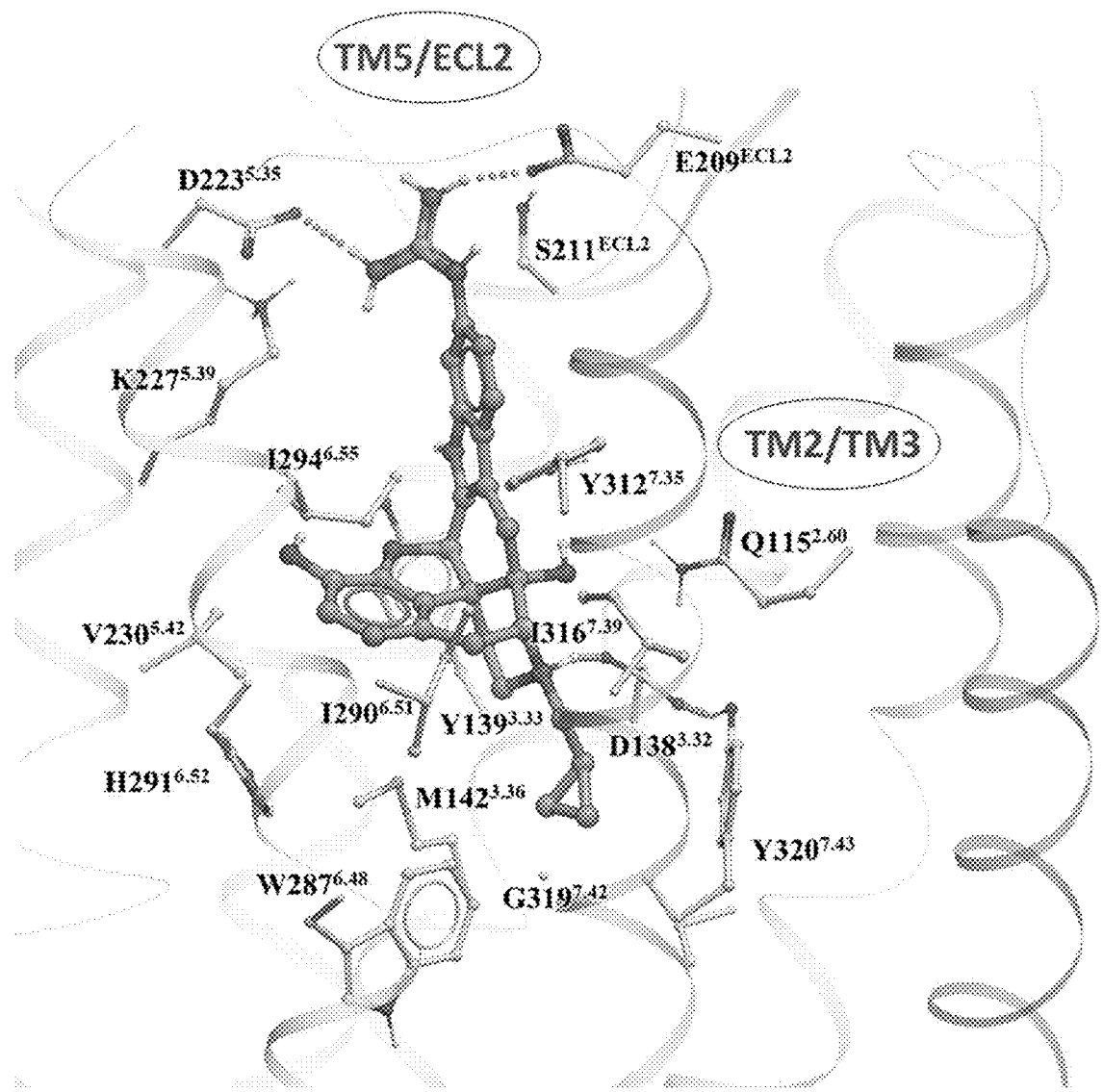
FIG. 6 show the preferred docking pose of known KOR biased ligand 6'GNTI (chair form, orange stick) at an active state of KOR with the guanidino group engaging a region between TM5 and ECl2. Note: possible engagement of residues D223 and E209 similar to MP1207 and MP1208 in TM5-ECL2 region.

Based on the above analysis, it was hypothesized that a structure-inspired design of MP1202 analogs that are G-protein biased not only at MOR, but also at KOR would require a switch in preference of amidophenyl arm substituents from the TM2-TM3 sub-pocket to the TM5-ECL2 region in both receptors. To test this hypothesis, the MP1202 ligand was redesigned by introducing a polar or charged moiety at the amidophenyl "arm" to make its interactions at the hydrophobic TM2-TM3 pocket of KOR unfavorable. Further, since the TM5-ECL2 region in KOR is lined by acidic residues $D223^{5.35}$ and $E209^{ECL2}$, the presence of basic moieties at the amidophenyl arm will provide additional favorable interactions to shift its preference towards the TM5-ECL2 region. Interestingly, in the docking pose for 6'GNTI in KOR, a known G-protein biased ligand (Rives et al., 2012; Schmid et al., 2013), the guanidino group also occupies the TM5-ECL2 region (FIG. 6).

As a part of the computer assisted design, a library of analogs was proposed where the m-iodo group was swapped with polar groups such as OH, $NH_2$ $NMe_2$, $(CH_2)_nNH_2$ and $(CH_2)_n$-guanidine (n=1-5 for amine and guanidine modification). Docking of these derivatives into the active state KOR structural model allowed computational predictions of their binding scores and conformational preferences (Table 5). Two analogs, calculated to have the greatest preference for the ring C chair form and interactions with the TM5-ECL2 region at both MOR and KOR MP1207 and MP1208 (FIGS. 4B, 7C-D and 7G-H) were selected and synthesized (Example 1).

TABLE 5

Docking scores for proposed analogs of MP1202, where m-iodo group is substituted with a polar moiety (R).

| Serial | R | Chair score | Boat score | Scores for chair preference |
|---|---|---|---|---|
| 1 | -m$NH_2$ | −55.35 | −58.47 | +3.12 |
| 2 | -mN$(CH_3)_2$ | −51.81 | −48.34 | −3.47 |
| 3 | -mOH | −54.81 | −57.34 | +2.53 |
| 4 (MP1207) | -m$CH_2NH_2$ | −55.99 | −45.9 | −10.09 |
| 5 | -m$CH_2CH_2NH_2$ | −59.42 | −51.79 | −7.63 |
| 6 | -m$CH_2CH_2CH_2NH_2$ | −64.07 | −49.91 | −14.16 |
| 7 | -m$CH_2CH_2CH_2CH_2NH_2$ | −52.42 | −49.67 | −2.75 |
| 8 | -mguanidine | −76.29 | −66.34 | −9.95 |
| 9 (MP1208) | -m$CH_2$guanidine | −86.24 | −65.88 | −20.36 |
| 10 | -mCOguanidine | −82.09 | −77.53 | −4.56 |
| 11 | -p$CH_2NH_2$ | −57.63 | −60.77 | +3.14 |
| 12 | -m$CH_2OH$ | −53.91 | −55.43 | +1.5 |

Figures 7A, 7B, 7C, 7D, 7E, 7F, 7G, 7H:
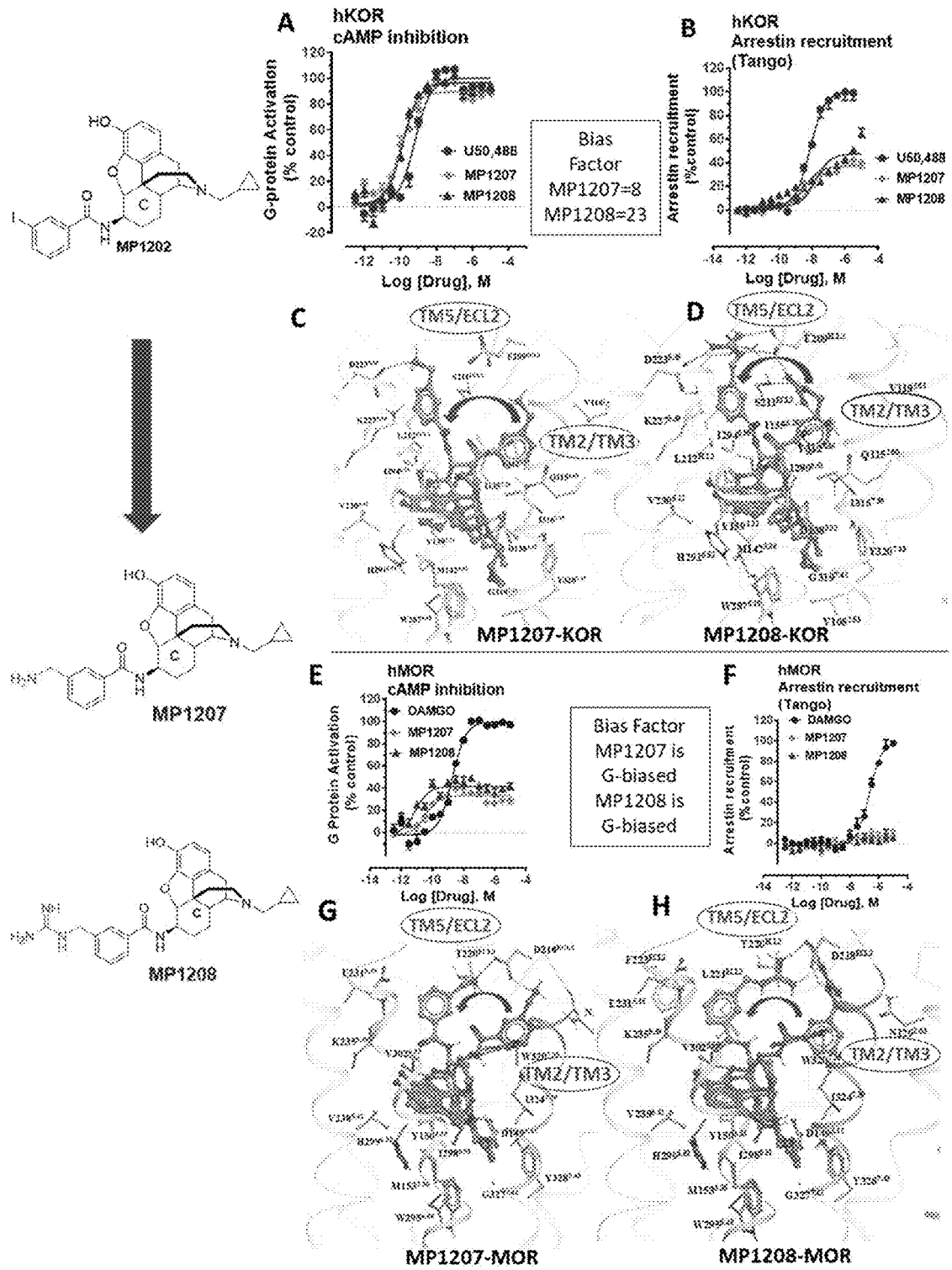
FIGS. 7A-7H show meta-Amino (MP1207) and meta-guanidino (MP1208) analogs prefer the chair conformation and target the TM5-ECL2 region and are G-protein biased agonists at KOR and MOR.
Figures 8A, 8B, 8C, 8D, 8E, 8F, 8G, 8H, 8I, 8J, 8K:
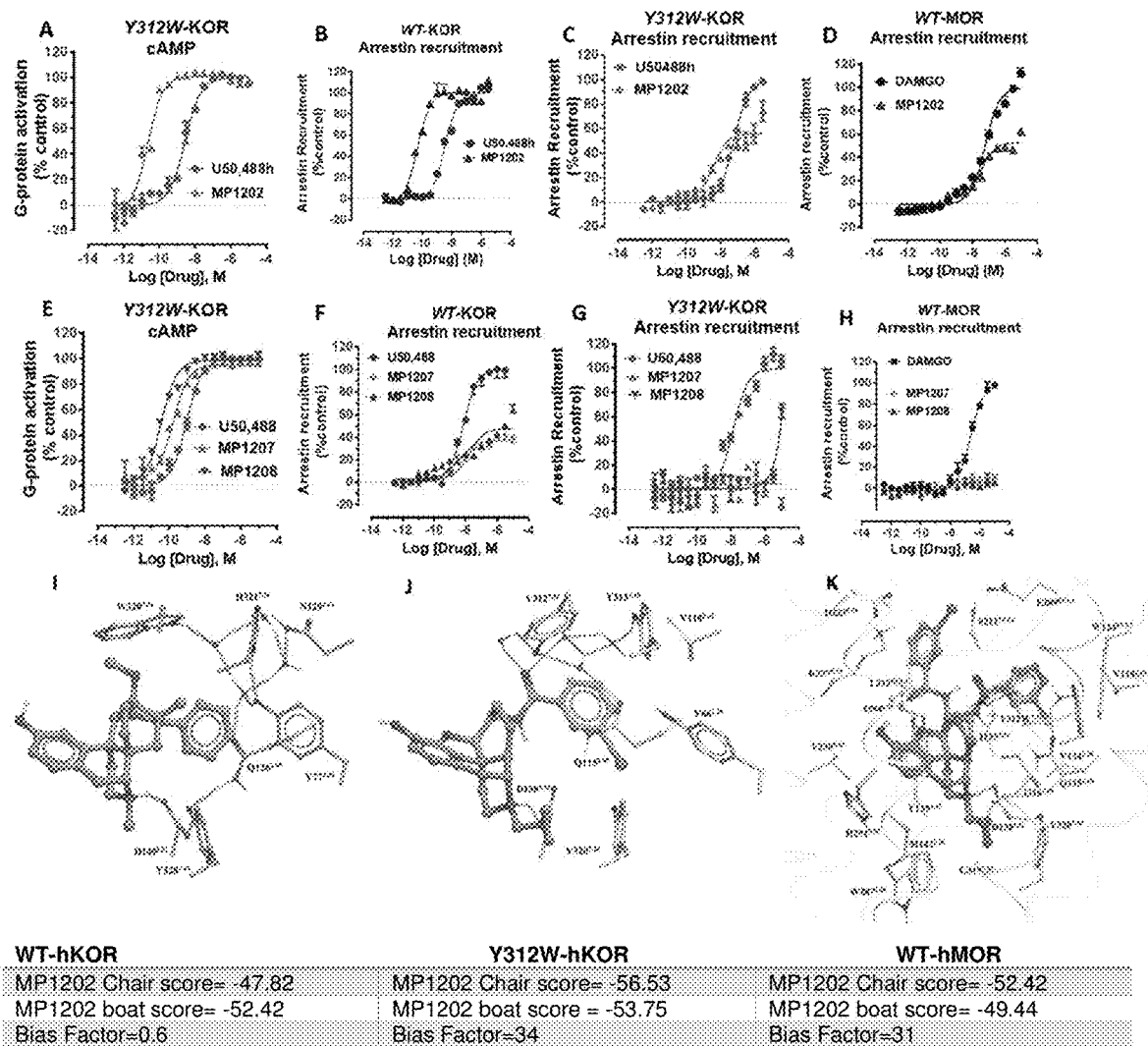
FIGS. 8A-8K show mutation of KOR Y312W leads to a receptor mimicking MOR arrestin recruitment. MP1202 flips to a G-protein agonist and arrestin recruitment for MP1207 and MP1208 is reduced.

Functional studies using c AMP inhibition and Tango assays at human opioid receptors showed that both MP1207 and MP1208 are G-protein biased agonists at hKQR with bias factors of 8 and 23 (FIGS. 7A & 7B) respectively. At hMOR, no recruitment of arrestin was seen for either ligand at ail, consistent with a strongly biased G-protein partial agonism at MOR as well (FIGS. 7E & 7F). In binding assays, both MP1207 (m-amine group) and MP1208 (m-guanidine group) showed similar affinities at mMOR ($K_i$=0.23 nM and 0.34 nM) and m KOR ($K_i$=0.39 and 0.28 nM) with substantial selectivity over mDOR ($K_i$=15.62 and 19.28 nM) (Table 2). In [$^{33}$S]GTPγS binding assays both MP1207 and 1208 were partial agonists at both mKOR and mMOR, still maintaining very high potency at mKOR ($EC_{50}$=1.5 and 1.4 nM) and at mMOR ($EC_{50}$=1.3 and 1.1 nM). At mDOR both MP1207 and 1208 show only weak efficacy. (Table 2 & 6). Similar results of partial agonism at mMOR (FIG. 2D) and rKQR (FIG. 3D) with no recruitment of βarrestin-2 were seen when rodent opioid receptors were used in BRET assays. The arrestin recruitment signal for both MP1207 and MP1208 at hMOR, mMOR and rKOR were too low for the bias factors at these receptors to be calculated.

strong G-protein bias (bias factor=33, FIGS. 8A & 8C) from being a balanced agonist in the wild-type KOR (bias factor=0.6, FIGS. 8B & 8D). A similar trend was found with MP12-07 and 1208, revealing a further reduction of arrestin recruitment at the mutant KOR receptor (FIGS. 8E-8G), down to the level seen in wild type MOR (FIGS. 8H). These results suggest that similar to IBNtxA, the $Y312W^{7.35}$ mutation in KOR changes the conformational character of the sub-pocket to MOR-like, possibly by changing the conformation of $Q115^{2.60}$, and also leads to loss of water-mediated hydrogen bonding with the amido group. Therefore, $Y312W^{7.35}$ provides an environment which favors the

TABLE 6

Functional studies at DOR using cAMP inhibition & Tango-arrestin and BRET assays

A. Functional data at hDOR using cAMP inhibition and Tango-arrestin assays

| | cAMP inhibition | | Arrestin recruitment | |
|---|---|---|---|---|
| Compd. | $EC_{50}$, nM (pEC50 ± SEM) | $E_{max}$ % ± SEM | $EC_{50}$, nM (pEC50 ± SEM) | $E_{max}$ % ± SEM |
| IBNtxA | 0.43(9.3 ± 0.03) | 106 ± 1 | 14.1(7.8 ± 0.06) | 224 ± 5 |
| DPDPE(CTRL.) | 0.69(9.1 ± 0.07) | 100 ± 2 | 2.99(8.5 ± 0.04) | 100 ± 1.5 |
| MP1104 | 0.40(9.4 ± 0.04) | 99 ± 1.1 | 3.73(8.4 ± 0.06) | 189 ± 5.5 |
| DADLE (CTRL.) | 0.66(9.2 ± 0.05) | 100 ± 1.3 | 0.349(9.45 ± 0.10) | 100 ± 3.2 |
| MP1202 | 8.18(8.1 ± 0.06) | 99 ± 2.2 | 18.14(7.7 ± 0.25) | 26 ± 3.1 |
| DADLE (CTRL.) | 1.45(8.8 ± 0.06) | 100 ± 2 | 8.41(8.1 ± 0.08) | 100 ± 2.7 |
| MP1207 | 11.4(7.9 ± 0.1) | 38 ± 2 | 64.06(7.2 ± 0.23) | 34 ± 3.7 |
| MP1208 | 2.49(8.6 ± 0.13) | 39 ± 1.8 | 3624.0(5.5 ± 0.27) | 62 ± 16.7 |
| DADLE (CTRL.) | 0.48(9.3 ± 0.05) | 100 ± 1.5 | 1.41(8.8 ± 0.07) | 100 ± 2.3 |
| MP1305 | 74.18(7.1 ± 0.08) | 71 ± 2.4 | 227.5(6.6 ± 0.06) | 89 ± 2.8 |
| MP1601 | 2.76(8.6 ± 0.06) | 106 ± 2.3 | 86.7(7.1 ± 0.06) | 203 ± 5.4 |
| DPDPE(CTRL.) | 0.69(9.1 ± 0.07) | 100 ± 2 | 2.99(8.5 ± 0.04) | 100 ± 1.5 |

B. Functional data at mDOR using BRET assays

| | G-Protein activation | | Arrestin recruitment | |
|---|---|---|---|---|
| Compd. | $EC_{50}$, nM (pEC50 ± SEM) | $E_{max}$ % ± SEM | $EC_{50}$, nM (pEC50 ± SEM) | $E_{max}$ % ± SEM |
| IBNtxA | 0.48(9.3 ± 0.10) | 108 ± 3.7 | 26.6(7.5 ± 0.2) | 88 ± 6.8 |
| DPDPE(CTRL.) | 2.72(8.5 ± 0.09) | 100 ± 3 | 184.3(6.73 ± 0.1) | 100 ± 6.4 |
| MP1104 | 1.4(8.9 ± 0.06) | 91 ± 1.7 | 26.0(7.6 ± 0.11) | 40 ± 1.7 |
| DPDPE(CTRL.) | 1.3(8.9 ± 0.04) | 100 ± 1.2 | 98.0(7.0 ± 0.04) | 100 ± 1.8 |
| MP1202 | 7.03(8.1 ± 0.15) | 103 ± 4.6 | 524.8(6.3 ± 0.20) | 26 ± 2.3 |
| DPDPE(CTRL.) | 2.19(8.6 ± 0.10) | 100 ± 3.5 | 109.3(6.7 ± 0.06) | 100 ± 3 |
| MP1207 | 116.4(6.9 ± 0.12) | 52 ± 2.3 | nd | nd |
| MP1208 | 26.6(7.6 ± 0.20) | 58 ± 3.3 | nd | nd |
| MP1305 | 40.4(7.4 ± 0.20) | 105 ± 5.9 | nd | nd |
| MP1601 | 6.27(8.2 ± 0.20) | 105 ± 6.7 | 9.0(8.0 ± 0.33) | 16 ± 1.4 |
| DPDPE(CTRL.) | 0.44(9.3 ± 0.13) | 100 ± 2.5 | 21.8(7.6 ± 0.04) | 100 ± 1.3 |

The functional data of each assay using human delta opioid receptor (hDOR) and mouse delta opioid receptor (mDOR) were normalized to $E_{max}$ of corresponding controls DPDPE or DADLE. Results were analyzed using a three-parameter logistic equation in GraphPad Prism and the data are presented as mean $EC_{50}$(p$EC_{50}$ ± SEM) with $E_{max}$ % ± SEM for assays run in triplicate; CTRL.; control compound and nd; results could not be determined because of no measurable arrestin recruitment signal.

E. Mutations and Additional MP1207 Analog Design Validate TM5-ECL2 Region in Signaling Bias Conversely, the design hypothesis also suggests that the relocation of the amidophenyl arm can be achieved by hampering its interactions in TM2/TM3 subpocket. Indeed, previously work had shown that a mutation of $Y312W^{733}$ in the TM2-TM3 region of KOR flips IBNtxA from being a balanced agonist to being G-biased (Che et ah, 2018). While the residues in this position do not make direct contact with the receptor in the models, it is likely to impact binding indirectly (See FIG. 8I showing Bu72-MOR TM2-TM3 and FIG. 8J showing MP1202-KOR TM2-TM3 region interactions).

In the present study, the effects of the $Y312W^{735}$ mutation on MP1202, MP1207 and MP1208 were analyzed. As expected, this mutation in KOR reduced arrestin recruitment by MP1202 to the level observed for MOR, resulting in chair conformation, leading to a flip in bias towards enhanced G-protein activity (FIG. 8K).

Figures 9A, 9B, 9C, 9D:
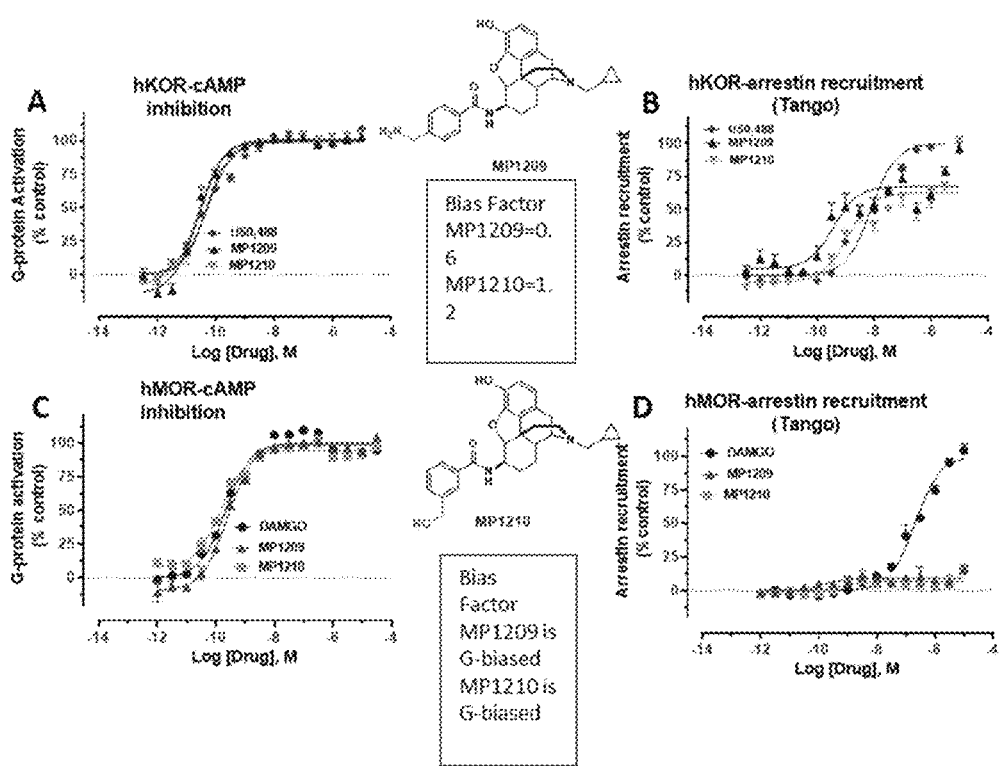
FIGS. 9A-9D show analogs of MP1207 not oriented towards TM5-ECL2 region suggest G-protein bias of MP1207/08 is dependent on salt-bridge formation in this region.

To evaluate if a salt bridge provides impetus for the ligand to adopt the chair form and amidophenyl arm to be located in TM5-ECL2 region, two MP1207 analogs were synthesized by swapping the m-$CH_2NH_2$ with p-$CH_2NH_2$ (MP1209) and m-$CH_2OH$ (MP1210) (FIG. 4B, Scheme 1). Consistent with the predictions (Tables 4 & 5), the para-substituted and more planar analog, MP1209 and the meta substituted methyl hydroxyl analog (MP1210) which are incapable of forming a salt bridge with $D223^{5.53}$ and $E209^{ECL2}$ lost hKOR bias (bias factors 0.6 and 1.2 respectively for MP1209 and MP1210, FIGS. 9A & 9B) while retaining hMOR null arrestin recruitment (FIGS. 9C & 9D). Thus, only when ideal orientation/distances are maintained (i.e. meta-amino/guano), the amidophenyl mm is accommodated in TM5-ECL2 region of KOR, a bias for G-protein activity is seen. Taken together, the described mutational analysis combined with assessment of epoxymorphinan analogs targeting in TM5-ECL2 region further corroborated the hypothesis that interactions in this region can be useful for G-protein bias at KOR.

F. Design of Other Morphinan Analogs Engaging TM5 Validate Signaling Bias

Figures 10A, 10B, 10C, 10D, 10E, 10F, 10G, 10H, 10I, 10J, 10K, 10L:
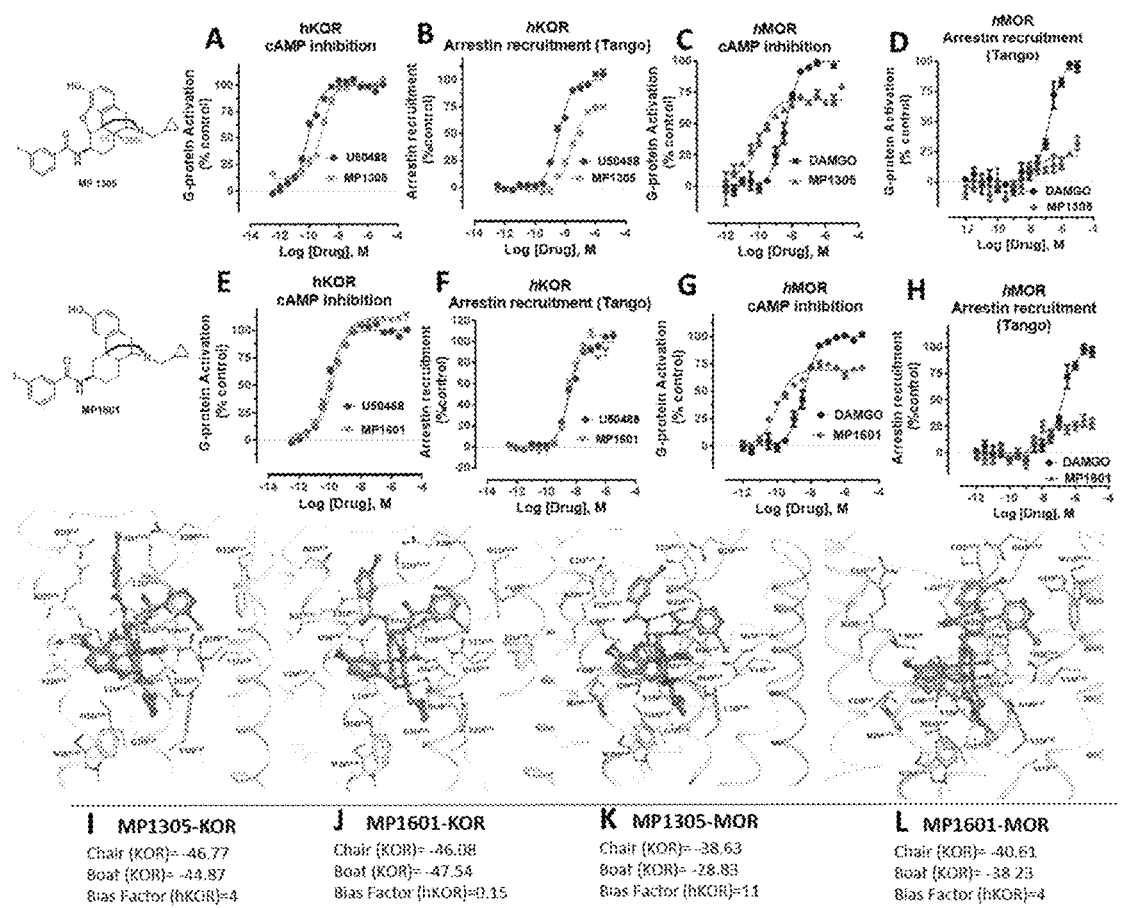
FIGS. 10A-10L shows that at human receptors, MP1305 is G-biased at MOR and KOR whereas MP1601 is G-biased at MOR and balanced at KOR.
Figures 11A, 11B, 11C, 11D, 11E, 11F:
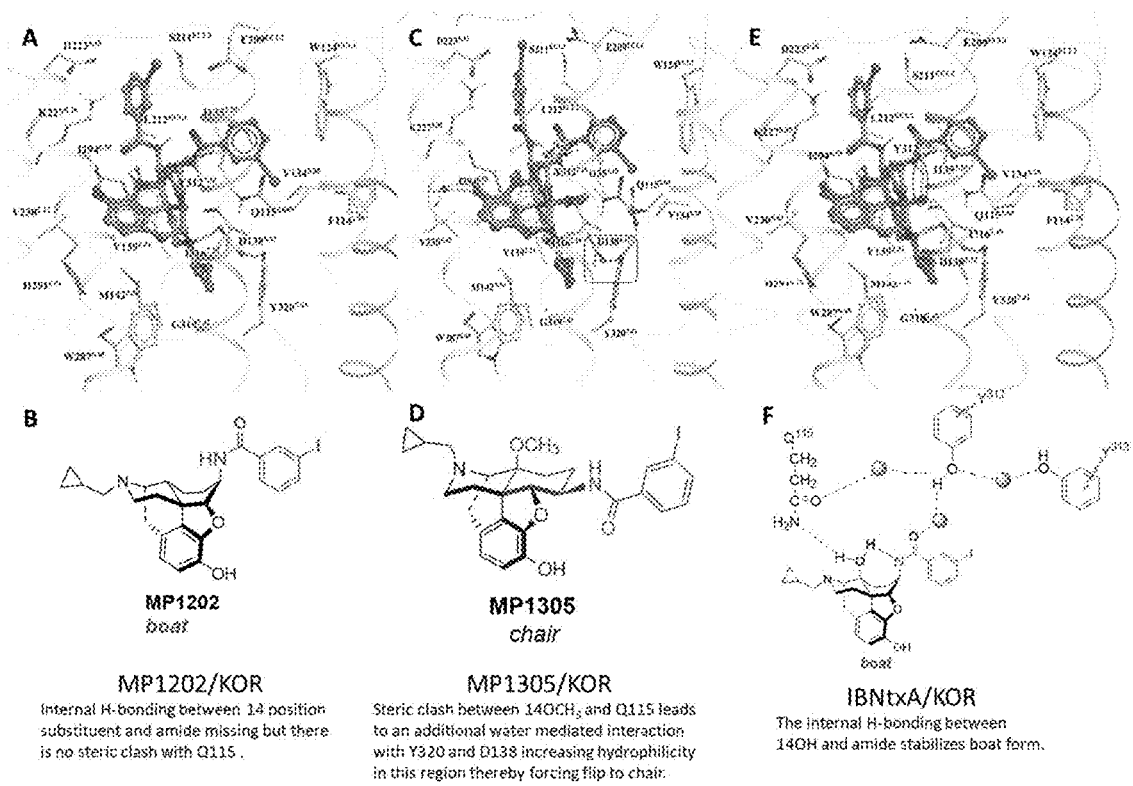
FIGS. 11A-11F show MP1305 is G-protein biased at KOR. Docking pose for ligands inside active state KOR shown in white carbon sticks and white ribbon representations.

Continuing with epoxymorphinan/morphinan SAR, m-iodo analogs MP1305 (methylated OH as C14-OCH$_3$), and MP1601 from morphinan template (devoid of the etheral bridge linking rings A and C) were synthesized (See Example 1). Computational docking studies suggested that ring C of MP1305 prefers the chair form at both MOR and KOR (See FIGS. 10I-10K and 11 for details), while MP1601 favors the chair form at MOR and boat form at KOR (FIGS. 10J & 10L). Consistent with the docking predictions, MP1305 was found to be G-protein biased at MOR and KOR at human receptors with a bias factor of 11 and 4, respectively (FIGS. 10A-10D) while MP1601 behaved similar to IBNtxA and MP1202, a balanced agonist at hKOR at human (bias factor=0.15, FIGS. 11E-11F) while being G-protein biased at hMOR (Bias factored, FIGS. 10G & 11H).

At rodent receptors, both compounds showed sub-nM binding and high potencies in [$^{35}$S]GTPγS assays (Tables 1 and 2). Due to very low arrestin signal, it was impossible to calculate the bias factor at rodent receptors from the BRET assays at MOR for both MP1305 and 1601 and for MP1601 at KOR (FIGS. 2 & 3). MP1601 at rKOR behaved similar to hKOR and was a balanced agonist (bias factor=0.9, FIG. 3E). These results are again consistent with the hypothesis correlating G-protein bias of the morphinan derivatives with their C-ring chair conformation and the resulting positioning of the amidophenyl arm in the TM5-ECL2 region.

G. In Vivo Pharmacology of Dual G-Protein Biased MOR/KOR Agonists

Analgesia of the dual biased agonists MP1207 and MP1208 was evaluated in vivo in mice using a standard tail withdrawal assay, with the compounds administered supraspinally (icv). The antinociceptive ED$_{50}$ (and 95% CI) values of MP1207 and MP1208 were 6.1 (4.1-8.9) nmol (FIG. 12A), and 19.8 (12.6-34.0) nmol respectively, were comparable to that of the kappa agonist U50,488h, 8.62 (5.74-11.9) nmol, though slightly higher than the reported ED$_{50}$ of morphine, 2.35 (1.13-5.03) nmol, icv (using the same assay as previously stated (Aldrich et at, 2014)).

Figures 12A, 12B, 12C, 12D, 12E:
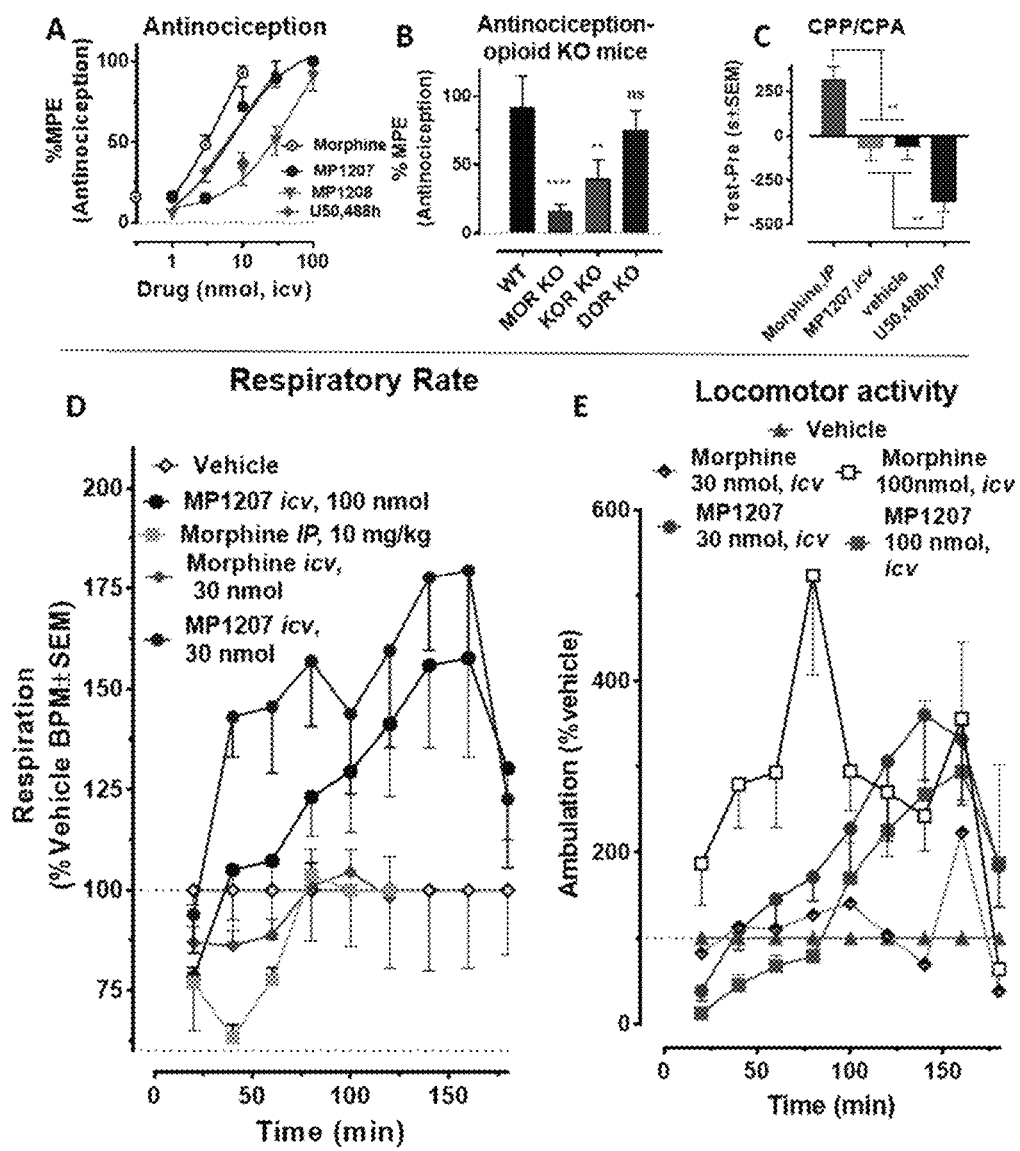
FIGS. 12A-12E show analgesia and side effect profiles of the dual mu-kappa G-protein biased agonist MP1207.

The more potent compound MP1207 was characterized in detail, studying receptor selectivity and opioid receptor induced adverse effects. A genetic knock out (KO) mice lacking MOR, KOR or DOR were used to examine the selectivity of MP1267's analgesic actions (FIG. 12B). MP1207 antinociception was found to be significantly attenuated in both MOR KO and KOR KO but remained intact in DOR KO mice. The results were in line with the >40-fold selectivity of MOR and KOR over DOR in the binding assays for MP1207. Next, MP1207 was evaluated for side effects. MP1207 failed to show either rewarding or aversive behavior in a conditioned place preference paradigm at the highest solubility permitting dose tested (100 nmol, icv) in mice (FIG. 12C). Morphine and U50,488h as expected showed place preference and place aversion effects, respectively (FIG. 12C). The dose of MP1207 for side effects testing was 16 times higher than the analgesic ED$_{50}$ dose (6.1 nmol, icv).

Next, MP1207 was tested for its effect on respiratory rate. As expected, morphine when administered icv or IP decreased respiratory rate. In contrast, MP1207 at 30 nmol (5×ED$_{50}$ dose) stimulated respiration (FIG. 12D). At a higher dose of 100 nmol icv, MP1207 still stimulated respiration, although the stimulation observed was lower than seen at the lower dose of 30 nmol. Finally, locomotor activity was examined in the same mice. In WT mice, MP1207 stimulated locomotor activity at the lower dose of 30 nmol (icv) compared to 100 nmol (icv). (FIG. 12E). Together, these results support earlier suggestions that dual MOR and KOR agonism may offset the liabilities of receptor-selective agonists.

Figure 13:
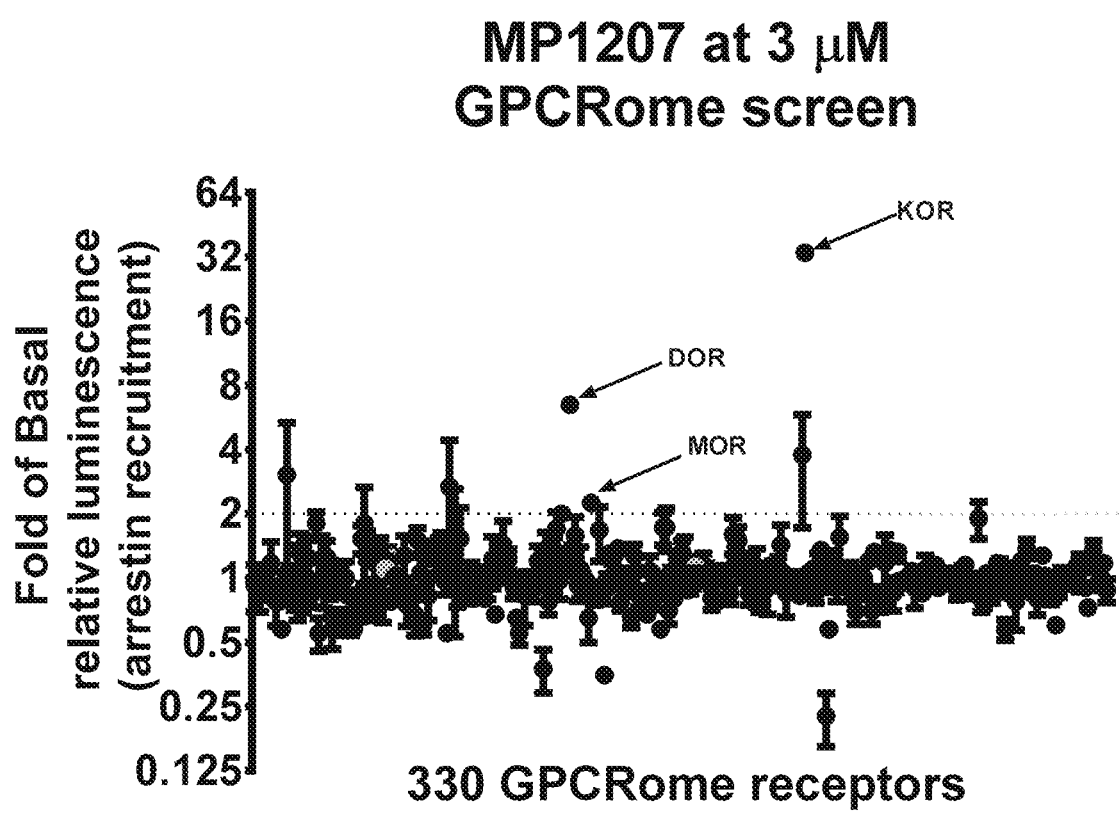
FIG. 13 shows MP1207 is selective for opioid receptors in the GPCRome screen. MP1207 was screened against 330 non-olfactory GPCRs for agonism in the arrestin recruitment TANGO assay. Each point shows luminescence normalized to basal level at a given GPCR at 3 µM MP1207 dose (>3000 higher dose than the binding affinity at opioid receptors), with vertical lines indicating the standard error of the mean. MP1207 induces an increase in signal 2-fold over basal at opioid receptors predominantly at KOR and DOR and much less at MOR. Results show selectivity for opioid receptors over non-opioid targets when tested at >10,000 and >1500 fold higher than the binding affinity and agonistic potency at opioid receptors. The low signal at MOR is consistent with null arrestin recruitment at MOR.

Overall, these results demonstrate that MP1207 produces potent antinociception predominantly mediated by KOR and MOR, yet shows a separation of analgesia from some classic opioid side effects such as respiratory depression, conditioned place preference, and aversion, in contrast with the canonical mu and kappa-selective agonists, morphine and U50,488h. MP1207 also showed reasonable selectivity for opioid receptors over 330 GPCRs in the in vitro screen for off-target activity (FIG. 13) suggesting an on target opioid mediated effect for this probe.

H. Discussion

This disclosure employs a new structure-based concept for controlling ligand functional profile to design dual MOR and KOR G-protein biased agonists, which show efficient analgesia in vivo, but lack the respiratory depression and aversion/reward liabilities of classical opioid analgesics. Over the last ~15 years, the discovery of G-protein biased opioids ligands has been widely considered as a strategy for the development of potent but safer opioid analgesics. With recent setbacks for the TRV130 clinical approval and mixed results on the ability of MOR-specific G-protein biased ligands to alleviate opioid side effects (Kliewer et al., 2019; Hill et al., 2018), it is clear that ligands with more precisely tuned selectivity and functional profiles are needed to more definitively interrogate the pharmacological mechanisms for insulating opioid analgesia from their notorious side effects. Using recently solved active-state structure of KOR in complex with MP1104 and computational modeling studies of close analogs MP1202 and IBNtxA, two sites in the binding pockets of both MOR and KOR were identified: (1) a primarily hydrophobic sub-pocket between TM2-TM3, and (2) a region between TM5-ECL2 lined with acidic residues. The data show that boat or chair conformations of ring C in the MP1104 scaffold can control the switch of the rigid amidophenyl arm between these two sites. Most importantly, the predicted interactions of the amidophenyl arm in the TM2-TM3 sub-pocket correlated with balanced recruitment of G-protein and β-arrestin2, while the switch to the TM5-ECL2 site correlated with G-protein biased agonism in the opioid receptors. To test the applicability of this observation, MP1207 and MP1208 were designed with basic moieties that are predicted to facilitate interactions with acidic residues in TM5-ECL2. While the ligands retained high affinity binding and G-protein mediated signaling, they showed dramatically reduced arrestin recruitment at both MOR and KOR, thus providing support for the design strategy for G-protein biased agonists. The D223A/E209A double mutation in the TM5-ECL2 site of KOR eliminated bias along with other MP1207 analogs (MP1209/1210-polar and charged) which did not engage this region further corroborating the role of that region in the biased signaling of MP1207/08.

Interestingly, the TM5-ECL2 role in bias is also in line with the docking pose for a known biased kappa ligand 6'GNTI which has its guanidine group align within the TM5-ECL2 region similar to the amidophenyl arm of the compounds. The TM5-ECL2 region has also been proposed as a region dictating bias at other GPCRs such as $5HT_{2B}$ serotonin (McCorvy et al., 2018) and $D_2$ dopamine (Chun et al., 2018) receptors although the specific mechanisms may differ between these receptors.

Interpretation of bias analysis in vitro has its limitations, as discussed recently (Luttrell et al., 2015; Gundry et al., 2017). For most compounds, lack of measurable arrestin signal in one assay (e.g. BRET) usually was corroborated by strong G-protein bias measured with another assay (e.g. Tango or in different species). For some others, the absence of measurable arrestin recruitment precluded calculation of bias factor in both the BRET and Tango assays. In these cases, a lower efficacy partial agonism at G-protein cannot be ruled out as at least partially responsible for low arrestin recruitment or drop in arrestin signal.

When evaluated in animal models MP1207 demonstrated supraspinal analgesia mediated by MOR and KOR while showing attenuated abuse potential and aversion, as well as lack of respiratory depression. Surprisingly, in contrast to the conventional respiratory depression characteristic of MOR-selective agonists, a modest stimulation was observed which was mediated by KOR activation, as shown by testing in KOR knockout mice. The present data are consistent with evidence suggesting that mixed activation of MOR and KOR may produce potent analgesia with reduced liabilities. For instance, a report examining co-administration of nalfurafine with oxycodone noted reduction of both self-administration as well as respiratory depression, suggesting that mixed mu/kappa ligands (Townsend et al., 2017) may have a superior safety profile over either classical or biased ligands at a single subtype. Admittedly, the role of dual MOR/KOR G-protein bias in diminished respiratory depression is preliminary, with a full dose characterization and alternative interpretations such as partial agonism at the opioid receptors regulating respiration remain to be tested. However, U50,488h sc and icv have been not only shown to lack respiratory depression on their own (Matthes et al, 1998) but were reported to reduce DAMGO-induced respiratory depression (Dosaka-Akita et al., 1993), similar to the action ascribed presently to MP1207, supporting a potential role of KOR in alleviating respiratory depression.

Example 3—Methods

Radioligand Competition Binding Assays. [$^{125}$I]IBNtxA binding was carried out in membranes prepared from Chinese Hamster Ovary (CHO) cells stably expressing murine clones of mMOR, mDOR, and mKOR, as previously described (Varadi et al., 2015; Pickett et al., 2015; Varadi et al., 2013). In brief, binding was performed at 25° C. for 90 min. Binding in mMOR/CHO was carried out in 50 mM potassium phosphate buffer with 5 mM $MgSO_4$ and 20 µg/mL protein while binding in mKOR/CHO and mDOR/CHO was carried out in 50 mM potassium phosphate pH=7.0 buffer and 40 µg/mL protein. After the incubation, the reaction was filtered through glass-fiber filters (Whatman Schleicher & Schuell, Keene, N. H.) and washed (3×3 mL of ice-cold 50 mM Tris-HCl, pH 7.4) on a semiautomatic cell harvester. Nonspecific binding was determined by the addition of levallorphan (8 µM) to matching samples and was subtracted from total binding to yield specific binding. Protein concentrations were determined using the Lowry method with BSA as the standard (Lowry et al., 1951). K values were calculated by nonlinear regression analysis in GraphPad Prism.

[$^{35}$S]GTPγS Functional Assay. [$^{35}$S]GTPγS binding was performed on membranes prepared from transfected cells stably expressing opioid receptors in the presence and absence of the indicated compound for 60 min at 30° C. in the assay buffer (50 mM Tris-HCl, pH 7.4, 3 mM $MgCl_2$, 0.2 mM EGTA, and 10 mM NaCl) containing 0.05 nM [$^{35}$S] GTPγS; 2 µg/mL each leupeptin, pepstatin, aprotinin, and bestatin; and 30 µM GDP, as previously described (Bolan et al., 2014). After the incubation, the reactions were filtered through glass fiber filters (Whatman Schleicher & Schuell, Keene, N. H.) and washed (3×3 mL of ice-cold buffer, 50 mM Tris-HCl, pH 7.4) on a semi-automatic cell harvester. Filters were transferred into vials with 3 mL of Liquiscint (National Diagnostics, Atlanta, Ga.), and the radioactivity in vials was determined by scintillation spectroscopy in a Tri-Carb 2900TR counter (PerkinElmer Life and Analytical Sciences). Basal binding was determined in the presence of GDP and the absence of drug. Data was normalized to 100 nM DAMGO, DPDPE, and U50,488h for mMOR, mDOR, and mKOR binding, respectively. $EC_{50}$, $IC_{50}$, and % $E_{max}$ values were calculated by nonlinear regression analysis in GraphPad Prism.

cAMP Inhibition Assay. To measure $G_{\alpha i}$-mediated cAMP inhibition, HEK 293T (ATCC CRL-11268) cells were co-transfected with human opioid receptor (hMOR/hKOR/hDOR) along with a luciferase-based cAMP biosensor (GloSensor; Promega) and assays were performed similar to previously described (Che et al., 2018; Fenalti et al., 2014). After 16 h, transfected cells were plated into Poly-lysine coated 384-well white clear bottom cell culture plates in DMEM with 1% dialyzed FBS at a density of 15,000-20,000 cells per 40 µL per well and incubated at 37° C. with 5% $CO_2$ overnight. Next day, drug solutions were prepared in freshly prepared buffer [20 mM HEPES, 1×HBSS, 0.3% bovine serum album (BSA), pH 7.4] at 3× drug concentration. Plates were decanted and received 20 µL per well of drug buffer (20 mM HEPES, lx HBSS, pH 7.4) followed by addition of 10 µL of drug solution (3 wells per condition) for 15 min in the dark at room temperature. To stimulate endogenous cAMP via β adrenergic-Gs activation, 10 µL luciferin (4 mM, final concentration) supplemented with isoproterenol (400 nM, final concentration) were added per well. Cells were incubated in the dark at room temperature for 15 min, and luminescence intensity was quantified using a Wallac TriLux Microbeta (Perkin Elmer) luminescence counter. Results (relative luminescence units) were plotted as a function of drug concentration, normalized to $E_{max}$ of DAMGO and U50,488h for MOR and KOR respectively; and analyzed using "log(agonist) vs. response" in GraphPad Prism.

Tango β-arrestin Recruitment Assay. The Tango assays were performed as previously described (Che et al., 2018). HTLA cells expressing TEV fused-β-Arrestin2 were transfected with human opioid receptors (hMOR/hKOR/hDOR) Tango construct. The next day, cells were plated in DMEM supplemented with dialyzed FBS (1%) in poly-L-lysine coated 384-well white clear bottom cell culture plates at a density of 10,000-15,000 cells/well in a total of 40 µL. The cells were incubated for at least 6 h before receiving drug stimulation. Drug solutions were prepared in drug buffer (20 mM HEPES, lx HESS, 0.3% ESA, pH 7.4) at 3× and added to cells (20 µL per well) for overnight incubation. The same drug solutions were used for the Tango and cAMP assays. The next day, media and drug solutions were removed and 20 µL per well of BrightGlo reagent (Promega, with 1:20 dilution) was added. The plate was incubated for 20 min at room temperature in the dark before counting using a luminescence counter. Results (relative luminescence units) were plotted as a function of drug concentration, normalized to $E_{max}$ of DAMGO and U50,488h for hMOR and hKOR respectively, and analyzed using "log(agonist) vs. response" in GraphPad Prism.

Bioluminescence Resonance Energy Transfer (BRET) Assay. The BRET assays were performed by following the protocol published previously (Kruegel et al., 2016). In brief, the following cDNA amounts were transfected into HEK-293T cells ($5 \times 10^6$ cells/plate) in 10-cm dishes using polyethylenimine (PEI) in a 1:1 ratio (diluted in Opti-MEM, Life Technologies): for G protein activation; 2.5 μg mMOR/mKOR/mDOR, 0.125 μg GaoBRLuc8, 6.25 μg (5 μg $β_1$, 6.25 μg mVenus-γ2; for arrestin recruitment; 2 μg mMOR/mKOR/mDOR, 0.25 μg Rluc8- arrestin3-Sp1, 5 μg mem-linker-citrine-SH3, 5 μg GRK2. Cells were maintained in HEKS44 293T media described above. The media was changed after 24 h of the transfection and cells were dissociated and re-suspended in phosphate buffered saline (PBS) at 48 h of transfection. Approximately 200,000 cells/well were added to a black-framed, white well 96-well plate (Perkin Elmer; Waltham, Mass.). The microplate was centrifuged, and the cells were resuspended in PBS. For agonist experiments, after 5 min, 5 μM of the luciferase substrate coelenterazine H was added to each well. After 5 min, ligands were added, and the BRET signal was measured 5 min later using PHERAstar FS plate reader. For antagonist competition experiments, cells were pre-incubated with the antagonist at varying concentration for 30 min. Coelenterazine H (5 μM) was then added to each well for 5 min. Following coelenterazine H incubation, a fixed concentration of the reference agonist (5× $EC_{50}$) was added, and the BRET signal was measured at 30 min using PHERAstar FS plate reader. The signal was quantified by calculating the ratio of the light emitted by the energy acceptor, mVenus (510-540 nm) or citrine (510-540 nm), over the light emitted by the energy donor, RLuc8 (485 nm). This drug-induced BRET signal was normalized to $E_{max}$ of DAMGO or U50, 488h at MOR and KOR respectively. Dose response curves were fit using a three-parameter logistic equation in GraphPad Prism.

Assessment of off-target activity of MP1207 using PRESTO-Tango GPCR-ome To identify potential off-target activity of MP1207, the National Institutes of Mental Health Psychoactive Drug Screen Program were used. MP1207 was first tested for activity against 330 non-olfactory GPCRs using the PRESTO-Tango GPCRome screening β-arrestin recruitment assay at 3 μM MP1207. The activity at each receptor was measured in quadruplicate.

Screening of compounds was accomplished using previously described methods with several modifications (www.ncbi.nlm.nih.gov/pmc/articles/PMC4424118/). First, HTLA cells were plated in DMEM with 2% dialyzed FBS and 10 U/mL penicillin-streptomycin. Next, the cells were transfected using an in-plate PEI method (www.ncbi.nlm.nih.gov/pmc/articles/PMC4012321/). PRESTO-Tango receptor DNAs were resuspended in OptiMEM and hybridized with PEI prior to dilution and distribution into 384-well plates and subsequent addition to cells. After overnight incubation, drugs diluted in DMEM with 1% dialyzed FBS were added to cells without replacement of the medium. The remaining steps of the PRESTO-Tango protocol were followed as previously described.

Tail-withdrawal assay The 55° C. warm-water tail-withdrawal assay was conducted in mice as a measure of acute thermal antinociception as described previously (Reilley et al., 2010). Briefly, each mouse was tested for baseline tail-withdrawal latency prior to drug administration. Following drug administration, the latency for each mouse to withdraw the tail was measured every 10 minutes until latency returned to the baseline value. A maximum response time of 15 seconds was utilized to prevent tissue damage. If the mouse failed to display a tail-withdrawal response within 15 seconds, the tail was removed from the water and the animal was assigned a maximal antinociceptive score of 100%. Data are reported as percent antinociception, calculated by the equation: % antinociception=100×[(test latency−baseline latency)/(15−baseline latency)]. This was utilized to account for innate variability between mice. Compounds were administered either, interpretationally (IP) or intracerebroventricular (icv) and the analgesic action of compounds was assessed at the peak effect as described previously (Haley and McCormick, 1957). In brief, mice were anesthetized using isoflurane. A small incision was made, and the drug (2 μl/mouse) was injected (using a 10 μL Hamilton syringe fitted to a 27-gauge needle) into the right lateral ventricle at the following coordinates: 2 mm caudal to bregma, 2 mm lateral to sagittal suture, and 2 mm in depth. Mice were tested for analgesia at the peak effect post injection.

Respiratory and Locomotor Effects. Respiration rates and spontaneous ambulation rates were monitored using the automated, computer-controlled Comprehensive Lab Animal Monitoring System (CLAMS, Columbus Instruments, Columbus, Ohio) as described previously (Reilley et al., 2010; Cirino et al., 2019). Awake, freely moving adult male mice (C57 WT, MOR KO, and KOR KO) were habituated in closed, sealed individual apparatus cages (23.5 cm×11/5 cm×13 cm) for 60 min before testing. A baseline for each animal was obtained over the 60-min period before drug injection, and testing began immediately post-injection. Vehicle, morphine (10 mg/kg, IP or 30 or 100 nmol, icv), or MP1207 (30 or 100 nmol, icv) were administered (i.c.v.) and five min later mice were confined to the CLAMS testing cages for 200 min. Using a pressure transducer built into the sealed CLAMS cage, the respiration rate (breaths/min) of each occupant mouse was measured. Infrared beams located in the floor measured locomotion as ambulations, from the number of sequential breaks of adjacent beams. Data are expressed as percent of vehicle control response.

Conditioned Place Preference and Aversion. Mice were conditioned with a counterbalanced place conditioning paradigm using similar timing as detailed previously (Varadi et al., 2016). Groups of C57BL/6J mice (n=18-24) freely explored a three-compartment apparatus for 30 min. The amount of time subjects spent in each compartment was measured over the 30 min testing period. Prior to place conditioning, the animals did not demonstrate significant differences in their time spent exploring the left vs right compartments. During each of the next 2 days, mice were administered vehicle (0.9% saline) and consistently confined in a randomly assigned outer compartment for 40 min, half of each group in the right chamber, half in the left chamber. Four hours later, mice were administered drugs morphine (10 mg/kg, IP), U50,488h (30 mg/kg, IP), MP1207 (100 nmol, icv) or vehicle and were placed to the opposite compartment for 40 min. Conditioned place preference or aversion data are presented as the difference in time spent in drug- and vehicle associated chambers.

Molecular Modeling. The receptor proteins were extracted from the RCSB server for mouse MOR (PDBID: 5clm), and human KOR (PDBID: 6b73), representing agonist-bound active state of the receptors. All the objects except the receptor protein subunit, the crystallized ligand, and three crystallographic waters important for ligand interactions were deleted from the MOR structure, and the protein was prepared by addition and optimization of hydrogens and optimization of the side chain residues. A similar procedure was also followed for the KOR structure, with an additional step of transplanting and optimizing the three crystallographic water molecules from the active state MOR into active state KOR. Ligands were sketched, assigned formal charges and energy-optimized prior to docking. The ligand docking box for potential grid docking was defined as the whole extracellular half of the protein, and all-atom docking was performed using the energy minimized structures for all ligands with a thoroughness value of 30. The best-scored docking poses, for both chair and boat forms, were further optimized by several rounds of minimization and Monte Carlo sampling of the ligand conformation, including the surrounding side-chain residues (within 5 A° of the ligand) and the three crystallographic water molecules in the orthosteric sites. All the above molecular modeling operations were performed in ICM-Pro v3.8-5 molecular modeling package. The DFT (B3LYP) QM calculations for boat and chair conformations of ligands were performed using Gaussian03 with two basis sets (LanL2DZ and DGDZVP) using the servers at the High-Performance Computing at the University of Southern California.

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

IX. References

The following references, such that they provide exemplary procedural or other details supplementary to those set forth herein, are specifically incorporated by reference.

Aldrich et al., *Br. J. Pharmacol.*, 171:3212-3222, 2014.
Anderson, *Practical Process Research & Development—A Guide for Organic Chemists*, 2nd ed., Academic Press, New York, 2012.
Bohn et al. *Science* 286:2495-2498, 1999.
Bolan et al., *Synapse*, 51:11-18, 2004.
Bu et al, *Int J Neurosci* 125:56-65, 2015.
Che et al., *Cell*, 172:55-67.e15, 2018.
Chun et al., *Frontiers in Synaptic Neuroscience*, 10:2, 2018.
Cirino et al., *Front. Pharmacol.*, 10:678, 2019.
Crooks et al., *Bioorganic and Medicinal Chemistry Letters* 16:4291-4295, 2006.
Crowley et al, *Journal of Medicinal Chemistry* 59:11027-11038, 2016.
Dewire et al., *J. Pharmacol. Exp. Ther.* 344:708-717, 2013.
Dosaka-Akita et al., *J. Pharmacol. Exp. Ther.*, 264:631-637, 1993.
Penalti et al., *Nature*, 506:191-196, 2014.
Grinnell et al., *Synapse* 70:395-407, 2016.
Gundry et al., *Front. Neurosci.*, 11:17, 2017.
Haley and McCormick, *Br. J. Pharmacol.*, 12:12-15, 1957.
*Handbook of Pharmaceutical Salts: Properties, and Use*, Stahl and Wermuth Eds., Verlag Helvetica Chimica Acta, 2002.
Harding et al., *J. Med. Chem* 48:4765-4771, 2005.
Hill et al., *Br. J. Pharmacol.*, 175:2653-2661, 2018.
Huang et al., *Nature*, 524:315-321, 2014.
Hupp & Neumeyer, *Tetrahedron Lett.* 51:2359-2361, 2010.
Jiang et al, *Journal of Medicinal Chemistry* 20:1100-1102, 1977.
Kenakin et al., *ACS Chem. Neuroscience*, 3:193-203, 2012.
Kliewer et al., *Nature Communications*, 10:367, 2019.
Kobylecki et al, *Journal of Medicinal Chemistry* 25:116-120, 1982.
Kruegel et al., *Journal of the American Chemical Society* 138:6754-6764, 2016.
Li et al., *International journal of molecular sciences* 10:954-963. 2009.
Lowry et al., *J. Biol. Chem.*, 193:265-275, 1951.
Luttrell et al., *Mol. Pharmacol.*, 88:579-588, 2015.
Majumdar et al., *Bioorg Med Chem Lett* 21:4001-4, 2011.
Majumdar et al., *Proc. Natl. Acad Sci., USA*, 108:19778-19783, 2011.
Manglik et al., *Nature* 537:185-190, 2016.
Matthes et al., *J. Neuroscience*, 18:7285-7295, 1998.
McCorvy et al., *Nature Chem. Biol.*, 14:126-134, 2018.
Nagase et al, *A New Useful Conversion Method of Naltrexone to 14-Deoxynaltrexone*, 2006.
Pickett et al., *Bioorg. Med. Chem. Lett.*, 25:1761-1764, 2015
Raehal et al., *J. Pharmacol. Exp. Ther.* 314:1195-1201, 2005.
Rankovic et al, *Bioorganic & Medicinal Chemistry Letters* 26:241-250, 2016.
Reagan-Shaw et al, *FASEB J.*, 22(3):659-661, 2008.
Reilley et al, *AAPS J.*, 12:318-329, 2010.
Rives et al, *J. Biol. Chem.*, 287:27050-27054, 2012.
Robinson & Roskamp, *Tetrahedron* 53:6697-6705, 1997.
Schmid et al., *J. Biol. Chem.*, 288:22387-22398, 2013.
Schmid et al., *Cell* 171:1165-1175.el 113, 2017.
Simon et al., *Tetrahedron* 50:9757-9768, 1994.
Simon et al, *Synthetic Communications* 22, 913-921, 1992.
Smith, *March's Advanced Organic Chemistry: Reactions, Mechanisms, and Structure*, 7th Ed, Wiley 2013.
Tins & Kerr, *Journal of the American Chemical Society* 114:5959-5966, 1992.
Townsend et al, *Psychopharmacology*, 234:2597-2605, 2017.
Varadi et al., *J Med Chem* 59:8381-8397, 2016.
Varadi et al., *European J. Med. Chem.*, 69:786-789, 2013.
Varadi et al, *ACS Chemical Neuroscience* 6:1813-1824, 2015.
Varadi et al, *ACS Chemical Neuroscience* 6:1570-1577, 2015.
Yuan et al, *J Med Chem* 56:9156-69, 2013.
Zhang et al., *RSC Advances* 4:40444-40448, 2014.
Zhang et al., *Journal of Medicinal Chemistry* 50:2747-2751, 2007.
Zhang et al, *J. Med. Chem.* 50:2747-2751, 2007.

What is claimed is:
1. A compound of the formula:

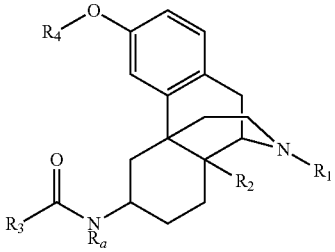

(I)

wherein:
R$_1$ is alkyl$_{(c≤8)}$, cycloalkyl$_{(c≤8)}$, alkenyl$_{(c≤8)}$, or —Y$_1$—R$_1$', wherein:
Y$_1$ is alkanediyl$_{(c≤8)}$ or substituted alkanediyl$_{(c≤8)}$; and
R$_1$' is cycloalkyl$_{(c≤8)}$, aryl$_{(c≤12)}$, or a substituted version of either of these groups;
R$_2$ is hydrogen, hydroxy, alkoxy$_{(c≤8)}$, alkenyloxy$_{(c≤8)}$, aryloxy$_{(c≤8)}$, aralkoxy$_{(c≤8)}$, acyloxy$_{(c≤8)}$, or a substituted version of any of the last five groups;
R$_a$ is hydrogen;
R$_3$ is a group of the formula:

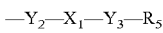

wherein:
Y$_2$ is a covalent bond;
X$_1$ is arenediyl$_{(c≤12)}$, heteroarenediyl$_{(c≤12)}$, or a substituted version of either group; and
Y$_3$ is alkanediyl$_{(c≤8)}$ or substituted alkanediyl$_{(c≤8)}$;
R$_5$ is hydroxy, amino, alkylamino$_{(c≤8)}$, substituted alkylamino$_{(c≤8)}$, dialkylamino$_{(c≤12)}$, substituted dialkylamino$_{(c≤12)}$, or —NR$_c$C(NR$_d$)R$_5$', wherein:
R$_c$ and R$_d$ are each independently hydrogen, alkyl$_{(c≤6)}$, or substituted alkyl$_{(c≤6)}$;
R$_5$' is amino, alkylamino$_{(c≤8)}$, substituted alkylamino$_{(c≤8)}$, dialkylamino$_{(c≤12)}$, or substituted dialkylamino$_{(c≤12)}$;
R$_4$ is hydrogen, alkyl$_{(c≤6)}$, substituted alkyl$_{(c≤6)}$, acyl$_{(c≤6)}$, or substituted acyl$_{(c≤6)}$; or
a compound of the formula:

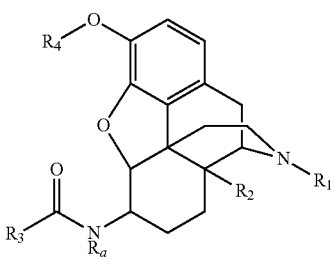

(II)

wherein:
R$_1$ is alkyl$_{(c≤8)}$, cycloalkyl$_{(c≤8)}$, alkenyl$_{(c≤8)}$, or —Y$_1$—R$_1$', wherein:
Y$_1$ is alkanediyl$_{(c≤8)}$ or substituted alkanediyl$_{(c≤8)}$; and
R$_1$' is cycloalkyl$_{(c≤8)}$, aryl$_{(c≤12)}$, or a substituted version of either of these groups;

R$_2$ is hydrogen, hydroxy, alkoxy$_{(c≤8)}$, alkenyloxy$_{(c≤8)}$, aryloxy$_{(c≤8)}$, aralkoxy$_{(c≤8)}$, acyloxy$_{(c≤8)}$, or a substituted version of any of the last five groups;
R$_a$ is hydrogen;
R$_3$ is a group of the formula:

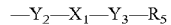

wherein:
Y$_2$ is a covalent bond;
X$_1$ is arenediyl$_{(c≤12)}$, heteroarenediyl$_{(c≤12)}$, or a substituted version of either group; and
Y$_3$ is alkanediyl$_{(c≤8)}$ or substituted alkanediyl$_{(c≤8)}$;
R$_5$ is hydroxy, amino, alkylamino$_{(c≤8)}$, substituted alkylamino$_{(c≤8)}$, dialkylamino$_{(c≤12)}$, substituted dialkylamino$_{(c≤12)}$, or —NR$_c$C(NR$_d$)R$_5$', wherein:
R$_c$ and R$_d$ are each independently hydrogen, alkyl$_{(c≤6)}$, or substituted alkyl$_{(c≤6)}$;
R$_5$' is amino, alkylamino$_{(c≤8)}$, substituted alkylamino$_{(c≤8)}$, dialkylamino$_{(c≤12)}$, or substituted dialkylamino$_{(c≤12)}$; and
R$_4$ is hydrogen, alkyl$_{(c≤6)}$, substituted alkyl$_{(c≤6)}$, acyl$_{(c≤6)}$, or substituted acyl$_{(c≤6)}$;
provided either R$_2$ is not hydroxy or R$_5$ is amino, alkylamino$_{(c≤8)}$, substituted alkylamino$_{(c≤8)}$, dialkylamino$_{(c≤12)}$, substituted dialkylamino$_{(c≤12)}$, or —NR$_c$C(NR$_d$)R$_5$';
or a pharmaceutically acceptable salt thereof.

2. The compound of claim 1 further defined as:

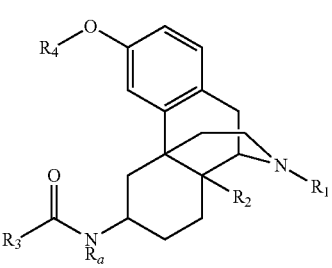

(I)

wherein:
R$_1$ is alkyl$_{(c≤8)}$, cycloalkyl$_{(c≤8)}$, alkenyl$_{(c≤8)}$, or —Y$_1$—R$_1$', wherein:
Y$_1$ is alkanediyl$_{(c≤8)}$ or substituted alkanediyl$_{(c≤8)}$; and
R$_1$' is cycloalkyl$_{(c≤8)}$, aryl$_{(c≤12)}$, or a substituted version of either of these groups;
R$_2$ is hydrogen, hydroxy, alkoxy$_{(c≤8)}$, alkenyloxy$_{(c≤8)}$, aryloxy$_{(c≤8)}$, aralkoxy$_{(c≤8)}$, acyloxy$_{(c≤8)}$, or a substituted version of any of the last five groups;
R$_a$ is hydrogen;
R$_3$ is a group of the formula:

wherein:
Y$_2$ is a covalent bond;
X$_1$ is arenediyl$_{(c≤12)}$, heteroarenediyl$_{(c≤12)}$, or a substituted version of either group; and
Y$_3$ is alkanediyl$_{(c≤8)}$ or substituted alkanediyl$_{(c≤8)}$;
R$_5$ is hydroxy, amino, alkylamino$_{(c≤8)}$, substituted alkylamino$_{(c≤8)}$, dialkylamino$_{(c≤12)}$, substituted dialkylamino$_{(c≤12)}$, or —NR$_c$C(NR$_d$)R$_5$', wherein:
R$_c$ and R$_d$ are each independently hydrogen, alkyl$_{(c≤6)}$, or substituted alkyl$_{(c≤6)}$;

$R_5'$ is amino, alkylamino$_{(c\leq8)}$, substituted alkylamino$_{(c\leq8)}$, dialkylamino$_{(c\leq12)}$, or substituted dialkylamino$_{(c\leq12)}$; and $R_4$ is hydrogen, alkyl$_{(c\leq6)}$, substituted alkyl$_{(c\leq6)}$, acyl$_{(c\leq6)}$, or substituted acyl$_{(c\leq6)}$;

or a pharmaceutically acceptable salt thereof.

3. The compound of claim 1 further defined as:

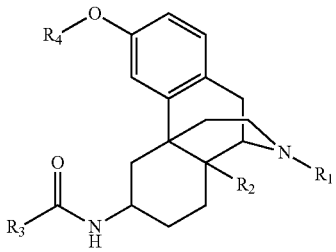

(III)

wherein:

$R_1$ is alkyl$_{(c\leq8)}$, cycloalkyl$_{(c\leq8)}$, alkenyl$_{(c\leq8)}$, or —Y$_1$—R$_1$', wherein:

$Y_1$ is alkanediyl$_{(c\leq8)}$ or substituted alkanediyl$_{(c\leq8)}$; and $R_1'$ is cycloalkyl$_{(c\leq8)}$, aryl$_{(c\leq12)}$, or a substituted version of either of these groups;

$R_2$ is hydrogen, hydroxy, alkoxy$_{(c\leq8)}$, alkenyloxy$_{(c\leq8)}$, aryloxy$_{(c\leq8)}$, aralkoxy$_{(c\leq8)}$, acyloxy$_{(c\leq8)}$, or a substituted version of any of the last five groups;

$R_3$ is a group of the formula:

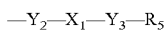

—Y$_2$—X$_1$—Y$_3$—R$_5$ wherein:

$Y_2$ is a covalent bond;

$X_1$ is arenediyl$_{(c\leq12)}$, heteroarenediyl$_{(c\leq12)}$, or a substituted version of either group; and $Y_3$ is alkanediyl$_{(c\leq8)}$, or substituted alkanediyl$_{(c\leq8)}$;

$R_5$ is hydroxy, amino, alkylamino$_{(c\leq8)}$, substituted alkylamino$_{(c\leq8)}$, dialkylamino$_{(c\leq12)}$, substituted dialkylamino$_{(c\leq12)}$, or —NR$_c$C(NR$_d$)R$_5'$, wherein:

$R_c$ and $R_d$ are each independently hydrogen, alkyl$_{(c\leq6)}$, or substituted alkyl$_{(c\leq6)}$;

$R_5'$ is amino, alkylamino$_{(c\leq8)}$, substituted alkylamino$_{(c\leq8)}$, dialkylamino$_{(c\leq12)}$, or substituted dialkylamino$_{(c\leq12)}$; and $R_4$ is hydrogen, alkyl$_{(c\leq6)}$, substituted alkyl$_{(c\leq6)}$, acyl$_{(c\leq6)}$, or substituted acyl$_{(c\leq6)}$;

or a pharmaceutically acceptable salt thereof.

4. The compound of claim 1 further defined as:

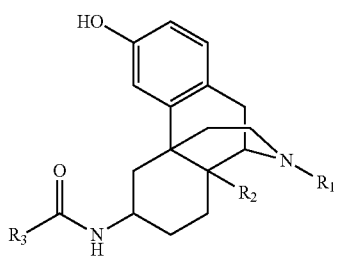

(IV)

wherein:

$R_1$ is alkyl$_{(c\leq8)}$, cycloalkyl$_{(c\leq8)}$, alkenyl$_{(c\leq8)}$, or —Y$_1$—R$_1$', wherein:

$Y_1$ is alkanediyl$_{(c\leq8)}$ or substituted alkanediyl$_{(c\leq8)}$; and $R_1'$ is cycloalkyl$_{(c\leq8)}$, aryl$_{(c\leq12)}$, or a substituted version of either of these groups;

$R_2$ is hydrogen, hydroxy, alkoxy$_{(c\leq8)}$, alkenyloxy$_{(c\leq8)}$, aryloxy$_{(c\leq8)}$, aralkoxy$_{(c\leq8)}$, acyloxy$_{(c\leq8)}$, or a substituted version of any of the last five groups; and $R_3$ is a group of the formula:

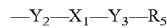

—Y$_2$—X$_1$—Y$_3$—R$_5$ wherein:

$Y_2$ is a covalent bond;

$X_1$ is arenediyl$_{(c\leq12)}$, heteroarenediyl$_{(c\leq12)}$, or a substituted version of either group; and $Y_3$ is alkanediyl$_{(c\leq8)}$ or substituted alkanediyl$_{(c\leq8)}$;

$R_5$ is hydroxy, amino, alkylamino$_{(c\leq8)}$, substituted alkylamino$_{(c\leq8)}$, dialkylamino$_{(c\leq12)}$, substituted dialkylamino$_{(c\leq12)}$, or —NR$_c$C(NR$_d$)R$_5'$, wherein:

$R_c$ and $R_d$ are each independently hydrogen, alkyl$_{(c\leq6)}$, or substituted alkyl$_{(c\leq6)}$;

$R_5'$ is amino, alkylamino$_{(c\leq8)}$, substituted alkylamino$_{(c\leq8)}$, dialkylamino$_{(c\leq12)}$, or substituted dialkylamino$_{(c\leq12)}$;

or a pharmaceutically acceptable salt thereof.

5. The compound of claim 1 further defined as:

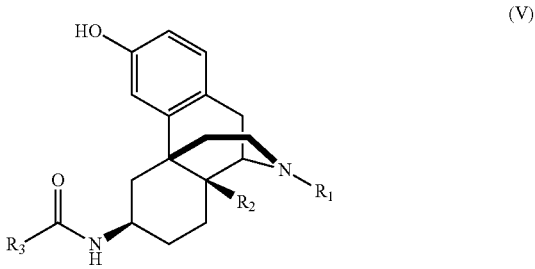

(V)

wherein:

$R_1$ is alkyl$_{(c\leq8)}$, cycloalkyl$_{(c\leq8)}$, alkenyl$_{(c\leq8)}$, or —Y$_1$—R$_1$', wherein:

$Y_1$ is alkanediyl$_{(c\leq8)}$ or substituted alkanediyl$_{(c\leq8)}$; and $R_1'$ is cycloalkyl$_{(c\leq8)}$, aryl$_{(c\leq12)}$, or a substituted version of either of these groups;

$R_2$ is hydrogen, hydroxy, alkoxy$_{(c\leq8)}$, alkenyloxy$_{(c\leq8)}$, aryloxy$_{(c\leq8)}$, aralkoxy$_{(c\leq8)}$, acyloxy$_{(c\leq8)}$, or a substituted version of any of the last five groups; and $R_3$ is a group of the formula:

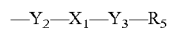

—Y$_2$—X$_1$—Y$_3$—R$_5$ wherein:

$Y_2$ is a covalent bond;

$X_1$ is arenediyl$_{(c\leq12)}$, heteroarenediyl$_{(c\leq12)}$, or a substituted version of either group; and $Y_3$ is alkanediyl$_{(c\leq8)}$ or substituted alkanediyl$_{(c\leq8)}$;

$R_5$ is hydroxy, amino, alkylamino$_{(c\leq8)}$, substituted alkylamino$_{(c\leq8)}$, dialkylamino$_{(c\leq12)}$, substituted dialkylamino$_{(c\leq12)}$, or —NR$_c$C(NR$_d$)R$_5'$, wherein:

$R_c$ and $R_d$ are each independently hydrogen, alkyl$_{(c\leq6)}$, or substituted alkyl$_{(c\leq6)}$;

$R_5'$ is amino, alkylamino$_{(c\leq8)}$, substituted alkylamino$_{(c\leq8)}$, dialkylamino$_{(c\leq12)}$, or substituted dialkylamino$_{(c\leq12)}$;

or a pharmaceutically acceptable salt thereof.

6. The compound of claim 1 further defined as:

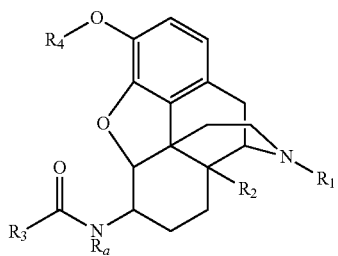

(II)

wherein:
R$_1$ is alkyl$_{(c≤8)}$, cycloalkyl$_{(c≤8)}$, alkenyl$_{(c≤8)}$, or —Y$_1$—R$_1$', wherein:
  Y$_1$ is alkanediyl$_{(c≤8)}$ or substituted alkanediyl$_{(c≤8)}$; and
  R$_1$' is cycloalkyl$_{(c≤8)}$, aryl$_{(c≤12)}$, or a substituted version of either of these groups;
R$_2$ is hydrogen, hydroxy, alkoxy$_{(c≤8)}$, alkenyloxy$_{(c≤8)}$, aryloxy$_{(c≤8)}$, aralkoxy$_{(c≤8)}$, acyloxy$_{(c≤8)}$, or a substituted version of any of the last five groups;
R$_a$ is hydrogen, alkyl$_{(c≤6)}$, or substituted alkyl$_{(c≤6)}$;
R$_3$ is a group of the formula:

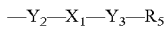
—Y$_2$—X$_1$—Y$_3$—R$_5$ wherein:
  Y$_2$ is a covalent bond;
  X$_1$ is arenediyl$_{(c≤12)}$, heteroarenediyl$_{(c≤12)}$, or a substituted version of either group; and
  Y$_3$ is alkanediyl$_{(c≤8)}$ or substituted alkanediyl$_{(c≤8)}$;
  R$_5$ is hydroxy, amino, alkylamino$_{(c≤8)}$, substituted alkylamino$_{(c≤8)}$, dialkylamino$_{(c≤12)}$, substituted dialkylamino$_{(c≤12)}$, or —NR$_c$C(NR$_d$)R$_5$', wherein:
    R$_c$ and R$_d$ are each independently hydrogen, alkyl$_{(c≤6)}$, or substituted alkyl$_{(c≤6)}$;
    R$_5$' is amino, alkylamino$_{(c≤8)}$, substituted alkylamino$_{(c≤8)}$, dialkylamino$_{(c≤12)}$, or substituted dialkylamino$_{(c≤12)}$; and
R$_4$ is hydrogen, alkyl$_{(c≤6)}$, substituted alkyl$_{(c≤6)}$, acyl$_{(c≤6)}$, or substituted acyl$_{(c≤6)}$;
provided either R$_2$ is not hydroxy or R$_5$ is amino, alkylamino$_{(c≤8)}$, substituted alkylamino$_{(c≤8)}$, dialkylamino$_{(c≤12)}$, substituted dialkylamino$_{(c≤12)}$, or —NR$_c$C(NR$_d$)R$_5$';
or a pharmaceutically acceptable salt thereof.

7. The compound of claim 1 further defined as:

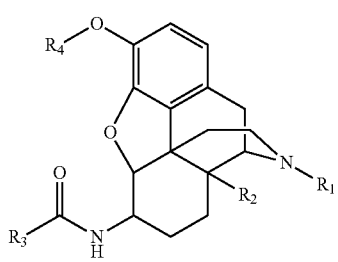

(VI)

wherein:
R$_1$ is alkyl$_{(c≤8)}$, cycloalkyl$_{(c≤8)}$, alkenyl$_{(c≤8)}$, or —Y$_1$—R$_1$', wherein:
  Y$_1$ is alkanediyl$_{(c≤8)}$ or substituted alkanediyl$_{(c≤8)}$; and
  R$_1$' is cycloalkyl$_{(c≤8)}$, aryl$_{(c≤12)}$, or a substituted version of either of these groups;
R$_2$ is hydrogen, hydroxy, alkoxy$_{(c≤8)}$, alkenyloxy$_{(c≤8)}$, aryloxy$_{(c≤8)}$, aralkoxy$_{(c≤8)}$, acyloxy$_{(c≤8)}$, or a substituted version of any of the last five groups;
R$_3$ is a group of the formula:

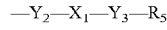
—Y$_2$—X$_1$—Y$_3$—R$_5$ wherein:
  Y$_2$ is a covalent bond;
  X$_1$ is arenediyl$_{(c≤12)}$, heteroarenediyl$_{(c≤12)}$, or a substituted version of either group; and
  Y$_3$ is alkanediyl$_{(c≤8)}$ or substituted alkanediyl$_{(c≤8)}$;
  R$_5$ is hydroxy, amino, alkylamino$_{(c≤8)}$, substituted alkylamino$_{(c≤8)}$, dialkylamino$_{(c≤12)}$, substituted dialkylamino$_{(c≤12)}$, or —NR$_c$C(NR$_d$)R$_5$', wherein:
    R$_c$ and R$_d$ are each independently hydrogen, alkyl$_{(c≤6)}$, or substituted alkyl$_{(c≤6)}$;
    R$_5$' is amino, alkylamino$_{(c≤8)}$, substituted alkylamino$_{(c≤8)}$, dialkylamino$_{(c≤12)}$, or substituted dialkylamino$_{(c≤12)}$; and
R$_4$ is hydrogen, alkyl$_{(c≤6)}$, substituted alkyl$_{(c≤6)}$, acyl$_{(c≤6)}$, or substituted acyl$_{(c≤6)}$;
provided R$_2$ is not hydroxy or R$_5$ is amino, alkylamino$_{(c≤8)}$, substituted alkylamino$_{(c≤8)}$, dialkylamino$_{(c≤12)}$, substituted dialkylamino$_{(c≤12)}$, or —NR$_c$C(NR$_d$)R$_5$';
or a pharmaceutically acceptable salt thereof.

8. The compound of claim 1 further defined as:

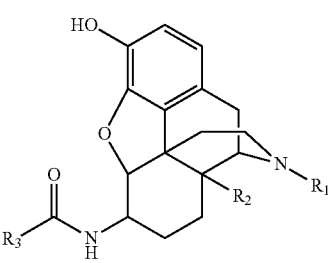

(VII)

wherein:
R$_1$ is alkyl$_{(c≤8)}$, cycloalkyl$_{(c≤8)}$, alkenyl$_{(c≤8)}$, or —Y$_1$—R$_1$', wherein:
  Y$_1$ is alkanediyl$_{(c≤8)}$ or substituted alkanediyl$_{(c≤8)}$; and
  R$_1$' is cycloalkyl$_{(c≤8)}$, aryl$_{(c≤12)}$, or a substituted version of either of these groups;
R$_2$ is hydrogen, hydroxy, alkoxy$_{(c≤8)}$, alkenyloxy$_{(c≤8)}$, aryloxy$_{(c≤8)}$, aralkoxy$_{(c≤8)}$, acyloxy$_{(c≤8)}$, or a substituted version of any of the last five groups; and
R$_3$ is a group of the formula:

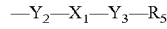
—Y$_2$—X$_1$—Y$_3$—R$_5$ wherein:
  Y$_2$ is a covalent bond;
  X$_1$ is arenediyl$_{(c≤12)}$, heteroarenediyl$_{(c≤12)}$, or a substituted version of either group; and
  Y$_3$ is alkanediyl$_{(c≤8)}$ or substituted alkanediyl$_{(c≤8)}$;
  R$_5$ is hydroxy, amino, alkylamino$_{(c≤8)}$, substituted alkylamino$_{(c≤8)}$, dialkylamino$_{(c≤12)}$, substituted dialkylamino$_{(c≤12)}$, or —NR$_c$C(NR$_d$)R$_5$', wherein:
    R$_c$ and R$_d$ are each independently hydrogen, alkyl$_{(c≤6)}$, or substituted alkyl$_{(c≤6)}$;

$R_5'$ is amino, alkylamino$_{(c≤8)}$, substituted alkylamino$_{(c≤8)}$, dialkylamino$_{(c≤12)}$, or substituted dialkylamino$_{(c≤12)}$;

provided $R_2$ is not hydroxy or $R_5$ is amino, alkylamino$_{(c≤8)}$, substituted alkylamino$_{(c≤8)}$, dialkylamino$_{(c≤12)}$, substituted dialkylamino$_{(c≤12)}$, or —NR$_c$C(NR$_d$)R$_5'$;

or a pharmaceutically acceptable salt thereof.

9. The compound of claim 1 further defined as:

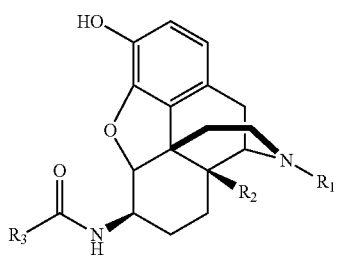

(VIII)

wherein:
$R_1$ is alkyl$_{(c≤8)}$, cycloalkyl$_{(c≤8)}$, alkenyl$_{(c≤8)}$, or —Y$_1$—R$_1'$, wherein:
  Y$_1$ is alkanediyl$_{(c≤8)}$ or substituted alkanediyl$_{(c≤8)}$; and
  R$_1'$ is cycloalkyl$_{(c≤8)}$, aryl$_{(c≤12)}$, or a substituted version of either of these groups;
$R_2$ is hydrogen, hydroxy, alkoxy$_{(c≤8)}$, alkenyloxy$_{(c≤8)}$, aryloxy$_{(c≤8)}$, aralkoxy$_{(c≤8)}$, acyloxy$_{(c≤8)}$, or a substituted version of any of the last five groups; and
$R_3$ is a group of the formula:
—Y$_2$—X$_1$—Y$_3$—R$_5$
wherein:
Y$_2$ is a covalent bond;
X$_1$ is arenediyl$_{(c≤12)}$, heteroarenediyl$_{(c≤12)}$, or a substituted version of either group; and
Y$_3$ is alkanediyl$_{(c≤8)}$ or substituted alkanediyl$_{(c≤8)}$;
$R_5$ is hydroxy, amino, alkylamino$_{(c≤8)}$, substituted alkylamino$_{(c≤8)}$, dialkylamino$_{(c≤12)}$, substituted dialkylamino$_{(c≤12)}$, or —NR$_c$C(NR$_d$)R$_5'$, wherein:
  R$_c$ and R$_d$ are each independently hydrogen, alkyl$_{(c≤6)}$, or substituted alkyl$_{(c≤6)}$;
  R$_5'$ is amino, alkylamino$_{(c≤8)}$, substituted alkylamino$_{(c≤8)}$, dialkylamino$_{(c≤12)}$, or substituted dialkylamino$_{(c≤12)}$;
provided $R_2$ is not hydroxy or $R_5$ is amino, alkylamino$_{(c≤8)}$, substituted alkylamino$_{(c≤8)}$, dialkylamino$_{(c≤12)}$, substituted dialkylamino$_{(c≤12)}$, or —NR$_c$C(NR$_d$)R$_5'$;

or a pharmaceutically acceptable salt thereof.

10. The compound of claim 1, wherein X$_1$ is arenediyl$_{(c≤12)}$ or substituted arenediyl$_{(c≤12)}$.

11. The compound of claim 1, wherein Y$_3$ is alkanediyl$_{(c≤8)}$.

12. The compound of claim 1, wherein R$_5$ is amino or —NR$_c$C(NR$_d$)R$_5'$.

13. The compound of claim 1, wherein the C ring adopts a chair confirmation.

14. The compound of claim 1, wherein the compound is further defined as:

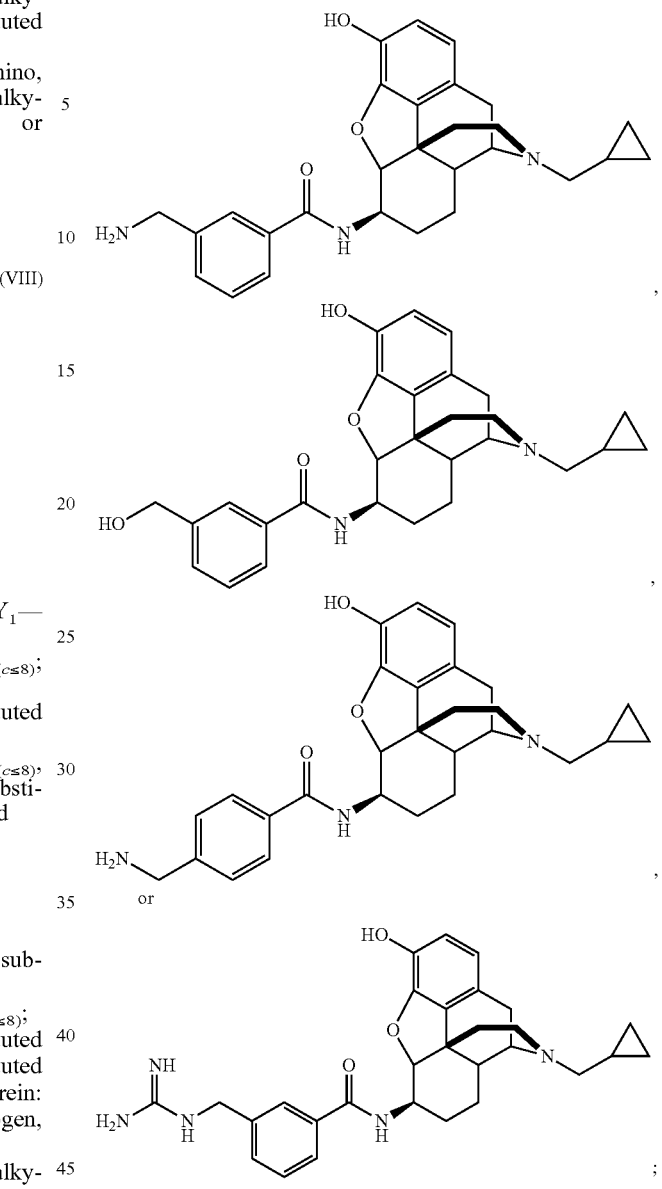

or a pharmaceutically acceptable salt thereof.

15. A pharmaceutical composition comprising:
(A) a compound of claim 1; and
(B) an excipient.

16. A method of treating the pain associated with a disease or disorder in a patient in need thereof comprising administering to the patient a therapeutically effective amount of a compound or composition of claim 1.

17. A method of alleviating pain in a patient in need thereof comprising administering to the patient a therapeutically effective amount of a compound or composition of claim 1.

18. The compound of claim 12, wherein R$_5$ is amino.

19. The compound of claim 12, wherein R$_5$ is —NR$_c$C(NR$_d$)R$_5'$.

* * * * *

UNITED STATES PATENT AND TRADEMARK OFFICE
CERTIFICATE OF CORRECTION

PATENT NO. : 11,613,547 B2
APPLICATION NO. : 16/924037
DATED : March 28, 2023
INVENTOR(S) : Susruta Majumdar et al.

It is certified that error appears in the above-identified patent and that said Letters Patent is hereby corrected as shown below:

In the Claims

In Claim 1, Column 74, Line 27, delete "$NR_cC(NR_d)R_5$" and insert -- $NR_cC(NR_d)R_5'$ -- therefore.

In Claim 6, Column 77, Line 49, delete "$NR_cC(NR_d)R_5$" and insert -- $NR_cC(NR_d)R_5'$ -- therefore.

In Claim 7, Column 78, Line 29, delete "$NR_cC(NR_d)R_5$" and insert -- $NR_cC(NR_d)R_5'$ -- therefore.

In Claim 8, Column 79, Line 7, delete "$NR_cC(NR_d)R_5$" and insert -- $NR_cC(NR_d)R_5'$ -- therefore.

In Claim 9, Column 79, Line 51, delete "$NR_cC(NR_d)R_5$" and insert -- $NR_cC(NR_d)R_5'$ -- therefore.

Signed and Sealed this
Thirteenth Day of June, 2023

Katherine Kelly Vidal
*Director of the United States Patent and Trademark Office*